US012747284B2

(12) United States Patent
Ho et al.

(10) Patent No.: US 12,747,284 B2
(45) Date of Patent: Sep. 29, 2026

(54) LASSA VIRUS-SPECIFIC NANOBODIES AND METHODS OF THEIR USE

(71) Applicant: The U.S.A., as represented by the Secretary, Department of Health and Human Services, Bethesda, MD (US)

(72) Inventors: Mitchell Ho, Urbana, MD (US); Peter D. Kwong, Washington, DC (US); Zhijian Duan, Columbia, MD (US); Yaping Sun, New Haven, CT (US); Sao-Fong Cheung, Rockville, MD (US); Jason J. Gorman, Lakeville, MA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 503 days.

(21) Appl. No.: 18/557,741

(22) PCT Filed: Apr. 29, 2022

(86) PCT No.: PCT/US2022/027082

§ 371 (c)(1),
(2) Date: Oct. 27, 2023

(87) PCT Pub. No.: WO2022/232612

PCT Pub. Date: Nov. 3, 2022

(65) Prior Publication Data

US 2024/0218055 A1 Jul. 4, 2024

Related U.S. Application Data

(60) Provisional application No. 63/181,519, filed on Apr. 29, 2021.

(51) Int. Cl.

| | |
|---|---|
| ***A61K 39/395*** | (2006.01) |
| ***A61K 47/68*** | (2017.01) |
| ***A61P 31/14*** | (2006.01) |
| ***C07K 16/10*** | (2006.01) |
| ***G01N 33/543*** | (2006.01) |
| ***G01N 33/569*** | (2006.01) |

(52) U.S. Cl.

CPC .......... *C07K 16/10* (2013.01); *A61K 47/6841* (2017.08); *A61P 31/14* (2018.01); *G01N 33/543* (2013.01); *G01N 33/56983* (2013.01); *C07K 2317/31* (2013.01); *C07K 2317/565* (2013.01); *C07K 2317/622* (2013.01); *C07K 2317/76* (2013.01); *G01N 2333/08* (2013.01)

(58) Field of Classification Search

None

See application file for complete search history.

(56) References Cited

U.S. PATENT DOCUMENTS 11,464,847 B2 * 10/2022 Jasny ...................... A61P 31/14

FOREIGN PATENT DOCUMENTS

| | | |
|---|---|---|
| WO | WO 2018/204080 | 11/2018 |
| WO | WO 2020/002525 | 1/2020 |
| WO | WO 2022/232648 | 11/2022 |

OTHER PUBLICATIONS

Dong et al., "Development of multi-specific humanized llama antibodies blocking SARS-CoV-2/ACE2 interaction with high affinity and avidity," *Emerg Microbes Infect* 9(1):1034-1036, 2020.

Hastie et al., "Structural basis for antibody-mediated neutralization of Lassa virus," *Science*, vol. 356:923-928, 2017.

International Search Report and Written Opinion for PCT/US2022/027082, dated Jul. 12, 2022 (21 pages).

Meier et al., "Foldon, The Natural Trimerization Domain of T4 Fibritin, Dissociates into a Monomeric A-state Form containing a Stable β-Hairpin: Atomic Details of Trimer Dissociation and Local β-Hairpin Stability from Residual Dipolar Couplings," *J. Mol. Biol.*, 344:1051-1069, 2004.

Reddington et al., "Secrets of a covalent interaction for biomaterials and biotechnology: SpyTag and SpyCatcher," *Curr. Opin. Chem. Biol.*, V29:94-99, 2015.

Robinson et al., "Most neutralizing human monoclonal antibodies target novel epitopes requiring both Lassa virus glycoproteins subunits," *Nat. Comm.*, 7:1-17, 2016.

* cited by examiner

*Primary Examiner* — Meera Natarajan

(74) *Attorney, Agent, or Firm* — Klarquist Sparkman, LLP

(57) ABSTRACT

Single-domain monoclonal antibodies that specifically bind Lassa virus glycoprotein (GPC) are described. The single-domain antibodies ("nanobodies") were isolated from camel ($V_H$H) and shark variable new antigen ($V_{NAR}$) phage display libraries panned against a stabilized form of the GPC trimer. The GPC-specific nanobodies, and conjugates thereof, can be used for the diagnosis and treatment of a Lassa virus infection.

23 Claims, 19 Drawing Sheets

Specification includes a Sequence Listing.

Cryo-EM structure of stabilized GPC trimer at 4 Å

Stability of stabilized GPC trimer

BLI affinity measurements of nanobodies

| Library | Nano body | Affinity (nM) | | |
|---|---|---|---|---|
| | | stabilized Lassa GPC trimer | GP1 | GP2 |
| Shark VNAR | A1 | 39.1 | 18.6 | ND |
| Shark VNAR | A10 | 14.3 | 22.7 | ND |
| Shark VNAR | B8 | 18.8 | 15.9 | ND |
| Shark VNAR | B10 | 44.5 | 78.6 | ND |
| Shark VNAR | C3 | 19.7 | ND | 10.6 |
| Camel VHH | D5 | 26.7 | 20.8 | ND |

Neutralization assessment in IgG2a format
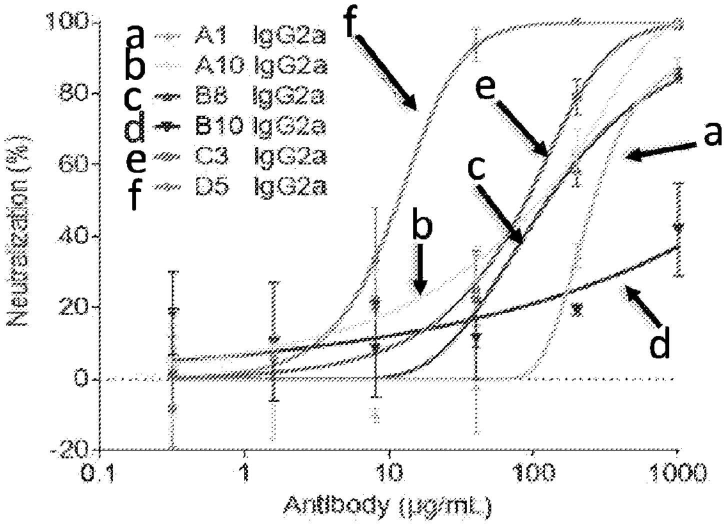
FIG. 3C
| Library | IgG 2a | IC50 (µg/ml) | IC90 (µg/ml) |
|---|---|---|---|
| Shark | A1 | 260 | 2393 |
| Shark | A10 | 111 | 513 |
| Shark | B8 | 120 | 6718 |
| Shark | B10 | NA | NA |
| Shark | C3 | 88 | 315 |
| Camel | D5 | 12 | 33 |
FIG. 3D
Binding kinetics of bivalent vs monovalent nanobodies toward GPC trimer
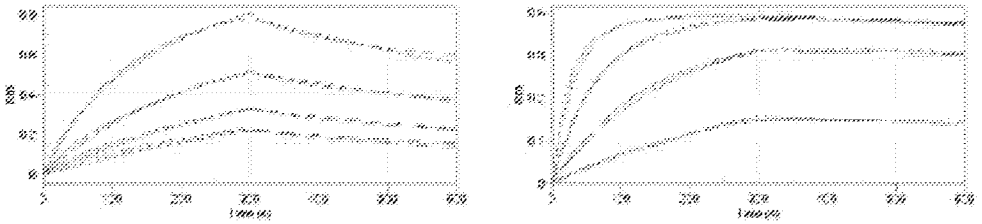
| | monovalent | bivalent |
|---|---|---|
| KD (M) | 3.26 E-8 | 3.02 E-10 |
| Kon ($M^{-1}s^{-1}$) | 3.50 E4 | 2.93 E5 |
| Kdis ($s^{-1}$) | 1.14 E-3 | 8.84 E-4 |

FIG. 4B

| | Nanobody | | | | | | GP1-A | | | GPC-A | | | GPC-B | | | GPC-C |
|---|---|---|---|---|---|---|---|---|---|---|---|---|---|---|---|---|
| | A1 | A10 | B8 | B10 | C3 | D5 | 10.4B | 12.1F | 19.7E | 8.11G | 25.10C | 36.1F | 18.5C | 25.6A | 37.7H | 8.9F |
| IC50 (monovalent) (μg/ml) | NA | NA | NA | NA | NA | NA | 269.75 | 0.61 | 15.28 | 5.88 | 0.18 | 0.40 | 0.46 | 0.07 | 0.04 | 0.39 |
| IC50 (bivalent) (μg/ml) | 260 | 111 | 120 | NA | 88 | 12 | 8.48 | 0.03 | 0.17 | 0.31 | 0.03 | 0.26 | 0.97 | 0.36 | 0.06 | 0.16 |

FIG. 4C

| | Nanobody | | | | | | GP1-A | | | GPC-A | | | GPC-B | | | GPC-C |
|---|---|---|---|---|---|---|---|---|---|---|---|---|---|---|---|---|
| | A1 | A10 | B8 | B10 | C3 | D5 | 10.4B | 12.1F | 19.7E | 8.11G | 25.10C | 36.1F | 18.5C | 25.6A | 37.7H | 8.9F |
| Number of GPC protomers targeted by a single nanobody or Fab | 1 | 1 | 1 | 1 | 1 | 1 | 1 | 1 | 1 | 1 | 1 | 1 | 2 | 2 | 2 | ? |
| Better IC50 neutralization | | | | NA | | | | | | | | | | | | |
| Mechanism of neutralization | Avidity | Avidity | Avidity | NA | Avidity | Avidity | Avidity | Avidity | Avidity | Avidity | Avidity | Avidity | Quarter-nary | Quarter-nary | Quarter-nary | ? |

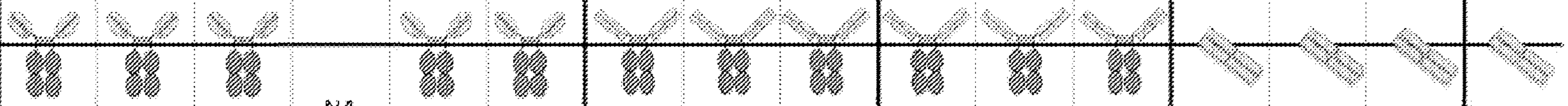

FIG. 6A
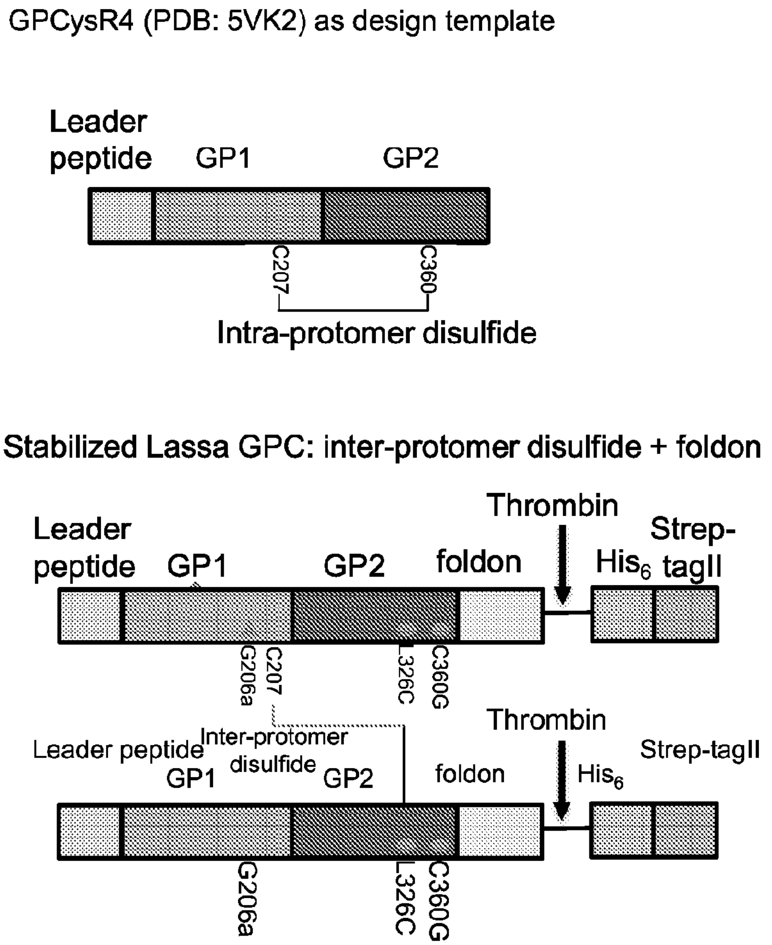
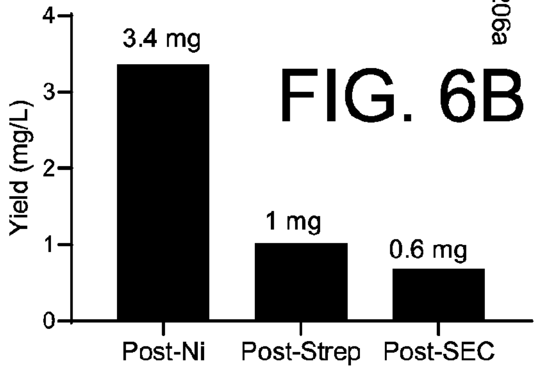
FIG. 6B
FIG. 6C
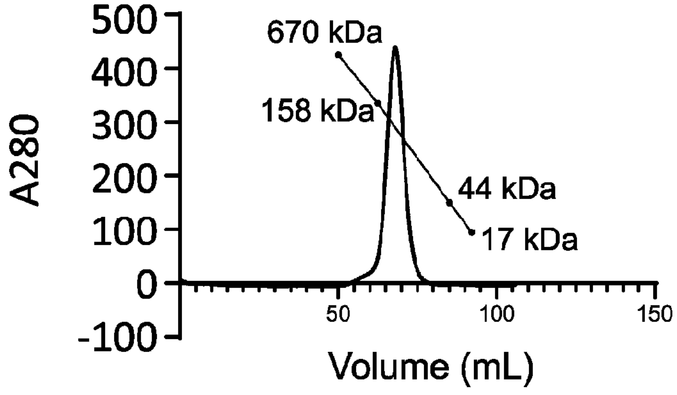

| Round | Input phage (Colony forming unit, CFU) | Output phage (Colony forming unit, CFU) |
|---|---|---|
| I | $1\times10^{12}$ | $5\times10^{3}$ |
| II | $1\times10^{12}$ | $5\times10^{3}$ |
| III | $1\times10^{12}$ | $5\times10^{5}$ |
| IV | $1\times10^{12}$ | $2\times10^{6}$ |

| Round | Input phage (Colony forming unit, CFU) | Output phage (Colony forming unit, CFU) |
|---|---|---|
| I | $1\times10^{12}$ | $5\times10^{3}$ |
| II | $1\times10^{12}$ | $3\times10^{2}$ |
| III | $1\times10^{12}$ | $1\times10^{5}$ |
| IV | $1\times10^{12}$ | $6\times10^{6}$ |

Binding of the select nanobodies toward Lassa GPC trimers from different lineages

GPC C1

GPC C3

GPC C1
D5
8.11G

Cryo-EM data, reconstruction, refinement, and validation statistics

FIG. 9

| | Lassa GPC Trimer in complex with Fab 8.11G and nanobody D5 | Ligand-free Lassa GPC trimer C1 symmetry | Ligand-free Lassa GPC trimer C3 symmetry |
|---|---|---|---|
| **EMDB ID** | xxxxx | xxxxx | xxxxx |
| **PDB ID** | xxxx | | |
| Data collection | | | |
| Microscope | FEI Titan Krios | FEI Titan Krios | FEI Titan Krios |
| Voltage (kV) | 300 | 300 | 300 |
| Electron dose ($e^-/Å^2$) | 51.15 | 56.52 | 56.52 |
| Detector | Gatan K3 | Gatan K2 | Gatan K2 |
| Pixel Size (Å) | 1.083 | 1.076 | 1.076 |
| Defocus Range (μm) | -1.0 to -2.5 | -1.0 to -2.5 | -1.0 to -2.5 |
| Magnification | 81000 | 22500 | 22500 |
| Reconstruction | | | |
| Software | cryoSparcV3.3 | cryoSparcV3.3 | cryoSparcV3.3 |
| Particles | 109,878 | 43,577 | 47,597 |
| Symmetry | C1 | C1 | C3 |
| Box size (pix) | 300 | 256 | 256 |
| Resolution (Å) ($FSC_{0.143}$) | 4.70 | 6.58 | 5.82 |
| Refinement | | | |
| Software | Phenix 1.19 | | |
| Protein residues | 12269 | | |
| Chimera CC | 0.82 | | |
| EMRinger Score | 0.97 | | |
| R.m.s. deviations | | | |
| Bond lengths (Å) | 0.007 | | |
| Bond angles (°) | 0.776 | | |
| Validation | | | |
| Molprobity score | 2.19 | | |
| Clash score | 6.89 | | |
| Favored rotamers (%) | 99.1 | | |
| Ramachandran | | | |
| Favored regions (%) | 91.1 | | |
| Disallowed regions (%) | 0.5 | | |

FIG. 10A

BLI binding data of Fabs of human Lassa nAbs toward stabilized LASV GPC trimer.

| Fab | | |
|---|---|---|
| 10.4B | KD (M) | 6.63 E-08 |
| | Kon (M$^{-1}$s$^{-1}$) | 5.38 E+04 |
| | Kdis (s$^{-1}$) | 3.57 E-03 |
| 12.1F | KD (M) | 3.64 E-08 |
| | Kon (M$^{-1}$s$^{-1}$) | 2.81 E+04 |
| | Kdis (s$^{-1}$) | 1.02 E-03 |
| 19.7E | KD (M) | 1.57 E-07 |
| | Kon (M$^{-1}$s$^{-1}$) | 8.48 E+03 |
| | Kdis (s$^{-1}$) | 1.33 E-03 |
| 8.11G | KD (M) | 3.71 E-08 |
| | Kon (M$^{-1}$s$^{-1}$) | 3.68 E+04 |
| | Kdis (s$^{-1}$) | 1.37 E-03 |
| 25.10C | KD (M) | 8.56 E-09 |
| | Kon (M$^{-1}$s$^{-1}$) | 2.82 E+05 |
| | Kdis (s$^{-1}$) | 2.41 E-03 |

| Fab | | |
|---|---|---|
| 36.1F | KD (M) | 1.52 E-08 |
| | Kon (M$^{-1}$s$^{-1}$) | 1.71 E+05 |
| | Kdis (s$^{-1}$) | 2.61 E-03 |
| 18.5C | KD (M) | 7.31 E-09 |
| | Kon (M$^{-1}$s$^{-1}$) | 5.35 E+04 |
| | Kdis (s$^{-1}$) | 3.91 E-04 |
| 25.6A | KD (M) | 1.54 E-08 |
| | Kon (M$^{-1}$s$^{-1}$) | 1.64 E+05 |
| | Kdis (s$^{-1}$) | 2.53 E-03 |
| 37.7H | KD (M) | 4.47 E-09 |
| | Kon (M$^{-1}$s$^{-1}$) | 1.85 E+05 |
| | Kdis (s$^{-1}$) | 8.28 E-04 |

BLI binding data of nanobodies toward stabilized LASV GPC trimer, GP1 and GP2.

| Nanobody | | GPC | GP1 | GP2 |
|---|---|---|---|---|
| A1 | KD (M) | 3.91 E-08 | 18.6 E-08 | / |
| | Kon (M$^{-1}$s$^{-1}$) | 3.42 E+04 | 1.76 E+04 | |
| | Kdis (s$^{-1}$) | 1.34 E-03 | 3.28 E-03 | |
| A10 | KD (M) | 1.43 E-08 | 2.27 E-08 | / |
| | Kon (M$^{-1}$s$^{-1}$) | 4.43 E+05 | 1.05 E+04 | |
| | Kdis (s$^{-1}$) | 6.33 E-03 | 2.38 E-03 | |
| B8 | KD (M) | 1.88 E-08 | 1.57 E-08 | / |
| | Kon (M$^{-1}$s$^{-1}$) | 1.76 E+06 | 1.49 E+05 | |
| | Kdis (s$^{-1}$) | 3.31 E-03 | 2.36 E-03 | |
| B10 | KD (M) | 4.45 E-08 | 7.90 E-08 | / |
| | Kon (M$^{-1}$s$^{-1}$) | 2.23 E+05 | 5.27 E+04 | |
| | Kdis (s$^{-1}$) | 9.92 E-03 | 4.14 E-03 | |
| C3 | KD (M) | 1.97 E-08 | / | 1.06 E-08 |
| | Kon (M$^{-1}$s$^{-1}$) | 3.49 E+05 | | 2.51 E+04 |
| | Kdis (s$^{-1}$) | 6.88 E-03 | | 2.65 E-04 |
| D5 | KD (M) | 2.67 E-08 | 2.08 E-08 | / |
| | Kon (M$^{-1}$s$^{-1}$) | 1.21 E+05 | 2.34 E+04 | |
| | Kdis (s$^{-1}$) | 3.23 E-03 | 1.87 E-04 | |

FIG. 10B

LASSA VIRUS-SPECIFIC NANOBODIES AND METHODS OF THEIR USE

CROSS REFERENCE TO RELATED APPLICATIONS

This application is the U.S. National Stage of International Application No. PCT/US2022/027082, filed Apr. 29, 2022, which was published in English under PCT Article 21(2), which claims the benefit of U.S. Provisional Application No. 63/181,519, filed Apr. 29, 2021. The above-listed applications are herein incorporated by reference in their entireties.

ACKNOWLEDGMENT OF GOVERNMENT SUPPORT

This invention was made with government support under project numbers Z01 BC 010891, ZIA BC 010891, ZIC BC 011891, and ZIA-AI005024-19 awarded by the National Institutes of Health. The government has certain rights in the invention.

FIELD

This disclosure concerns shark and camel single-domain monoclonal antibodies that specifically bind Lassa virus (LASV) glycoprotein (GPC) and their use, such as for diagnosing and treating a LASV infection.

INCORPORATION OF ELECTRONIC SEQUENCE LISTING

The Sequence Listing is submitted as an ASCII text file, named 106147-03_ST25.txt, 11,925 bytes, created on Oct. 4, 2023, which is herein incorporated by reference.

BACKGROUND

Lassa virus (LASV), an Old World arenavirus that causes the acute viral hemorrhagic illness Lassa fever, is highly prevalent in West Africa, infecting 100,000 to 300,000 individuals each year, with approximately 5,000 deaths (Shaffer et al., *PLOS Negl Trop Dis* 8, e2748, 2014; Asogun et al., *PLOS Negl Trop Dis* 6, e1839, 2012). The LASV outbreak in Nigeria in 2018 had more than 300 confirmed cases, with a case fatality rate of approximately 25% (Ilori et al., *Emerg Infect Dis* 25, 1066-1074, 2019). No licensed vaccine is available for the prevention of Lassa fever, and the only treatment is ribavirin, a broad-spectrum antiviral (Eberhardt et al., *Int J Infect Dis* 87, 15-20, 2019). With the growing threat of spreading globally (Gouglas et al., *Epidemiol Rev* 41, 28-33, 2019), LASV has been included on the priority pathogen list for the World Health Organization's R&D Blueprint for Action to Prevent Epidemics in an urgent effort to develop effective vaccines (Salami et al., *Vaccine* 38, 4135-4141, 2020; Bernasconi et al., *Bundesgesundheitsblatt Gesundheitsforschung Gesundheitsschutz* 63, 65-73, 2020).

LASV is an enveloped RNA virus covered with glycoprotein complex (GPC) trimer spikes (Li et al., *PLOS* Pathog 12, e1005418, 2016; Schlie et al., *J Virol* 84, 983-992, 2010), which are the major viral antigen. Each protomer of the GPC trimer consists of a receptor-binding GP1 subunit, a transmembrane-spanning GP2 subunit, and the stable signal peptide (SSP), which originates from the precursor for proper processing and function (Hastie et al., *Science* 356, 923-928, 2017; Igonet et al., *Proc Natl Acad Sci USA* 108, 19967-19972, 2011; York and Nunberg, *J Virol* 90, 8341-8350, 2016; Eichler et al., *EMBO Rep* 4, 1084-1088, 2003). The majority of LASV vaccine development efforts have focused on the GPC present on the virion envelope. However, there has been very limited success due to the highly glycosylated GPC inducing only a weak and inconsistent immune response in both natural infection and vaccination (Baize et al., *J Virol* 83, 5890-5903, 2009; Fisher-Hoch et al., *J Virol* 74, 6777-6783, 2000; Sommerstein et al., *PLOS Pathog* 11, e1005276, 2015; Warner et al., *Drug Des Devel Ther* 12, 2519-2527, 2018; Lukashevich and Pushko, *Expert Rev Vaccines* 15, 1135-1150, 2016). The limited number of LASV neutralizing antibodies isolated further impedes LASV vaccine research, as neutralizing antibodies are critical to providing insights to vaccine design (Kwong et al., *Cold Spring Harb Perspect Med* 1, a007278, 2011).

LASV neutralizing antibodies are scarce and so far only 16 have been reported to be isolated from Lassa fever convalescent patients after analyzing over 100 antibodies (Robinson et al., *Nat Commun* 7, 11544, 2016). These 16 neutralizing antibodies are categorized into four competition groups—GP1-A, GPC-A, GPC-B, and GPC-C—based on their recognition sites and cross-reactivity. The GP1-A group is comprised of three antibodies (10.4B, 12.1F, and 19.7E) that bind GP1 but not the GP2 subunit. In contrast, the other three groups recognize fully assembled GPC trimer. The GPC-A group contains three antibodies (8.11G, 25.10C, and 36.1F); the GPC-B group contains nine antibodies (2.9D, 18.5C, 25.6A, 36.9F, 37.2D, 37.2G, 37.7H, and NE13); and the GPC-C group has a single antibody (8.9F) (Robinson et al., *Nat Commun* 7, 11544, 2016). Antibodies recognizing only the GP2 subunit are not neutralizing (Robinson et al., *Nat Commun* 7, 11544, 2016). GP1-A and GPC-A antibodies recognize LASV GPC trimer with 1:1 stoichiometry ratio (one Fab binding one single GPC protomer) (Cross et al., *Curr Opin Virol* 37, 97-104, 2019), whereas each Fab of GPC-B antibodies bind across two adjacent GPC protomers at the interface in the assembly (Hastie et al., *Science* 356, 923-928, 2017). Half of this quaternary epitope (site A) contains portions of the T-loop and heptad repeat 2 (HR2) of GPC protomer A, while the other half (site B) contains the fusion peptide and HR1 of GPC protomer B (Hastie et al., *Science* 356, 923-928, 2017; Hastie et al., *Cell* 178, 1004-1015.e1014, 2019). Such binding that bridges two GPC protomers, referred to as inter-protomer quaternary recognition, effectively locks the trimers in a prefusion state to mediate neutralization (Hastie et al., *Science* 356, 923-928, 2017; Hastie et al., *Cell* 178, 1004-1015.e1014, 2019). For the GPC-C antibody 8.9F, its exact epitope remains unclear.

SUMMARY

Described herein are single-domain camel $V_HH$ and shark variable new antigen receptor ($V_{NAR}$) monoclonal antibodies ("nanobodies") that specifically bind the Lassa virus (LASV) glycoprotein (GPC) with high affinity. The disclosed nanobodies are capable of neutralizing pseudotyped virus expressing LASV GPC.

Provided herein are polypeptides (for example, single-domain monoclonal antibodies) that bind, such as specifically bind, a stabilized LASV GPC trimer. In some embodiments, the polypeptide includes the complementarity determining region (CDR) sequences of antibody D5, C3, A1, A10, B8 or B10. Also provided herein are conjugates that include a disclosed polypeptide. In some examples, provided are fusion proteins (such as Fc fusion proteins), chimeric antigen receptors (CARs), CAR-expressing cells (such as T cells, natural killer cells and macrophages), immunoconjugates (such as immunotoxins), multi-specific antibodies (such as bispecific antibodies), antibody-drug conjugates (ADCs), antibody-nanoparticle conjugates, and antibody-radioisotope conjugates (such as for immunoPET imaging) that include a polypeptide (for example, a single-domain monoclonal antibody) disclosed herein. In some examples, the fusion protein includes a single-domain monoclonal antibody fused to a human Fc domain via a hinge region, such as a llama IgG2a hinge region.

Further provided are compositions that include at least two (such as at least two, at least three, at least four, at least five or six) different LASV GPC-specific polypeptides disclosed herein.

Also provided herein are nucleic acid molecules and vectors encoding the LASV GPC-specific polypeptides (for example, antibodies), fusion proteins, CARs, immunoconjugates (such as immunotoxins), and multi-specific antibodies disclosed herein. Isolated cells that include a nucleic acid or vector encoding a GPC-specific polypeptide or CAR are further provided.

Compositions that include a pharmaceutically acceptable carrier and a LASV GPC-specific polypeptide, fusion protein, CAR, immunoconjugate, ADC, multi-specific antibody, antibody-nanoparticle conjugate, isolated nucleic acid molecule or vector disclosed herein are also provided by the present disclosure. Also provided are solid supports, such as beads (e.g., glass, magnetic, or plastic beads), multiwell plates, paper, or nitrocellulose that include one or more GPC-specific polypeptides (such as single-domain monoclonal antibodies) provided herein. Also provided are kits that include a LASV GPC-specific polypeptide, fusion protein, CAR, immunoconjugate, ADC, multi-specific antibody, antibody-nanoparticle conjugate, isolated nucleic acid molecule or vector disclosed herein. Such kits can include additional elements, such as a solid support (e.g., a bead or multi-well plate), a detectably labeled secondary antibody that permits detection of the antibody that specifically binds LASV GPC, or both. In some examples such kits include materials for administration of a LASV GPC-specific polypeptide, fusion protein, CAR, immunoconjugate, ADC, multi-specific antibody, antibody-nanoparticle conjugate, isolated nucleic acid molecule or vector disclosed herein, such as a syringe.

Methods of detecting LASV in a sample, and methods of diagnosing a subject as having a LASV infection, are further provided. In some embodiments, the methods include contacting a sample obtained from the subject with a polypeptide (for example, a single-domain monoclonal antibody) disclosed herein, and detecting binding of the polypeptide to the sample.

Also provided is a method of treating a LASV infection in a subject. In some embodiments, the method includes administering to the subject a therapeutically effective amount of a polypeptide (for example, a single-domain monoclonal antibody) disclosed herein, or administering to the subject a therapeutically effective amount of a fusion protein, CAR (or CAR immune cells, such as CAR T cells, CAR NK cells or CAR macrophages), immunoconjugate (such as an immunotoxin), ADC, multi-specific antibody, or antibody-nanoparticle conjugate comprising a polypeptide disclosed herein, or a nucleic acid molecule or vector encoding a disclosed polypeptide.

The foregoing and other objects and features of the disclosure will become more apparent from the following detailed description, which proceeds with reference to the accompanying figures.

BRIEF DESCRIPTION OF THE DRAWINGS

(FIG. 1A) Structure-based design of stabilized soluble Lassa virus GPC trimer. An inter-protomer disulfide (DS) bond links GP1 of one protomer to GP2 of a neighboring protomer. A foldon domain was appended to the C-terminus of GP2. The right panel shows a zoom-in view around the inter-protomer DS with the mutations to create the DS marked by spheres and labeled. Cys360, which in GPCysR4 (PDB: 5VK2) forms a disulfide with Cys207, was mutated to glycine. The two front protomers are shown as ribbons. The protomer in the back is shown as a white surface. (FIG. 1B) SDS-PAGE of stabilized LASV trimer under non-reducing and reducing conditions. A high molecular weight band three times the molecular weight of the monomeric form was observed in the non-reducing condition. (FIG. 1C) Binding affinity of the stabilized LASV GPC trimer toward Fabs of four groups of human LASV-neutralizing antibodies: GP1-A, GPC-A, GPC-B, and GPC-C. (FIG. 1D) Negative-stain electron microscopy (EM) images of the stabilized LASV GPC trimer alone and in complex with 4 groups of human neutralizing Fabs. Representative top view and side view are shown. (FIG. 1E) Cryo-EM structure of the stabilized LASV GPC at 4 Å reveals the trimeric association of the protein. (FIG. 1F) Physical properties of the stabilized LASV GPC trimer. Stability of the stabilized trimer was assessed as fractional binding reactivity to 37.7H after treatments under various temperatures, pH, osmolarity changes and freeze-thaw cycles. Triplicate measurements were made, and results are represented as mean±SEM. The dotted line shows the antibody reactivity of the trimer prior to physical stress.

(FIG. 2A) Five nanobodies from shark (A1, A10, B8, B10, C3) and one nanobody from camel (D5) libraries showed binding to the stabilized LASV GPC trimer by ELISA. A potent human Lassa virus neutralizing antibody, 37.7H, was used as a positive control. Select nanobodies showed minimal reactivity toward bovine serum albumin (BSA). Triplicate measurements were made and results are represented as mean±SEM. (FIG. 2B) Binding affinities of the six nanobodies toward the stabilized GPC trimer, GP1 and GP2 subunits (ND, not detected). (FIG. 2C) Cross-competition between the six nanobodies and four groups of human Lassa virus neutralizing antibodies toward the stabilized LASV GPC trimer. Epitope binding was performed using biolayer interferometry. His-tagged stabilized LASV GPC trimer was loaded onto the NTA sensor tips; then the blocking ligand was loaded, followed by loading of the second ligand. The numerical data indicate percent binding of the binding ligand in the presence of the blocking ligand.

FIGS. 3A-3D: Nanobodies formatted in IgG2a showed neutralization against Lassa virus. (FIG. 3A) Six monovalent nanobodies did not significantly neutralize pseudotyped Lassa Josiah virus. (FIG. 3B) Schematic diagram (left) showing a nanobody linked to human Fc with the llama IgG2a hinge linker. Knob (T336Y)-into-hole (Y407T) mutations were engineered in the CH3 domain for dimerization. SDS-PAGE (right) of purified bivalent nanobodies in IgG2a format. (FIG. 3C) Five out of six nanobodies arranged in IgG2a format showed neutralization against pseudotyped virus expressing LASV GPC. The IC50 and IC90 values are shown in the table. (FIG. 3D) BLI analysis of difference concentrations of monovalent and bivalent D5 binding to immobilized LASV GPC trimer. Equilibrium (KD) constants are provided.

FIGS. 4A-4C: Neutralization of Lassa virus by nanobodies and most human neutralizing antibodies requires avidity. (FIG. 4A) Neutralization of pseudotyped Josiah strain of Lassa virus by nanobodies and human Lassa neutralizing antibodies in both monovalent (dotted line) and bivalent (solid line) formats. (FIG. 4B) Summary of the IC50 values of nanobodies and human Lassa virus neutralizing antibodies in monovalent and bivalent formats. (FIG. 4C) Summary of the proposed neutralization mechanisms of nanobodies and human antibodies for Lassa virus.

(FIG. 5A) Cryo-EM density is shown for a complex of the stabilized GPC trimer bound to two Fabs of 8.11G and a single D5. An unliganded trimer is shown in the right panel highlighting the cavity where D5 binds. (FIG. 5B) The atomic model is shown in cartoon representation. A 5 Å footprint of D5 is shown, highlighting interactions with all three protomers. (FIG. 5C) The highly glycosylated epitope of 8.11G is highlighted. (FIG. 5D) A single protomer of the GPC trimer shows a closely matching RMSD with that of the C3 symmetric GPC bound to 37.7H (PDB iD 5VK2). The C1 symmetric GPC trimer observed here does not maintain the same quaternary assembly with the adjacent protomer oriented to accommodate the uncleaved peptide. A schematic explanation for the loss of one of the three 37.7H (GPC-B nAb) binding sites on the trimer is shown at the right. (FIG. 5E) The Lassa virus GPC is shown with a focus on one of the two cleaved protomers (left) with the internal termini of GP1 and GP2. Rotation by 120° shows the external location of the uncleaved peptide. (FIG. 5F) Schematic representation of the cleavage intermediates in the maturation of the GPC trimer is shown from a top view looking down the trimer axis. The SIP cleavage site must be cleaved on all three protomers to enable a tightly packed GPC trimer. The neutralizing nanobody D5 binds the first three populations (uncleaved, single-cleavage and double-cleaved).

FIGS. 6A-6C: Construct, yield, and purification profile of stabilized soluble Lassa virus GPC trimer. (FIG. 6A) Schematic showing the design of GPCysR4 (top) and stabilized soluble Lassa virus GPC trimer (bottom). The original C207-C360 intra-protomer disulfide in GPCysR4 was abolished by mutating C360G. A new inter-protomer disulfide was created between C207 and L326C. Insertion of G206A allowed optimal geometry for disulfide bond formation. A T4-fibritin (foldon) trimerization domain was also introduced at the C-terminus to fix the base of the trimer. (FIG. 6B) Protein yield of the stabilized soluble GPC trimer following nickel-affinity (Ni), streptavidin-affinity (Strep), and size exclusion (SEC) purification. (FIG. 6C) SEC profile of the stabilized soluble GPC trimer on Superdex 200 16/600 column.

(FIG. 7A) Results of phage ELISA following different rounds of stabilized LASV GPC panning by the shark $V_{NAR}$ library. Input phage and output phage titers are shown below the graph. (FIG. 7B) Results of phage ELISA following different rounds of stabilized LASV GPC panning by the camel $V_HH$ library. Input phage and output phage titers are shown below the graph. (FIG. 7C) Sequences of the nanobodies (SEQ ID NOs: 3, 4, 5, 6, 2 and 1, from top to bottom). The framework regions (FR) and CDRs, as determined using IMGT, are labelled. (FIG. 7D) Binding of select nanobodies to trimers from 7 different lineages of Lassa virus. Bars from left to right represent the Pinneo, AYM51697, 803213, GA391, CSF, AV and KAKO428 lineages.

(FIG. 8A) Representative micrographs and CTFs of the micrographs. (FIG. 8B) Representative 2D class averages. (FIG. 8C) The gold-standard Fourier shell correlation are shown with the resolution for the three maps. (FIG. 8D) The orientations of all particles used in the final refinements are shown as heatmaps.

FIG. 9: Table of Cryo-EM data, reconstruction, refinement and validation statistics.

FIGS. 10A-10B: BLI binding data. (FIG. 10A) Table of BLI binding data of Fabs of Lassa virus nanobodies toward stabilized LASV GPC trimer. (FIG. 10B) Table of BLI binding data of nanobodies toward stabilized LASV GPC trimer, GP1 and GP2.

SEQUENCE LISTING

Figure 1A:
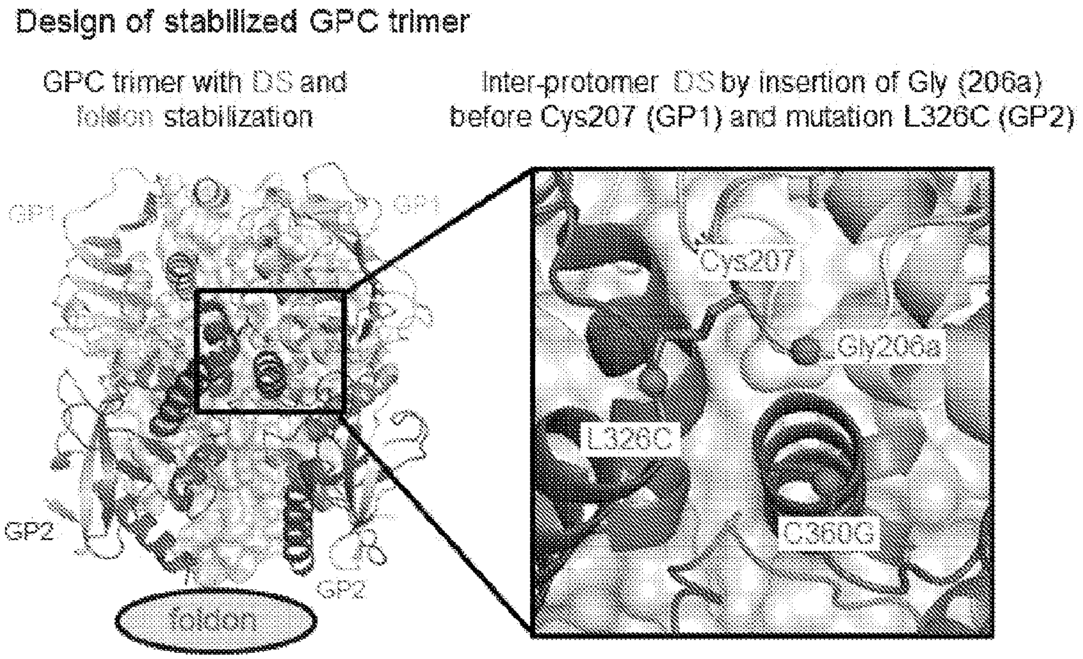
FIGS. 1A-1F: Design and characterization of stabilized soluble LASV GPC trimer.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of camel $V_HH$ D5.

SEQ ID NO: 2 is the amino acid sequence of shark $V_{NAR}$ C3.

SEQ ID NO: 3 is the amino acid sequence of shark $V_{NAR}$ A1.

SEQ ID NO: 4 is the amino acid sequence of shark $V_{NAR}$ A10.

SEQ ID NO: 5 is the amino acid sequence of shark $V_{NAR}$ B8.

SEQ ID NO: 6 is the amino acid sequence of shark $V_{NAR}$ B10.

SEQ ID NO: 7 is the amino acid sequence of the llama IgG2a hinge.

SEQ ID NO: 8 is the amino acid sequence of stabilized GPC.

SEQ ID NO: 9 is an exemplary nucleic acid sequence encoding camel $V_HH$ D5.

DETAILED DESCRIPTION

I. Abbreviations

ADC antibody-drug conjugate
CAR chimeric antigen receptor
CDR complementarity determining region
EM electron microscopy
FR framework region
GP glycoprotein
GPC glycoprotein complex
HRP horseradish peroxidase
HV hypervariable
IC50 50% inhibitory concentration LASV Lassa virus
MOI multiplicity of infection
RLU relative light units
$V_{NAR}$ variable domain of the immunoglobulin new antigen receptor
VSV vesicular stomatitis virus

II. Terms and Methods

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Administration: To provide or give a subject an agent, such as a polypeptide (for example, a single-domain monoclonal antibody) provided herein, by any effective route. Exemplary routes of administration include, but are not limited to, oral, injection (such as subcutaneous, intramuscular, intradermal, intraperitoneal, and intravenous), sublingual, rectal, transdermal, intranasal, vaginal and inhalation routes.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_{NAR}$ antibodies, camelid $V_H$H antibodies, $V_H$ domain antibodies and Vl domain antibodies. $V_{NAR}$ antibodies are produced by cartilaginous fish, such as nurse sharks, wobbegong sharks, spiny dogfish and bamboo sharks. Camelid $V_H$H antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by known methods. Monoclonal antibodies include humanized monoclonal antibodies.

A "chimeric antibody" has framework residues from one species, such as human, and CDRs (which generally confer antigen binding) from another species, such as a $V_{NAR}$ that specifically binds a viral antigen.

A "humanized" antibody is an immunoglobulin including a human framework region and one or more CDRs from a non-human (for example a shark, mouse, rabbit, rat, or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions. Methods of humanizing shark $V_{NAR}$ antibodies has been previously described (Kovalenko et al., *J Biol Chem* 288(24): 17408-17419, 2013).

Antibody-drug conjugate (ADC): A molecule that includes an antibody (or antigen-binding fragment of an antibody) conjugated to a drug, such as an anti-viral agent or a cytotoxic agent. ADCs can be used to specifically target a drug to particular cells through specific binding of the antibody to a target antigen expressed on the cell surface. Exemplary drugs for use with ADCs include anti-viral agents (such as remdesivir, galidesivir, arbidol, favipiravir, baricitinib, or lopinavir/ritonavir), anti-microtubule agents (such as maytansinoids, auristatin E and auristatin F) and interstrand crosslinking agents (for example, pyrrolobenzodiazepines; PBDs). In some cases, the ADC is a bi-specific ADC, which is comprised of two monoclonal antibodies or antigen-fragments thereof, each directed to a different antigen or epitope, conjugated to a drug. In one example, the agent attached to the antibody is IRDye® 700 DX (IR700, Li-cor, Lincoln, NE), which can then be used with near infrared light NIR light to kill target cells to which the antibody binds (photoimmunotherapy; see for example U.S. Pat. Nos. 8,524,239 and 10,538,590). For example, amino-reactive IR700 can be covalently conjugated to an antibody using the NHS ester of IR700.

Binding affinity: Affinity of an antibody for an antigen. In one embodiment, affinity is calculated by a modification of the Scatchard method described by Frankel et al., *Mol. Immunol.,* 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In some embodiments, binding affinity is measured using the Octet system (Creative Biolabs), which is based on bio-layer interferometry (BLI) technology. In other embodiments, Kd is measured using surface plasmon resonance assays using a BIACORES-2000 or a BIACORES-3000 (BIAcore, Inc., Piscataway, N.J.). In other embodiments, antibody affinity is measured by flow cytometry or by surface plasmon reference. An antibody that "specifically binds" an antigen (such as LASV glycoprotein) is an antibody that binds the antigen with high affinity and does not significantly bind other unrelated antigens. In some examples, a monoclonal antibody (such as an anti-LASV GPC single-domain antibody provided herein) specifically binds to a target (for example, a LASV GPC) with an equilibrium constant (Kd) of 50 nM or less, such as 45 nM or less, 40 nM or less, 35 nM or less, 30 nM or less, 25 nM or less, 20 nM or less, 15 nM or less, 10 nM or less, or 5 nM or less.

Bispecific antibody: A recombinant protein that includes antigen-binding fragments of two different monoclonal antibodies, and is thereby capable of binding two different antigens or two different epitopes of the same antigen. Similarly, a multi-specific antibody is a recombinant protein that includes antigen-binding fragments of at least two different monoclonal antibodies, such as two, three or four different monoclonal antibodies.

Chimeric antigen receptor (CAR): A chimeric molecule that includes an antigen-binding portion (such as single-domain antibody) and a signaling domain, such as a signaling domain from a T cell receptor (for example, CD3ζ). Typically, CARs are comprised of an antigen-binding moiety, a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10. In some examples, the CAR is multispecific (such as bispecific) or bicistronic. A multispecific CAR is a single CAR molecule comprised of at least two antigen-binding domains (such as scFvs and/or single-domain antibodies) that each bind a different antigen or a different epitope on the same antigen (see, for example, US 2018/0230225). For example, a bispecific CAR refers to a single CAR molecule having two antigen-binding domains that each bind a different antigen. A bicistronic CAR refers to two complete CAR molecules, each containing an antigen-binding moiety that binds a different antigen. In some cases, a bicistronic CAR construct expresses two complete CAR molecules that are linked by a cleavage linker. Induced pluripotent stem cells (iPSCs) or immune cells (such as T cells, NK cells or macrophages) expressing a bispecific or bicistronic CAR can bind cells that express both of the antigens to which the binding moieties are directed (see, for example, Qin et al., *Blood* 130:810, 2017; and WO/2018/213337).

Complementarity determining region (CDR): A region of hypervariable amino acid sequence that defines the binding affinity and specificity of an antibody. The camel single-domain antibodies disclosed herein include three CDRs (CDR1, CDR2 and CDR3) while the shark $V_{NAR}$ single-domain antibodies disclosed herein include two CDRs (CDR1 and CDR3). Shark $V_{NAR}$ antibodies further include two hypervariable regions, referred to as HV2 and HV4.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, carbohydrate or recombinant virus. An antibody conjugate is often referred to as an "immunoconjugate." When the conjugate includes an antibody linked to a drug (e.g., a cytotoxic agent), the conjugate is often referred to as an "antibody-drug conjugate" or "ADC." Other antibody conjugates include, for example, multi-specific (such as bispecific or trispecific) antibodies and chimeric antigen receptors (CARs).

Conservative variant: "Conservative" amino acid substitutions are those substitutions that do not substantially affect or decrease the affinity of a protein. For example, a monoclonal antibody that specifically binds a target antigen (such as GPC) can include at most about 1, at most about 2, at most about 5, at most about 10, or at most about 15 conservative substitutions and specifically bind the target antigen. The term "conservative variant" also includes the use of a substituted amino acid in place of an unsubstituted parent amino acid, provided that the antibody specifically binds the target antigen. Non-conservative substitutions are those that reduce an activity or binding to the target antigen.

Conservative amino acid substitution tables providing functionally similar amino acids are well-known. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a polypeptide or an antibody that includes a sequence that is degenerate as a result of the genetic code. There are 20 natural amino acids, most of which are specified by more than one codon. Therefore, all degenerate nucleotide sequences are included as long as the amino acid sequence of the polypeptide or antibody encoded by the nucleotide sequence is unchanged.

Diagnostic: Identifying the presence or nature of a pathologic condition, such as, but not limited to, a viral infection (e.g., a LASV infection). Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or metastasis.

Diagnostic imaging: Coupling antibodies and their derivatives with positron emitting radionuclides for positron emission tomography (PET) is a process often referred to as immunoPET. While full length antibodies can make good immunoPET agents, their biological half-life necessitates waiting several days prior to imaging, resulting in an increase in non-target radiation doses. Smaller, single domain antibodies, or nanobodies, have biological half-lives amenable to same day imaging.

Drug: Any compound used to treat, ameliorate or prevent a disease or condition in a subject. In some embodiments herein, the drug is an anti-viral agent.

Effector molecule: The portion of an antibody conjugate (or immunoconjugate) that is intended to have a desired effect on a cell to which the conjugate is targeted. Effector molecules are also known as effector moieties, therapeutic agents, diagnostic agents, or similar terms. Therapeutic agents (or drugs) include such compounds as small molecules, nucleic acids, proteins, peptides, amino acids or derivatives, glycoproteins, radioisotopes, lipids, nanoparticles, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the effector molecule can be contained within an encapsulation system, such as a nanoparticle, liposome or micelle, which is conjugated to the antibody. Encapsulation shields the effector molecule from direct exposure to the circulatory system. Means of preparing liposomes attached to antibodies are well-known (see, for example, U.S. Pat. No. 4,957,735; and Connor et al., *Pharm Ther* 28:341-365, 1985). Diagnostic agents or moieties include radioisotopes and other detectable labels (e.g., fluorophores, chemiluminescent agents, and enzymes). Radioactive isotopes include $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

Epitope: An antigenic determinant. These are particular chemical groups or peptide sequences on a molecule that are antigenic, meaning that they elicit a specific immune response. An antibody specifically binds a particular antigenic epitope on a polypeptide.

Framework region: Amino acid sequences interposed between CDRs. The framework regions serve to hold the CDRs in an appropriate orientation for antigen binding.

Fusion protein: A protein comprising at least a portion of two different (heterologous) proteins. In some embodiments, the fusion protein includes a polypeptide (such as a single-domain monoclonal antibody) disclosed herein and a heterologous protein, such as an Fc protein.

Glycoprotein complex (GPC): An antigen expressed on the Lassa virus (LASV) surface. The form of GPC found on the LASV virion is a trimer of heterodimers, each containing GP1 (the receptor binding subunit) and GP2 (the transmembrane, fusion-mediating subunit). As the sole LASV surface antigen, GPC is the primary target of protective humoral immune responses (Hastie et al., *Science* 356, 923-928, 2017).

Heterologous: Originating from a separate genetic source or species. For example, a camel or shark antibody is heterologous to a human Fc protein.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of antigen-specific antibodies.

Immunoconjugate: A covalent linkage of an effector molecule to an antibody or functional fragment thereof. The effector molecule can be, for example, a detectable label, a photon absorber (such as IR700), or a toxin (to form an immunotoxin, such as an immunotoxin comprising *Pseudomonas* exotoxin or a variant thereof). Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. In one embodiment, an antibody is joined to an effector molecule. In another embodiment, an antibody joined to an effector molecule is further joined to a lipid or other molecule, such as to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule. The term "conjugated" or "linked" refers to making two polypeptides into one contiguous polypeptide molecule.

Immunoglobulin new antigen receptor (IgNAR) antibody: One of the three isotypes of immunoglobulin molecules produced by cartilaginous fish. IgNAR antibodies are homodimers of one variable new antigen receptor ($V_{NAR}$)

domain and five constant new antigen receptor ($C_{NAR}$) domains (Roux et al., *Proc Natl Acad Sci USA* 95:11804-11809, 1998). IgNAR antibodies are a major component of the immune system of cartilaginous fish.

Immunoliposome: A liposome with antibodies or antibody fragments conjugated to its surface. Immunoliposomes can carry cytotoxic agents or other drugs, such as anti-viral drugs, to antibody-targeted cells, such as virus-infected cells.

Isolated: An "isolated" biological component, such as a nucleic acid, protein (including antibodies) or organelle, has been substantially separated or purified away from other biological components in the environment (such as a cell) in which the component occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Lassa virus (LASV): A virus belonging to the genus Arenavirus, family Arenaviridae. Lassa virus has a segmented (two segments—small and large), single-stranded, ambisense RNA genome and a lipid envelope. The small genome segment encodes the nucleoprotein (NP) and the surface glycoprotein (GP) precursor. The large segment encodes a small zinc finger protein (Z) and an RNA polymerase (L). LASV is the causative agent of Lassa fever, which is endemic in Western Africa. Lassa fever is an acute viral hemorrhagic illness. Symptoms of Lassa fever include fever, weakness, cough, sore throat, headache and gastrointestinal illness.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label. The terms "conjugating," "joining," "bonding" or "linking" refer to making two polypeptides into one contiguous polypeptide molecule, or to covalently attaching a radionuclide, drug or other molecule to a polypeptide, such as an antibody or antibody fragment. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Neutralizing antibody: An antibody that reduces the infectious titer of an infectious agent by binding to a specific antigen on the infectious agent, such as a virus (e.g., LASV). In some embodiments, an antibody that is specific for a LASV GPC neutralizes the infectious titer of LASV. For example, an antibody that neutralizes LASV may interfere with the virus by binding it directly and limiting entry into cells. Alternately, a neutralizing antibody may interfere with one or more post-attachment interactions of the pathogen with a receptor, for example, by interfering with viral entry using the receptor. In some embodiments, an antibody that specifically binds to LASV GPC and neutralizes LASV inhibits infection of cells, for example, by at least 20%, by at least 30%, by at least 40%, by at least 50%, by at least 60%, by at least 70%, by at least 80% or by at least 90%, compared to a control antibody.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy,* $22^{nd}$ ed., London, UK: Pharmaceutical Press, 2013), describes compositions and formulations suitable for pharmaceutical delivery of the antibodies and other compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Photoimmunotherapy: A targeted therapy that utilizes an antigen-specific antibody-photoabsorber conjugate that can be activated by near-infrared light to kill targeted cells. The photon absorber is typically based on phthalocyanine dye, such as a near infrared (NIR) phthalocyanine dye (for example, IRDye® 700DX, also know known as IR700). The antibody (for example, a LASV-specific antibody) binds to the appropriate cell surface antigen (e.g., LASV GPC) and the photo-activatable dye induces lethal damage to cell membranes after NIR-light exposure. NIR-light exposure (e.g., 690 nm) induces highly selective, necrotic cell death within minutes without damage to adjoining cells (see, for example, U.S. Application No. 2018/0236076). Thus, such methods can be used to kill cells infected with a LASV, such as using the polypeptides provided herein.

Polypeptide: A polymer in which the monomers are amino acid residues joined together through amide bonds. When the amino acids are alpha-amino acids, either the L-optical isomer or the D-optical isomer can be used. The terms "polypeptide" and "protein" are used herein interchangeably and include standard amino acid sequences as well as modified sequences, such as glycoproteins. The term "polypeptide" is specifically intended to cover naturally occurring proteins, as well as proteins that are recombinantly or synthetically produced. In the context of the present disclosure, a "polypeptide" includes any protein or polypeptide (natural, recombinant or synthetic) that is capable of specific binding to a target antigen, such as a LASV GPC or portion thereof. Thus, the polypeptides disclosed herein can include at least one, such as one, two or three, CDR sequences that mediate specific binding to the target antigen. In some embodiments, the polypeptide is a single-domain monoclonal antibody, such as a camel single-domain monoclonal antibody or a shark $V_{NAR}$ single-domain monoclonal antibody, isolated from a phage display library, or a modified form thereof (such as a humanized or chimeric single-domain monoclonal antibody). In other embodiments, the polypeptide includes fibronectin (adectin), albumin, protein A (affibody), a peptide aptamer, an affimer, an affitin, an anticalin, or another antibody mimetic (see, e.g., Yu et al., *Annu Rev Anal Chem* 10(1): 293-320, 2017; Ta and McNaughton, *Future Med Chem* 9(12): 1301-1304, 2017; Koutsoumpeli et al., *Anal Chem* 89(5): 3051-3058, 2017), or a similar protein in which one or more CDR sequences have been incorporated to confer specific binding to the target antigen.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in viral load. "Ameliorating" refers to the reduction in the number or severity of signs or symptoms of a disease, such as a LASV infection.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein (such as a purified antibody) is at least 60%, 70%, 80%, 90%, 95% or 98% pure. Thus, in one specific, non-limiting example, a substantially purified protein is 90% free of other proteins or cellular components.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, which can be obtained from a subject or the environment. Examples include, but are not limited to, blood, serum, urine, semen, sputum, saliva, mucus, nasal wash, tissue, cells, tissue biopsy, fine needle aspirate, surgical specimen, feces, cerebral spinal fluid (CSF), bronchoalveolar lavage (BAL) fluid, nasopharyngeal samples, oropharyngeal samples, and autopsy material. Environmental samples include those obtained from an environmental media, such as water, air, soil, dust, wood, as well as samples obtained by wiping or swabbing a surface.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of an antibody that specifically binds a target antigen or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals such as birds, pigs, mice, rats, rabbits, sheep, horses, cows, dogs, cats and non-human primates).

Synthetic: Produced by artificial means in a laboratory, for example a synthetic nucleic acid or protein (for example, an antibody) can be chemically synthesized in a laboratory.

Therapeutically effective amount: The amount of agent, such as a polypeptide (e.g., a single-domain monoclonal antibody), that is sufficient to prevent, treat (including prophylaxis), reduce and/or ameliorate the symptoms and/or underlying causes of a disease or disorder, for example to prevent, inhibit, and/or treat a LASV infection. In some embodiments, a therapeutically effective amount is sufficient to reduce or eliminate a symptom of a disease, such as a LASV infection. For instance, this can be the amount necessary to inhibit or prevent viral replication or to measurably alter outward symptoms of the viral infection, such as fever, cough, headache, and sore throat. In general, this amount will be sufficient to measurably inhibit virus replication or infectivity.

In one example, a desired response is to inhibit or reduce or prevent a LASV infection. The LASV infection does not need to be completely eliminated or reduced or prevented for the method to be effective. For example, administration of a therapeutically effective amount of the agent can decrease the LASV infection (for example, as measured by infection of cells, or by number or percentage of subjects infected by LASV) by an amount, for example by at least 10%, at least 20%, at least 50%, at least 60%, at least 70%, at least 80%, at least 90%, at least 95%, at least 98%, or even at least 100% (elimination or prevention of detectable LASV infection, as compared to a suitable control).

A therapeutically effective amount of an agent can be administered in a single dose, or in several doses, for example daily, during a course of treatment. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Toxin: An agent that directly or indirectly inhibits the growth of and/or kills cells. Toxins include, for example, *Pseudomonas* exotoxin (PE, such as PE35, PE37, PE38 and PE40), diphtheria toxin (DT), botulinum toxin, abrin, ricin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Variable new antigen receptor ($V_{NAR}$): The single variable domain of the immunoglobulin new antigen receptor (IgNAR) antibody found in cartilaginous fish. $V_{NAR}$ antibodies are comprised of only two CDRs (CDR1 and CDR3), but also contain two other hypervariable (HV) regions, referred to as the HV2 and HV4 regions. The CDRs and HV regions are surrounded by framework regions (FR) in the following N-terminal to C-terminal order: FR1-CDR1-FR2-HV2-FR3a-HV4-FR3b-CDR3-FR4.

The $V_{NAR}$ domain, like other variable domains, has an immunoglobulin fold that contains β sheets held together by two canonical cysteine residues. In addition to the cysteines found in framework region (FR) 1 and 3b, the CDR3 can have one or two additional cysteines that form disulfide bonds with CDR1 or other framework regions. IgNAR are classified into four types based on the number and positioning of non-canonical cysteines in the $V_{NAR}$ domain. Type I $V_{NAR}$ domains contain two cysteine residues in CDR3 that form two extra disulfide bonds with FR2 and FR4. Type II $V_{NAR}$ domains have one non-canonical cysteine in CDR3 that forms a disulfide bond with a non-canonical cysteine in CDR1. Type III $V_{NAR}$ domains form a disulfide bond in CDR3 and FR2, and type IV domains have no additional disulfide bonds. While type I $V_{NAR}$ usually have flatter antigen binding regions and CDR3 regions that average 21 amino acids long, type II $V_{NAR}$ are usually shorter with an average of 15 amino acids and have a protruding CDR3 that enables binding to pockets and grooves (Barelle et al., *Adv Exp Med Biol* 655:49-62, 2009). The canonical CDR2 loop in classical IgG is missing in $V_{NAR}$ and is replaced with a short stretch of highly diverse amino acids, termed hypervariable region 2 (HV2) (Stanfield et al., *Science* 305:1770-1773, 2004). Additionally, there is a second hypervariable region, named HV4, which is inserted in the middle of FR3, therefore breaking FR3 into FR3a and FR3b.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other known genetic elements. In some embodiments, the vector is a virus vector, such as an AAV vector or lentivirus vector.

III. Polypeptides Specific for Lassa Virus Glycoprotein (GPC)

To identify antibodies for binding and neutralizing LASV, a stable soluble GPC trimer was designed, which has the amino acid sequence of SEQ ID NO: 8. The soluble GPC trimer, based on, but not identical to, the previously published GPCysR4 structure (PDB: 5VK2) (Hastie et al., *Science* 356, 923-928, 2017), was produced by appending a foldon trimerization domain at the C-terminus, and engineering an inter-protomer disulfide to stabilize the trimer. The proper conformation of this stabilized GPC trimer was confirmed by performing antigenicity tests with a panel of 10 human neutralizing antibodies, and by cryo-EM. Phage display technology was used to identify single domain antibodies from both the shark variable domain of new antigen receptors ($V_{NAR}$) (Feng et al., *Antib Ther* 2, 1-11, 2019; English et al., *Antib Ther* 3, 1-9, 2020) and camel single variable domain on heavy chain ($V_H$H) antibody libraries that bind the stabilized GPC trimer. Six single domain antibodies were identified that bound with high affinity toward the stabilized GPC trimer. Of them, single-domain $V_H$H antibody D5 was found to compete against the well-studied GPC-B neutralizing antibodies for binding toward GPC. Cryo-EM analysis showed that D5 approached from the top of the GPC trimer and sat at the apex hole. Upon binding, D5 altered the relative protomer orientation of the GPC trimer and, as a result, prevented GPC-B antibodies from binding. Moreover, D5 homodimer displayed efficient neutralization of LASV Josiah virus compared to monovalent single domain antibody D5, attributed to the avidity effect. Altogether, this demonstrates the development of a soluble stabilized LASV trimer and the identification of bivalent single domain antibodies displaying LASV neutralizing potency.

The amino acid sequences of the six LASV GPC-specific single-domain nanobodies (1 camel, 5 shark) selected from phage display libraries are provided below (and set forth herein as SEQ ID NOs: 1-6). The locations of the CDR sequences and hypervariable (HV) sequences (shark $V_{NAR}$ only) are indicated.

Camel $V_H$H CDR residues were determined according to IMGT (italics), Kabat (underlined) and Paratome (bold).

Camel $V_H$H D5

(SEQ ID NO: 1)

AWQLVESGGGSVQPGGSLTLTCQAS*KSTFSTS*

***G*MRWERQAQGKGVEFVAD*ISSDSTRKWY***SDSV

KGRFTISRSNWWRTVTLQMNDLKPEDTARYYC

*KDLESHHL*RGQGTQVTVSS

TABLE 1

| Positions of the CDRs in Camel $V_H$H D5 (SEQ ID NO: 1) | | | |
|---|---|---|---|
| Camel $V_H$H D5 | CDR1 | CDR2 | CDR3 |
| IMGT | 26-33 | 51-58 | 97-104 |
| Kabat | 31-35 | 50-66 | 97-104 |
| Paratome | 26-35 | 47-60 | 97-105 |

Shark $V_{NAR}$ are comprised of the following regions (N-terminal to C-terminal): FR1-CDR1-FR2-HV2-FR3a-HV4-FR3b-CDR3-FR4. CDRs (in bold) were determined using IMGT. HV2 and HV4 (underlined) were determined using annotation described in Stanfield et al., *Science* 305: 1770-1773, 2004; and Fennell et al., *J Mol Biol* 400:155-170, 2010.

Shark $V_{NAR}$ C3

(SEQ ID NO: 2)

ARVDQTPQTITAETGESLTINCVLRNSDCGLSDT

YWFRMSPGSGSEERISIGGRYLETVNSVSKSFSL

RINDLTVEDSGRYRCKTDVYRYVSGSGCLYSYFA

SGAGTVVTVN

Shark $V_{NAR}$ A1

(SEQ ID NO: 3)

ARVDQTPQTITKETGESLTINCVPPDSNCALADT

YWYRKKSGSTNEESISKGGRYVPTVNSGSKSFI

LRINDLRVADSGTYRCKVSCYAAAYYGQQLERLY

DVYGGGTAVTVN

Shark $V_{NAR}$ A10

(SEQ ID NO: 4)

ARVDQTPQTITKETGESLTITCILRDSQCALSPT

YWYHKKSGSTKPERIYKGGRYVETVNSGSKSFSL

-continued

RINDLTVEDSGTFFCKVSGWYAYSCRLEPDGYYD

VYGGGTVVTVN

Shark $V_{NAR}$ B8

(SEQ ID NO: 5)

ARVDQTPQTVTKETGESLTINCVLRDSNCALPST

YWYRKKSGSTNEENISKGGRYVETVNSGSKSFSL

RINDLRPEDSGTYRCKVHGLPLDCIPARGLELNW

REDVNGGGTAVTVN

Shark VNAR B10

(SEQ ID NO: 6)

ARVDQTPQTITKETGESLTINCVLRDSNCPLSS

TFWYRADAGSLNEENISKGGRYVETVNSGSKSF

SLRINDLTTEDSGTYRCKVAGLPLDCIPARGLE

LNWREDVYGGGTAVTVN

TABLE 2

| Positions of the CDRs and hypervariable regions of shark $V_{NAR}$ | | | | | | |
|---|---|---|---|---|---|---|
| $V_{NAR}$ | SEQ ID NO: | CDR1 | CDR2 | HV2 | HV4 | CDR3 |
| C3 | 2 | 26-33 | 45-49 | 45-52 | 60-64 | 84-102 |
| A1 | 3 | 26-33 | 45-49 | 45-52 | 60-64 | 84-103 |
| A10 | 4 | 26-33 | 45-49 | 45-53 | 60-64 | 84-103 |
| B8 | 5 | 26-33 | 45-49 | 45-52 | 60-64 | 84-106 |
| B10 | 6 | 26-33 | 45-49 | 45-52 | 60-64 | 84-106 |

Provided herein are polypeptides that bind (for example, specifically bind) LASV GPC. In some embodiments, the polypeptide is a monoclonal antibody, for example a single-domain antibody, such as a camel $V_H$H or shark $V_{NAR}$ antibody.

In some embodiments, the polypeptide (for example, single-domain monoclonal antibody) includes at least a portion of the amino acid sequence set forth herein as any one of SEQ ID NOs: 1-6, such as one or more (such as one, two or three) CDR sequences from any one of antibodies D5, C3, A1, A10, B8 or B10 (SEQ ID NOs: 1-6, respectively), as determined using any CDR numbering scheme (such as IMGT, Kabat, Paratome or Chothia, or any combination thereof; or using the annotation described in Stanfield et al. 2004 and/or Fennell et al. 2010 for shark $V_{NAR}$). In some examples, the polypeptide includes the CDR1, CDR2 and CDR3 sequences of SEQ ID NO: 1. In particular examples, the CDR sequences are determined using the Kabat, IMGT or Paratome numbering schemes, or a combination of the Kabat, IMGT and Paratome numbering schemes. In other examples, the polypeptide includes the CDR1 and CDR3 sequences of any one of SEQ ID NOs: 2-5. In particular examples, the CDR sequences are determined using IMGT. In specific non-limiting examples, the polypeptide further includes the HV2 and HV2 sequences of any one of SEQ ID NOs: 2-5.

In some embodiments, the polypeptide comprises the CDR1, CDR2 and CD3 sequences of D5 (SEQ ID NO: 1). In some examples, the CDR1, CDR2 and CDR3 sequences respectively comprise residues 26-33, 51-58 and 97-104 of SEQ ID NO: 1; residues 31-35, 50-66 and 97-104 of SEQ ID NO: 1; or residues 26-35, 47-60 and 97-105 of SEQ ID NO: 1.

In some examples, in addition to the CDR sequences, the polypeptide comprises one or more residues of D5 that contact the GPC trimer. Thus, in specific examples, the polypeptide comprises CDR1, CDR2 and CDR3 sequences respectively set forth as residues 26-33, 51-58 and 97-104 of SEQ ID NO: 1, and further comprises one or more of residues 1-3, 5, 20, 23-25, 35, 37, 45, 47, 50, 59-62, 74-78, 93, 95, 105 and 107 of SEQ ID NO: 1. In other specific examples, the polypeptide comprises CDR1, CDR2 and CDR3 sequences respectively set forth as residues 31-35, 50-66 and 97-104 of SEQ ID NO: 1, and further comprises one or more of residues 1-3, 5, 20, 23-30, 37, 45, 47, 74-78, 93, 95, 105 and 107 of SEQ ID NO: 1. In yet other specific examples, the polypeptide comprises CDR1, CDR2 and CDR3 sequences respectively set forth as residues 26-35, 47-60 and 97-105 of SEQ ID NO: 1, and further comprises one or more of residues 1-3, 5, 20, 23-25, 37, 45, 61, 62, 74-78, 93, 95 and 107 of SEQ ID NO: 1.

In other examples, the polypeptide comprises all of the D5 residues that contact the GPC trimer, which includes residues 1-3, 5, 20, 23-33, 35, 37, 45, 47, 50, 52, 53, 57-62, 74-78, 93, 95, 97, 99-105 and 107 of SEQ ID NO: 1.

In some examples, the amino acid sequence of the polypeptide is at least 80%, at least 85%, at least 90%, at least 95%, at least 96%, at least 97%, at least 98% or at least 99% identical to SEQ ID NO: 1. In particular examples, the polypeptide comprises the CDR1, CDR2 and CDR3 sequences of SEQ ID NO: 1 (determined using IMGT, Kabat, Chothia, Paratome or a combination thereof) and the remaining residues are at least 80%, at least 85%, at least 90%, at least 95%, at least 96%, at least 97%, at least 98% or at least 99% identical to SEQ ID NO: 1.

In another particular example, the polypeptide (such as a single-domain monoclonal antibody) comprises CDR1, CDR2 and CDR3 sequences respectively set forth as residues 26-33, 51-58 and 97-104 of SEQ ID NO: 1, and further comprises residues 1-3, 5, 20, 23-25, 35, 37, 45, 47, 50, 59-62, 74-78, 93, 95, 105 and 107 of SEQ ID NO: 1, wherein the remaining residues are at least 90% identical to SEQ ID NO: 1. In another particular example, the polypeptide (such as a single-domain monoclonal antibody) comprises CDR1, CDR2 and CDR3 sequences respectively set forth as residues 31-35, 50-66 and 97-104 of SEQ ID NO: 1, and further comprises residues 1-3, 5, 20, 23-30, 37, 45, 47, 74-78, 93, 95, 105 and 107 of SEQ ID NO: 1, wherein the remaining residues are at least 90% identical to SEQ ID NO: 1. In another specific example, the polypeptide (such as a single-domain monoclonal antibody) comprises CDR1, CDR2 and CDR3 sequences respectively set forth as residues 26-35, 47-60 and 97-105 of SEQ ID NO: 1, and further comprises residues 1-3, 5, 20, 23-25, 37, 45, 61, 62, 74-78, 93, 95 and 107 of SEQ ID NO: 1, wherein the remaining residues are at least 90% identical to SEQ ID NO: 1.

In specific examples, the amino acid sequence of the polypeptide comprises or consists of SEQ ID NO: 1.

In some embodiments, the polypeptide comprises the CDR1 and CD3 sequences of C3 (SEQ ID NO: 2). In some examples, the CDR1 and CDR3 sequences respectively comprise residues 26-33 and 84-102 of SEQ ID NO: 2. In some examples, the polypeptide further includes residues 45-52 (HV2) and 60-64 (HV4) of SEQ ID NO: 2. In some examples, the amino acid sequence of the polypeptide is at least 80%, at least 85%, at least 90%, at least 95%, at least 96%, at least 97%, at least 98% or at least 99% identical to SEQ ID NO: 2. In specific examples, the amino acid sequence of the polypeptide comprises or consists of SEQ ID NO: 2.

In some embodiments, the polypeptide comprises CDR1 and CD3 sequences of A1 (SEQ ID NO: 3). In some examples, the CDR1 and CDR3 sequences respectively comprise residues 26-33 and 84-103 of SEQ ID NO: 3. In some examples, the polypeptide further includes residues 45-52 (HV2) and 60-64 (HV4) of SEQ ID NO: 3. In some examples, the amino acid sequence of the polypeptide is at least 80%, at least 85%, at least 90%, at least 95%, at least 96%, at least 97%, at least 98% or at least 99% identical to SEQ ID NO: 3. In specific examples, the amino acid sequence of the polypeptide comprises or consists of SEQ ID NO: 3.

In some embodiments, the polypeptide comprises the CDR1 and CD3 sequences of A10 (SEQ ID NO: 4). In some examples, the CDR1 and CDR3 sequences respectively comprise residues 26-33 and 84-103 of SEQ ID NO: 4. In some examples, the polypeptide further includes residues 45-53 (HV2) and 60-64 (HV4) of SEQ ID NO: 4. In some examples, the amino acid sequence of the polypeptide is at least 80%, at least 85%, at least 90%, at least 95%, at least 96%, at least 97%, at least 98% or at least 99% identical to SEQ ID NO: 4. In specific examples, the amino acid sequence of the polypeptide comprises or consists of SEQ ID NO: 4.

In some embodiments, the polypeptide comprises the CDR1 and CD3 sequences of B8 (SEQ ID NO: 5). In some example, the CDR1 and CDR3 sequences respectively comprise residues 26-33 and 84-106 of SEQ ID NO: 5. In some examples, the polypeptide further includes residues 45-52 (HV2) and 60-64 (HV4) of SEQ ID NO: 5. In some examples, the amino acid sequence of the polypeptide is at least 80%, at least 85%, at least 90%, at least 95%, at least 96%, at least 97%, at least 98% or at least 99% identical to SEQ ID NO: 5. In specific examples, the amino acid sequence of the polypeptide comprises or consists of SEQ ID NO: 5.

In some embodiments, the polypeptide comprises the CDR1 and CD3 sequences of B10 (SEQ ID NO: 6). In some examples, the CDR1 and CDR3 sequences respectively comprise residues 26-33 and 84-106 of SEQ ID NO: 6. In some examples, the polypeptide further includes residues 45-52 (HV2) and 60-64 (HV4) of SEQ ID NO: 6. In some examples, the amino acid sequence of the polypeptide is at least 80%, at least 85%, at least 90%, at least 95%, at least 96%, at least 97%, at least 98% or at least 99% identical to SEQ ID NO: 6. In specific examples, the amino acid sequence of the polypeptide comprises or consists of SEQ ID NO: 6.

In some embodiments, the polypeptide is a single-domain monoclonal antibody. In some examples, the single-domain monoclonal antibody is a camel $V_HH$ single-domain antibody. In other examples, the single-domain monoclonal antibody is a shark $V_{NAR}$ single-domain antibody. In some examples, the single-domain monoclonal antibody is a humanized single-domain monoclonal antibody or a chimeric single-domain monoclonal antibody. In other examples, the polypeptide is a recombinant fibronectin or albumin.

Further provided herein are polypeptide (for example, antibody) compositions that include at least two, at least three, at least four, at least five, or six different polypeptides specific for LASV GPC. The polypeptides can each bind a separate epitope of GPC or can bind overlapping epitopes. In some embodiments, the polypeptide composition includes at least two polypeptides selected from a polypeptide having the CDR sequences of SEQ ID NO: 1, a polypeptide having the CDR sequence of SEQ ID NO: 2, a polypeptide having the CDR sequences of SEQ ID NO: 3, a polypeptide having the CDR sequences of SEQ ID NO: 4, a polypeptide having the CDR sequences of SEQ ID NO: 5 and a polypeptide having the CDR sequences of SEQ ID NO: 6. In some examples, the polypeptide compositions further include a pharmaceutically acceptable carrier.

Also provided are fusion proteins that include a LASV GPC-specific polypeptide (for example, antibody) disclosed herein and a heterologous protein. In some embodiments, the heterologous protein is an Fc protein or a leucine zipper. A single-domain antibody can be fused to an Fc region to generate a bivalent antibody ($V_H$H-Fc or $V_{NAR}$-Fc, see FIG. 4). In some examples, the Fc protein is a human Fc protein, such as the human IgG1 Fc. In particular non-limiting examples, the fusion protein includes a single-domain antibody disclosed herein, a hinge region (such as the llama IgG2a hinge sequence of SEQ ID NO: 7) and an Fc domain (such as the human IgG1 Fc domain). In one specific example, the fusion protein further includes a linker, such as an Ala-Ala-Ala linker located between the single-domain monoclonal antibody and the hinge region.

Also provided herein are chimeric antigen receptors (CARs) that include a polypeptide (such as a single-domain monoclonal antibody) disclosed herein. In some embodiments, the CAR further includes a hinge region, a transmembrane domain, a costimulatory signaling moiety, a signaling domain, or any combination thereof. In specific non-limiting examples, the hinge region comprises a CD8α hinge region, the transmembrane domain comprises a CD8α transmembrane domain, the costimulatory signaling moiety comprises a 4-1BB signaling moiety and/or the signaling domain comprises a CD3ζ signaling domain.

Also provided herein are GPC-specific polypeptides (for example, antibodies) modified to enable their use with a universal CAR system. In some embodiments, the GPC-specific polypeptide is fused to one component of a specific binding pair. In some examples, the antibody is fused to a leucine zipper or biotin.

Further provided are cells, such as immune cells or iPSCs, expressing a GPC-specific CAR. In some examples, the immune cell is a T cell, a natural killer cell, or a macrophage. In some examples, the immune cells are allogeneic cells, such as allogeneic cells obtained from a healthy donor. In specific non-limiting examples, the T cells are genetically modified to express the CAR and optionally to disrupt expression of the endogenous TCR. CARs and CAR-expressing cells are further described in section IV.

Also provided herein are immunoconjugates that include a polypeptide (for example, single-domain antibody) disclosed herein and an effector molecule. In some embodiments, the effector molecule is a toxin, such as, but not limited to, *Pseudomonas* exotoxin or a variant thereof, such as PE38. In other embodiments, the effector molecule is a detectable label, such as, but not limited to, a fluorophore, an enzyme or a radioisotope. In other embodiments, the effector molecule is a photon absorber, such as IR700. Immunoconjugates comprising a photon absorber can be used for photoimmunotherapy or in vivo diagnostic imaging. Immunoconjugates are further described in section V.

Further provided herein are antibody-drug conjugates (ADCs) that include a drug conjugated to a polypeptide (for example, single-domain antibody) disclosed herein. In some embodiments, the drug is a small molecule, for example an anti-viral agent, anti-microtubule agent, an anti-mitotic agent and/or a cytotoxic agent. In some examples, the anti-viral agent is ribavirin, remdesivir, galidesivir, arbidol, favipiravir, baricitinib, or lopinavir/ritonavir. ADCs are further described in section VI.

Also provided herein are multi-specific antibodies that include a polypeptide (for example, single-domain antibody) disclosed herein and at least one additional monoclonal antibody or antigen-binding fragment thereof. In some embodiments, the multi-specific antibody is a bispecific antibody. In other embodiments, the multi-specific antibody is a trispecific antibody. Multi-specific antibodies are further described in section VII.

Further provided herein are antibody-nanoparticle conjugates that include a nanoparticle conjugated to a polypeptide (for example, single-domain antibody) disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent or an anti-viral agent. In some examples, the anti-viral agent is ribavirin, remdesivir, galidesivir, arbidol, favipiravir, baricitinib, or lopinavir/ritonavir. Antibody-nanoparticle conjugates are further described in section VIII.

Further provided herein are nucleic acid molecules that encode a polypeptide, an antibody, fusion protein, CAR, immunoconjugate, or multiple-specific antibody disclosed herein. In some embodiments, the nucleic acid molecule is operably linked to a promoter. In some examples, the sequence of the nucleic acid molecule is at least 85%, at least 90%, at least 95%, at least 96%, at least 97%, at least 98%, at least 99% or 100% identical to SEQ ID NO: 9, which encodes antibody D5. Vectors that include the disclosed nucleic acid molecules are also provided. In some examples, the vector is an expression vector. In other examples, the vector is a viral vector. Isolated cells that include a nucleic acid molecule are vector disclosed herein are further provided. In some examples, the isolated cell is a prokaryotic cell, such as an *E. coli* cell. In other examples, the isolated cell is a mammalian cell, such as a human cell. Nucleic acid molecules are further described in section IX.

Compositions that include a pharmaceutically acceptable carrier and a polypeptide (for example, single-domain monoclonal antibody), fusion protein, CAR, isolated cell (such as a CAR expressing cell, for example a CAR T cell, a CAR NK cell, a CAR macrophage or a CAR iPSC), immunoconjugate, ADC, multi-specific antibody, antibody-nanoparticle conjugate, isolated nucleic acid molecule or vector disclosed herein are further provided by the present disclosure. In some examples, the composition includes a single-domain monoclonal antibody-Fc fusion protein (which forms a bivalent antibody, see FIG. 4). Compositions are further described in section X.

Also provided are methods of detecting LASV, or LASV GPC, in a sample, such as one obtained from a subject or the environment. In some embodiments, the method includes contacting the sample with a polypeptide (for example, antibody) disclosed herein and detecting binding of the polypeptide to the sample. Further provided are methods of detecting LASV in the environment. Further provided are methods of diagnosing a subject as having a LASV infection. In some embodiments, the method includes contacting a sample obtained from the subject with a polypeptide disclosed herein and detecting binding of the polypeptide to the sample, thereby diagnosing the subject as having a LASV infection. In some examples of these methods, the polypeptide is directly labeled. In other examples, the method includes contacting the polypeptide with a detection antibody, and detecting the binding of the detection antibody to the polypeptide, thereby detecting the LASV in the sample or diagnosing the subject as having a LASV infection. In some examples, the sample is obtained from a subject suspected of having a LASV infection.

Also provided herein are solid supports that include one or more of the LASV GPC-specific polypeptides disclosed herein. In some embodiments, the solid support comprises a bead, microchip, multiwell plate, or nitrocellulose having attached thereto one or more of the disclosed polypeptides (such as single-domain antibodies). Further provided is a method of detecting LASV in a sample that includes contacting the sample with the solid support having attached thereto one or more of the disclosed antibodies and detecting binding of the LASV to the one or more antibodies attached to the solid support, thereby detecting LASV in the sample. In some embodiments, the sample is an environmental sample or a biological sample obtained from a subject. In some examples, the environmental sample is a water, air, or soil sample, or a sample from a swabbed surface. Diagnostic and detection methods are further described in section XII.

Further provided are methods of treating a LASV infection in a subject. In some embodiments, the method includes administering to the subject a therapeutically effective amount of a polypeptide (for example, single-domain monoclonal antibody), fusion protein (such as a $V_H$H-Fc or $V_{NAR}$-Fc), CAR, isolated cell (such as a CAR-expressing immune cell, for example a CAR T cell, a CAR NK cell or a CAR macrophage), immunoconjugate, ADC, multi-specific antibody, antibody-nanoparticle conjugate, isolated nucleic acid molecule or vector disclosed herein, thereby treating the LASV infection. Therapeutic methods are further described in section XI.

IV. Chimeric Antigen Receptors (CARs)

The disclosed polypeptides, such as nanobodies, can also be used to produce CARs (also known as chimeric T cell receptors, artificial T cell receptors or chimeric immunoreceptors) and/or T lymphocytes (such as CTLs), natural killer (NK) cells or macrophages engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010; Dai et al., *J Natl Cancer Inst* 108(7):djv439, 2016). In some instances, the binding moiety is an antigen binding fragment of a monoclonal antibody, such as a scFv, or a single-domain antibody (for example, a camel or shark single-domain antibody). The spacer/hinge region typically includes sequences from IgG subclasses, such as IgG1, IgG4, IgD and CD8 domains. The transmembrane domain can be derived from a variety of different T cell proteins, such as CD3ζ, CD4, CD8 or CD28. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28, 4-1BB (CD137, TNFRSF9), OX-40 (CD134), ICOS, CD27 and/or DAP10.

Immune cells (such as T cells, NK cells or macrophages) or iPSCs expressing CARs can be used to target a specific cell type, such as a LASV-infected cell. Thus, the nanobodies disclosed herein can be used to engineer immune cells or iPSCs that express a CAR containing the LASV GPC-specific monoclonal antibody, thereby targeting the engineered immune cells or iPSCs to cells infected with LASV and thereby expressing LASV GPC.

Multispecific (such as bispecific) or bicistronic CARs are also contemplated by the present disclosure. In some embodiments, the multispecific or bispecific CAR includes a nanobody specific for LASV GPC and a monoclonal antibody specific for a different antigen (or a different epitope of GPC). Similarly, a bicistronic CAR includes two CAR molecules expressed from the same construct where one CAR molecule is a LASV GPC-targeted CAR and the second CAR targets a second antigen. See, for example, Qin et al., *Blood* 130:810, 2017; and WO/2018/213337.

Accordingly, provided herein are CARs that include a LASV GPC-specific antibody, such as any one of the nanobodies disclosed herein. Also provided are isolated nucleic acid molecules and vectors encoding the CARs (including bispecific and bicistronic CARs), and host cells, such as T cells, NK cells, macrophages or induced pluripotent stem cells (iPSCs) expressing the CARs, bispecific CAR or bicistronic CARs. T cells, NK cells, macrophages or iPSCs expressing CARs comprised of a LASV GPC-specific monoclonal antibody can be used for the treatment of a LASV infection. In some embodiments herein, the CAR is a bispecific CAR. In other embodiments herein, the CAR is a bicistronic CAR.

In some embodiments, the CAR includes a signal peptide sequence, for example, N-terminal to the antigen binding domain. The signal peptide sequence can be any suitable signal peptide sequence, such as a signal sequence from granulocyte-macrophage colony-stimulating factor receptor (GMCSFR), immunoglobulin light chain kappa, or IL-2. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

In some embodiments, the CARs disclosed herein are expressed from a construct (such as from a lentivirus vector) that also expresses a truncated version of human EGFR (huEGFRt). The CAR and huEGFRt are separated by a self-cleaving peptide sequence (such as T2A) such that upon expression in a transduced cell, the CAR is cleaved from huEGFRt (see, e.g., WO 2019/094482, which herein incorporated by reference).

The human epidermal growth factor receptor is comprised of four extracellular domains, a transmembrane domain and three intracellular domains. The EGFR domains are found in the following N-terminal to C-terminal order: Domain I-Domain II-Domain III-Domain IV-transmembrane (TM) domain-juxtamembrane domain-tyrosine kinase domain-C-terminal tail. Domain I and Domain III are leucine-rich domains that participate in ligand binding. Domain II and Domain IV are cysteine-rich domains and do not make contact with EGFR ligands. Domain II mediates formation of homo- or hetero-dimers with analogous domains from other EGFR family members, and Domain IV can form disulfide bonds with Domain II. The EGFR™ domain makes a single pass through the cell membrane and may play a role in protein dimerization. The intracellular domain includes the juxtamembrane domain, tyrosine kinase domain and C-terminal tail, which mediate EGFR signal transduction (Wee and Wang, *Cancers* 9(52), doi: 10.3390/cancers9050052; Ferguson, *Annu Rev Biophys* 37:353-373, 2008; Wang et al., *Blood* 118(5): 1255-1263, 2011).

A truncated version of human EGFR, referred to as "huEGFRt" includes only Domain III, Domain IV and the TM domain. Thus, huEGFRt lacks Domain I, Domain II, and all three intracellular domains. huEGFRt is not capable of binding EGF and lacks signaling activity. However, this molecule retains the capacity to bind particular EGFR-specific monoclonal antibodies, such as FDA-approved cetuximab (PCT Publication No. WO 2011/056894, which is herein incorporated by reference).

Transduction of T cells (or NK cells or macrophages) with a construct (such as a lentivirus vector) encoding both huEGFRt and a LASV GPC-specific CAR disclosed herein allows for selection of transduced cells using labelled EGFR monoclonal antibody cetuximab (ERBITUX™). For example, cetuximab can be labeled with biotin, and transduced cells can be selected using anti-biotin magnetic beads, which are commercially available (such as from Miltenyi Biotec). Co-expression of huEGFRt also allows for in vivo tracking of adoptively transferred CAR-expressing T cells (or NK cells or macrophages). Furthermore, binding of cetuximab to T cells expressing huEGFRt induces cytotoxicity of ADCC effector cells, thereby providing a mechanism to eliminate transduced T cells in vivo (Wang et al., *Blood* 118(5): 1255-1263, 2011), such as at the conclusion of therapy.

Also provided herein are LASV GPC-specific monoclonal antibodies (such as a nanobody disclosed herein) modified to enable their use with a universal CAR system. Universal CAR systems have been developed in order to increase CAR flexibility and expand their use to additional antigens. Currently, for each patient who receives CAR T cell therapy, autologous T cells must be cultured, expanded, and modified to express an antigen-specific CAR. This process is lengthy and expensive, limiting its use. Universal CARs are based on a system in which the signaling components of the CAR are split from the antigen-binding portion of the molecule, but come together using a "lock-key" system. For example, biotin-binding immune receptor (BBIR) CARs are comprised of an intracellular T cell signaling domain fused to an extracellular domain comprising avidin. Biotinylated antigen-specific (such as LASV GPC-specific) monoclonal antibodies can then bind the BBIR to direct T cells to antigen-expressing cells. Another example is the split, universal and programmable (SUPRA) CAR system. In the SUPRA system, the CAR includes the intracellular signaling domains fused to an extracellular leucine zipper, which is paired with an antigen-specific monoclonal antibody fused to a cognate leucine zipper. For a review of universal CAR systems, see, for example, Zhao et al., *J Hematol Oncol* 11(1): 132, 2018; and Cho et al., *Cell* 173:1426-1438, 2018. In some embodiments herein, the LASV GPC-specific monoclonal antibody is fused to one component of a specific binding pair. In some examples, the monoclonal antibody is fused to a leucine zipper or biotin.

Another type of universal CAR can be generated using a sortase enzyme. A sortase is a prokaryotic enzyme that modifies surface proteins by recognizing and cleaving a carboxyl-terminal sorting signal. Sortase catalyzes transpeptidation between a sortase recognition motif and a sortase acceptor motif. Thus, antigen-specific CARs can be generated by contacting an antigen-specific antibody fused to a sortase recognition motif with a portion of a CAR molecule that includes the intracellular signaling domain(s), a transmembrane region and an extracellular portion comprising a sortase acceptor motif. In the presence of the sortase enzyme, the two components become covalently attached to form a complete antigen-specific CAR. Accordingly, in some embodiments herein, a LASV GPC-specific monoclonal antibody is modified to include a sortase recognition motif (see, for example, PCT Publication No. WO 2016/014553).

In some embodiments, the GPC-targeted CAR is expressed in allogeneic T cells, NK cells, or macrophages, such as allogeneic T cells, NK cells or macrophages from a healthy donor(s). In some examples, the allogeneic T cells are genetically engineered to express the GPC-targeted CAR, for example by disrupting expression of the endogenous T cell receptor by insertion of the CAR (see, for example, MacLeod et al., *Mol Ther* 25(4): 949-961, 2017). Gene editing can be performed using any appropriate gene editing system, such as CRISPR/Cas9, zinc finger nucleases or transcription activator-like effector nucleases (TALEN).

In some embodiments, the GPC-targeted CAR is expressed in induced pluripotent stem cells (iPSCs).

V. Immunoconjugates

The disclosed single-domain monoclonal antibodies, such as any of SEQ ID NOS: 1, 2, 3, 4 5 or 6, can be conjugated to a therapeutic agent or effector molecule. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. It will be appreciated that therapeutic agents can include various drugs, such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}I$, $^{32}P$, $^{14}C$, $^{3}H$ and $^{35}S$, photon absorbers such as IR700, and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a LASV-infected cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of known means. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies, one skilled in the art will be able to determine a suitable method for attaching a given agent to an antibody or other polypeptide.

The antibodies disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a photon absorber, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide particles are also of use as labels. An antibody may also be labeled with a predetermined polypeptide epitope recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody disclosed herein can also be conjugated to a photon absorber. In some embodiments, the photon absorber is a phthalocyanine dye, such as, but not limited to, IRDye® 700DX (also known as "IR700"). Antibody-photoabsorber conjugates can be used for photoimmunotherapy (for example to kill cells infected with LASV).

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, MO). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264: 14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S.

Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32): 11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

The antibodies described herein can also be used to target any number of different diagnostic or therapeutic compounds to cells expressing LASV GPC on their surface (e.g., LASV-infected cells). Thus, an antibody of the present disclosure can be attached directly or via a linker to a drug that is to be delivered directly to cells expressing LASV GPC. This can be done for therapeutic, diagnostic or research purposes. Therapeutic agents include such compounds as nucleic acids, proteins, peptides, amino acids or derivatives, glycoproteins, radioisotopes, photon absorbers, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are known (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^{3}H$, $^{125}I$, $^{35}S$, $^{14}C$, or $^{32}P$), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are known. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Antibody-Drug Conjugates (ADCs)

Antibodies described herein can be part of an ADC. ADCs are compounds comprised of an antigen-specific antibody (such as a single-domain antibody or antigen-binding fragment of an immunoglobulin) and a drug, for example an anti-viral agent (such as remdesivir, galidesivir, arbidol, favipiravir, baricitinib, or lopinavir/ritonavir) or a cytotoxic agent (such as an anti-microtubule agent or cross-linking agent). Because ADCs are capable of specifically targeting cells expressing a particular antigen, the drug can be much more potent than agents used for standard systemic therapy. For example, the most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PBDs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody (or a nanobody-Fc fusion protein) is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with B1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as an anti-viral agent) conjugated to a monoclonal antibody that binds (such as specifically binds) LASV GPC. In some embodiments, the drug is a small molecule. In some examples, the drug is an anti-viral agent, such as remdesivir, galidesivir, arbidol, favipiravir, baricitinib, or lopinavir/ritonavir. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PBD, an auristatin, a maytansinoid, dolastatin, calicheamicin, nemorubicin and its derivatives, PNU-159682, anthracycline, *vinca* alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am Chem Soc,* 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PBD dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC includes an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12):3580-3584, 2001) and have anticancer (U.S. Pat. No. 5,663,149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC includes an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC includes an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a LASV infection alone or in combination with another therapeutic agent and/or in combination with any standard therapy for the treatment of a LASV infection, such as Lassa fever (e.g., remdesivir, galidesivir, lenzilumab, hydroxychloroquine, arbidol, favipiravir, baricitinib, lopinavir/ritonavir, Zinc ions, and interferon beta-1b).

VII. Multi-Specific Antibodies

Multi-specific antibodies are recombinant proteins comprised of two or more monoclonal antibodies (such as single-domain antibodies) or antigen-binding fragments of two or more different monoclonal antibodies. For example, bispecific antibodies are comprised of two different monoclonal antibodies or antigen-binding fragments thereof. Thus, bispecific antibodies bind two different antigens and trispecific antibodies bind three different antigens.

Provided herein are multi-specific, such as trispecific or bispecific, monoclonal antibodies comprising a first LASV GPC-specific monoclonal antibody. In some embodiments, the multi-specific monoclonal antibody further comprises a second nanobody that specifically binds a different epitope of LASV GPC or a different cell-surface antigen. Also provided are isolated nucleic acid molecules and vectors encoding the multi-specific antibodies, and host cells comprising the nucleic acid molecules or vectors. Multi-specific antibodies comprising a LASV GPC-specific antibody can be used for the treatment of a LASV infection. Thus, provided herein are methods of treating a subject with a LASV infection by administering to the subject a therapeutically effective amount of the LASV GPC-targeting multi-specific antibody.

VIII. Antibody-Nanoparticle Conjugates

The antibodies disclosed herein can be conjugated to a variety of different types of nanoparticles to deliver cytotoxic agents or anti-viral agents (such as remdesivir, galidesivir, arbidol, favipiravir, baricitinib, or lopinavir/ritonavir) directly to LASV-infected cells via binding of the antibody to GPC expressed on the surface of infected cells. The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, *Immunotherapy* 3(3):381-394, 2011).

Liposomes are common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine. Niosomes range from small, unilamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents, chemotherapeutic agents and other drugs.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core.

Polymeric micelles can be used to carry drugs that have poor solubility. These nanoparticles have been used to encapsulate a number of drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly (glycolic acids) (PGA), and poly(D,L-lactic-co-glycolic acid) (PLGA).

Antibodies provided herein can be conjugated to a suitable nanoparticle according to standard methods. For example, conjugation can be either covalent or non-covalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31) 5239-5277, 2012).

IX. Nucleic Acid Molecules

Nucleic acid molecules (for example, DNA, cDNA or RNA molecules) encoding the amino acid sequences of the disclosed polypeptides, antibodies, fusion proteins, and conjugates that specifically bind to LASV GPC, are provided. Nucleic acid molecules encoding these molecules can readily be produced using the amino acid sequences provided herein (such as the CDR sequences and the variable domain sequences), publicly available sequences (such as framework or constant region sequences), and the genetic code. In some embodiments, the nucleic acid molecules are expressed in a host cell (such as a mammalian cell or a bacterial cell) to produce a disclosed polypeptide, antibody, fusion protein or antibody conjugate (e.g., CAR, immunotoxin, multi-specific antibody).

In specific embodiments, the nucleic acid molecule encodes $V_H$H antibody D5. In some examples, the nucleic acid molecule is at least 80%, at least 85%, at least 90%, at least 95%, at least 96%, at least 97%, at least 98% or at least 99% identical to SEQ ID NO: 9. In specific examples, the nucleic acid molecule comprises or consists of SEQ ID NO: 9.

Camel $V_H$H D5 nucleic acid sequence (SEQ ID NO: 9)

```
GCGTGGCAGCTGGTGGAGTCTGGGGGAGGCTCGGTGCAGCCGGGG

GGCTCTCTGACACTCACCTGTCAAGCTTCCAAATCTACGTTCAGT

ACGTCCGGCATGCGGTGGGAGCGCCAGGCTCAAGGGAAGGGAGTG

GAATTTGTCGCAGATATTAGTAGTGATAGTACGAGGAAATGGTAT

TCAGACTCCGTGAAGGGCCGATTCACGATCTCCAGAAGCAACTGG

TGGAGGACGGTGACTCTACAGATGAACGATCTGAAACCTGAGGAC

ACGGCCCGTTATTATTGTAAAGATCTTGAGTCCCACCATCTACGG

GGCCAGGGGACCCAGGTCACCGTCTCCTCA
```

The genetic code can be used to construct a variety of functionally equivalent nucleic acid sequences, such as nucleic acids that differ in their sequence but which encode the same antibody sequence, or encode a conjugate or fusion protein including the nanobody sequence.

Nucleic acid molecules encoding the polypeptides, antibodies, fusion proteins, and conjugates that specifically bind to LASV GPC can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual,* $4^{th}$ ed., New York: Cold Spring Harbor Laboratory Press, 2012) and Ausubel et al. (Eds.) (*Current Protocols in Molecular Biology*, New York: John Wiley and Sons, including supplements).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as in bacterial, plant, yeast, insect and mammalian cells. The antibodies and conjugates can be expressed as individual proteins including the single-domain antibody (linked to an effector molecule or detectable marker as needed), or can be expressed as a fusion protein. Any suitable method of expressing and purifying antibodies and antigen binding fragments may be used; non-limiting examples are provided in Al-Rubeai (Ed.), *Antibody Expression and Production*, Dordrecht; New York: Springer, 2011).

One or more DNA sequences encoding the polypeptides, antibodies, fusion proteins, or conjugates can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells, for example mammalian cells, such as the COS, CHO, HeLa and myeloma cell lines, can be used to express the disclosed antibodies and antigen binding fragments. Methods of stable transfer, meaning that the foreign DNA is continuously maintained in the host, may be used.

The expression of nucleic acids encoding the antibodies and conjugates described herein can be achieved by operably linking the DNA or cDNA to a promoter (which is either constitutive or inducible), followed by incorporation into an expression cassette. The promoter can be any promoter of interest, including a cytomegalovirus promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, trp, lac, or lambda promoters, a ribosome binding site, and a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by any suitable method such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

Modifications can be made to a nucleic acid encoding an antibody described herein without diminishing its biological activity. Some modifications can be made to facilitate the cloning, expression, or incorporation of the antibody into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the polypeptides, antibodies, fusion proteins, and conjugates can be purified according to standard procedures, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The polypeptides, antibodies, fusion proteins, and conjugates need not be 100% pure. Once purified, partially or to homogeneity as desired, if to be used prophylactically, the antibodies should be substantially free of endotoxin.

Methods for expression of polypeptides, antibodies, fusion proteins, and conjugates, and/or refolding to an appropriate active form, from mammalian cells, and bacteria such as *E. coli* have been described and are applicable to the antibodies disclosed herein. See, e.g., Greenfield (Ed.), *Antibodies: A Laboratory Manual,* 2nd ed. New York: Cold Spring Harbor Laboratory Press, 2014, Simpson et al. (Eds.), *Basic methods in Protein Purification and Analysis: A Laboratory Manual*, New York: Cold Spring Harbor Laboratory Press, 2009, and Ward et al., *Nature* 341(6242): 544-546, 1989.

X. Compositions

Compositions are provided that include one or more of the disclosed polypeptides (such as monoclonal antibodies) that bind (for example specifically bind) LASV GPC in a carrier. Compositions that include fusion proteins (such as nanobody-Fc fusion proteins), ADCs, CARs (and immune cells expressing CARs), multi-specific (such as bispecific or trispecific) antibodies, antibody-nanoparticle conjugates, immunoliposomes and immunoconjugates are also provided, as are nucleic acid molecule and vectors encoding the antibodies or antibody conjugates. The compositions can be prepared in unit dosage form for administration to a subject. The amount and timing of administration are at the discretion of the treating clinician to achieve the desired outcome. The polypeptide, antibody, fusion protein, ADC, CAR, CAR-expressing cell, multi-specific antibody, antibody-nanoparticle conjugate, immunoliposome or immunoconjugate can be formulated for systemic or local administration.

In some embodiments, the composition includes more than one GPC-specific single-domain monoclonal antibody disclosed herein, such as 2, 3, 4 or 5 antibodies. In particular examples, the composition includes: a polypeptide (e.g., a single-domain monoclonal antibody) having the CDR sequences (CDR1, CDR2 and CDR3) of camel $V_HH$ nanobody D5 (SEQ ID NO: 1); a polypeptide having the CDR sequences (CDR1 and CDR3) of $V_{NAR}$ nanobody C3 (SEQ ID NO: 2); a polypeptide having the CDR sequences (CDR1 and CDR3) of nanobody A1 (SEQ ID NO: 3); polypeptide having the CDR sequences (CDR1 and CDR3) of $V_{NAR}$ nanobody A10 (SEQ ID NO: 4); a polypeptide having the CDR sequences (CDR1 and CDR3) of $V_{NAR}$ nanobody B8 (SEQ ID NO: 5); and/or a polypeptide having the CDR sequences (CDR1 and CDR3) of $V_{NAR}$ nanobody B10 (SEQ ID NO: 6).

The compositions for administration can include a solution of the polypeptide, antibody, fusion protein, ADC, CAR, CAR-expressing iPSC or immune cell (such as a T cell, NK cell or macrophage), multi-specific (such as bispecific or trispecific) antibody, antibody-nanoparticle conjugate, immunoliposome or immunoconjugate in a pharmaceutically acceptable carrier, such as an aqueous carrier. A variety of aqueous carriers can be used, for example, water, buffered saline and the like. These solutions are sterile and generally free of undesirable matter. These compositions may be sterilized by conventional sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary, and can be selected primarily based on fluid volumes, viscosities, body weight and the like in accordance with the particular mode of administration selected and the subject's needs.

A typical pharmaceutical composition for intravenous administration includes about 0.1 to 10 mg of polypeptide, such as an antibody (or fusion protein, ADC, CAR, multi-specific antibody, antibody-nanoparticle conjugate, or immunoconjugate), per subject per day. Dosages from 0.1 up to about 100 mg per subject per day may be used, particularly if the agent is administered to a secluded site and not into the circulatory or lymph system, such as into a body cavity or into a lumen of an organ. In some embodiments, the composition can be a liquid formulation including one or more antibodies in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml. Actual methods for preparing administrable compositions are known or apparent, and are described in more detail in such publications as *Remington: The Science and Practice of Pharmacy*, The University of the Sciences in Philadelphia, Editor, Lippincott, Williams, & Wilkins, Philadelphia, PA, $21^{st}$ Edition (2005).

The polypeptides and monoclonal antibodies disclosed herein can also be administered by other routes, including via inhalation or oral.

Polypeptides and antibodies (or antibody conjugates, or nucleic acid molecules encoding such molecules) may be provided in lyophilized form and rehydrated with sterile water before administration, although they are also provided in sterile solutions of known concentration. The antibody solution can be added to an infusion bag containing 0.9% sodium chloride, USP, and in some cases administered at a dosage of from 0.5 to 15 mg/kg of body weight. Considerable experience is available in the administration of antibody drugs, which have been marketed in the U.S. since the approval of RITUXAN™. Polypeptides, antibodies, Fc fusion proteins, ADCs, CARs (or CAR-expressing cells), multi-specific (such as bispecific or trispecific) antibodies, antibody-nanoparticle conjugates, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the polypeptide/antibody-based compositions disclosed herein. Various degradable and nondegradable polymeric matrices for use in controlled drug delivery are known (Langer, *Accounts Chem. Res.* 26:537-542, 1993). For example, the block copolymer, poloxamer 407, exists as a viscous yet mobile liquid at low temperatures but forms a semisolid gel at body temperature. It is an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

XI. Therapeutic Methods

Methods are disclosed herein for the inhibition of a LASV infection in a subject. The methods include administering to the subject a therapeutically effective amount (that is, an amount effective to inhibit the infection in the subject) of a disclosed polypeptide, antibody, fusion protein, ADC, CAR, CAR-expressing iPSC or immune cell (such as a T cell, NK cell or macrophage), multi-specific (such as bispecific or trispecific) antibody, antibody-nanoparticle conjugate, immunoliposome or immunoconjugate, or a nucleic acid encoding such an antibody or antibody conjugate, to a subject at risk of a LASV infection or having a LASV infection. The methods can be used pre-exposure or post-exposure.

The infection does not need to be completely eliminated or inhibited for the method to be effective. For example, the method can decrease the infection by at least 10%, at least 20%, at least 30%, at least 40%, at least 50%, at least 60%, at least 70%, at least 80%, at least 90%, at least 95%, at least 98%, at least 99%, or even 100% (elimination or prevention of detectable LASV infection) as compared to the LASV infection in the absence of the treatment or compared to treatment with a control antibody. In some embodiments, the subject can also be treated with an effective amount of an additional agent, such as an anti-viral agent, for example ribavirin.

In some embodiments, administration of a therapeutically effective amount of a disclosed polypeptide, antibody, fusion protein, ADC, CAR, CAR-expressing iPSC or immune cell (such as a T cell, NK cell or macrophage), multi-specific (such as bispecific or trispecific) antibody, antibody-nanoparticle conjugate, immunoliposome or immunoconjugate, or nucleic acid molecule or vector encoding such molecules, inhibits the establishment of an infection and/or subsequent disease progression in a subject, which can encompass any statistically significant reduction in activity (for example, virus replication) or symptoms of the LASV infection in the subject (such as fever).

Methods are disclosed herein for the reduction or inhibition of LASV replication in a subject, such a reduction of LASV replication by at least 10%, at least 20%, at least 30%, at least 40%, at least 50%, at least 60%, at least 70%, at least 80%, at least 90%, at least 95%, at least 98%, at least 99%, or even 100% (elimination or prevention of detectable LASV replication) as compared to the LASV replication in the absence of the treatment or compared to treatment with a control antibody. The methods include administering to the subject a therapeutically effective amount (that is, an amount effective to inhibit replication in the subject) of a disclosed polypeptide, antibody, antigen binding fragment, or a nucleic acid encoding such an antibody or antigen binding fragment, to a subject at risk of a LASV infection or having a LASV infection. The methods can be used pre-exposure or post-exposure.

Methods are disclosed for treating a LASV infection in a subject. Methods are also disclosed for reducing or preventing a LASV infection in a subject. These methods include administering one or more of the disclosed polypeptide, antibody, fusion protein, ADC, CAR, CAR-expressing iPSC or immune cell (such as a T cell, NK cell or macrophage), multi-specific (such as bispecific or trispecific) antibody, antibody-nanoparticle conjugate, immunoliposome or immunoconjugate, or nucleic acid molecule or vector encoding such molecules, or a composition including such molecules, as disclosed herein.

Polypeptides, such as antibodies and conjugates thereof, can be administered, for example, by intravenous infusion. Doses of the antibody or conjugate thereof can vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or conjugate can be from about 0.5 mg/kg to about 5 mg/kg, such as a dose of about 1 mg/kg, about 2 mg/kg, about 3 mg/kg, about 4 mg/kg or about 5 mg/kg. The antibody or conjugate is administered according to a dosing schedule determined by a medical practitioner. In some examples, the antibody or conjugate is administered weekly, every two weeks, every three weeks or every four weeks.

In some embodiments, a subject is administered DNA or RNA encoding a disclosed antibody to provide in vivo antibody production, for example using the cellular machinery of the subject. Any suitable method of nucleic acid administration may be used; non-limiting examples are provided in U.S. Pat. Nos. 5,643,578, 5,593,972 and 5,817, 637. U.S. Pat. No. 5,880,103 describes several methods of delivery of nucleic acids encoding proteins to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof.

In several embodiments, a subject (such as a human subject at risk of a LASV infection or having a LASV infection) is administered an effective amount of a viral vector that includes one or more nucleic acid molecules encoding a disclosed antibody. The viral vector is designed for expression of the nucleic acid molecules encoding a disclosed polypeptide (e.g., antibody), and administration of the effective amount of the viral vector to the subject leads to expression of an effective amount of the antibody in the subject. Non-limiting examples of viral vectors that can be used to express a disclosed antibody or antigen binding fragment in a subject include those provided in Johnson et al., *Nat. Med.,* 15(8):901-906, 2009 and Gardner et al., *Nature,* 519(7541):87-91, 2015, each of which is incorporated by reference herein in its entirety.

In one embodiment, a nucleic acid encoding a disclosed polypeptide, antibody, or conjugate thereof, is introduced directly into tissue. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

Single or multiple administrations of a composition including a disclosed polypeptide, antibody or antibody conjugate, or nucleic acid molecule encoding such molecules, can be administered depending on the dosage and frequency as required and tolerated by the patient. The dosage can be administered once, but may be applied periodically until either a desired result is achieved or until side effects warrant discontinuation of therapy. Generally, the dose is sufficient to inhibit a LASV infection without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized.

The LASV GPC-specific polypeptide, antibody, antibody conjugate, or nucleic acid molecule encoding such molecules, or a composition including such molecules, can be administered to subjects in various ways, including local and systemic administration, such as, e.g., by injection subcutaneously, intravenously, intra-arterially, intraperitoneally, intramuscularly, intradermally, or intrathecally. In some embodiments, the composition is administered by inhalation, such as by using an inhaler. In one embodiment, the polypeptide, antibody, antigen binding fragment, or nucleic acid molecule encoding such molecules, or a composition including such molecules, is administered by a single subcutaneous, intravenous, intra-arterial, intraperitoneal, intramuscular, intradermal or intrathecal injection once a day. The polypeptide, antibody, antigen binding fragment, bispecific antibody, conjugate, or nucleic acid molecule encoding such molecules, or a composition including such molecules, can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the polypeptide, antibody, antibody conjugate, or nucleic acid molecule encoding such molecules, or a composition including such molecules, over a pre-determined period. The osmotic pump or mini-pump can be implanted subcutaneously, or near a target site.

In one example, a LASV GPC-specific polypeptide provided herein is conjugated to IR700, and photoimmunotherapy is used to treat a LASV infection. For example, such a method can include administering to the subject with a LASV infection a therapeutically effective amount of one or more LASV GPC-specific antibody-IR700 conjugates, wherein the GPC-specific antibody specifically binds to GPC on infected cells. Following administration of the conjugate, irradiation is performed at a wavelength of 660 to 740 nm (such as 660 to 710 nm, for example, 680 nm) and at a dose of at least 1 J $cm^{-2}$, thereby treating the LASV infection in the subject. In some examples, the LASV infection is irradiated at a wavelength of 660 to 740 nm (such as 660 to 710 nm, for example, 680 nm) at a dose of at least 1 J $cm^{-2}$ (such as at least 1 J $cm^{-2}$, at least 4 J $cm^{-2}$, at least 10 J $cm^{-2}$, at least 50 J $cm^{-2}$, or at least 100 J $cm^{-2}$) thereby treating the LASV infection in the subject. In some examples, multiple rounds of treatment are performed, such as 2, 3, 4, 5, 6, 7, 8, 9 or 10 treatment cycles. In particular examples, a therapeutically effective dose of a GPC-specific antibody-IR700 conjugates is at least 0.5 milligram per 60 kilogram (mg/kg), at least 5 mg/60 kg, at least 10 mg/60 kg, at least 20 mg/60 kg, at least 30 mg/60 kg, at least 50 mg/60 kg, for example 0.5 to 50 mg/60 kg, such as a dose of 1 mg/60 kg, 2 mg/60 kg, 5 mg/60 kg, 20 mg/60 kg, or 50 mg/60 kg, for example when administered iv. In another example, a therapeutically effective dose of an GPC-specific antibody-IR700 conjugates is at least 10 μg/kg, such as at least 100 μg/kg, at least 500 μg/kg, or at least 500 μg/kg, for example 10 μg/kg to 1000 μg/kg, such as a dose of 100 μg/kg, 250 μg/kg, about 500 μg/kg, 750 μg/kg, or 1000 μg/kg, for example when administered i.p. In one example, a therapeutically effective dose of an GPC-specific antibody-IR700 conjugates is at least 1 μg/ml, such as at least 500 μg/ml, such as between 20 μg/ml to 100 μg/ml, such as 10 μg/ml, 20 μg/ml, 30 μg/ml, 40 μg/ml, 50 μg/ml, 60 μg/ml, 70 μg/ml, 80 μg/ml, 90 μg/ml or 100 μg/ml administered in a topical solution.

In some embodiments, the method of treating a LASV infection in a subject further includes administration of one or more additional agents to the subject. Additional agents of interest include, but are not limited to, anti-viral agents such as ribavirin, remdesivir, galidesivir, favipiravir, baricitinib, lopinavir/ritonavir, hydroxychloroquine, dexamethasone, arbidol, zinc ions, and interferon beta-1b, or their combinations.

In one embodiment, a kit is provided for preventing or treating LASV infection in a subject, which includes a LASV GPC-specific polypeptide, fusion protein, CAR, immunoconjugate, ADC, multi-specific antibody, antibody-nanoparticle conjugate, isolated nucleic acid molecule or vector disclosed herein. Such kits can include other reagents or materials, such as a device for administration of the therapeutic agent, such as a syringe or nebulizer. In some examples such kits include one or more additional therapeutic agents, such as an additional anti-viral agent, for example ribavirin.

XII. Methods for Diagnosis and Detection

Methods are also provided for the detection of the presence of LASV GPC in vitro or in vivo. For example, the disclosed nanobodies can be used for in vivo imaging to detect a LASV infection. To use the disclosed polypeptides (such as antibodies, such as any of SEQ ID Nos: 1 2, 3, 4, 5, or 6) as diagnostic reagents in vivo, the polypeptides are labelled with a detectable moiety, such as a radioisotope, fluorescent label, or positron emitting radionuclides. As one example, the nanobodies disclosed herein can be conjugated to a positron emitting radionuclide for use in positron emission tomography (PET); this diagnostic process is often referred to as immunoPET. While full length antibodies can make good immunoPET agents, their biological half-life necessitates waiting several days prior to imaging, which increases associated non-target radiation doses. Smaller, single domain antibodies/nanobodies, such as those disclosed herein, have biological half-lives amenable to same day imaging.

In some examples, the presence of a LASV GPC is detected in a biological sample from a subject and can be used to identify a subject with a LASV infection. The sample can be any sample, including, but not limited to, blood, serum, urine, semen, sputum, saliva, mucus, nasal wash, nasopharyngeal samples, oropharyngeal samples, tissue, cells, tissue biopsy, fine needle aspirate, surgical specimen, feces, cerebral spinal fluid (CSF), and bronchoalveolar lavage (BAL) fluid. Biological samples also include sections of tissues, for example, frozen sections taken for histological purposes. The method of detection can include contacting a cell or sample, with an antibody or antibody conjugate (e.g., a conjugate including a detectable marker) that specifically binds to LASV GPC, under conditions sufficient to form an immune complex, and detecting the immune complex (e.g., by detecting a detectable marker conjugated to the antibody or antigen binding fragment.

In one embodiment, the polypeptide, antibody or antigen binding fragment is directly labeled with a detectable marker. In another embodiment, the polypeptide/antibody that binds the LASAV GPC (the primary antibody) is unlabeled and a secondary antibody or other molecule that can bind the primary antibody is utilized for detection. The secondary antibody that is chosen is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, GPC can be assayed in a biological sample by a competition immunoassay utilizing GPC standards labeled with a detectable substance and an unlabeled antibody that specifically binds GPC. In this assay, the biological sample, the labeled GPC standards and the antibody that specifically binds GPC are combined and the amount of labeled GPC standard bound to the unlabeled antibody is determined. The amount of GPC in the biological sample is inversely proportional to the amount of labeled GPC standard bound to the antibody that specifically binds GPC.

The immunoassays and methods disclosed herein can be used for a number of purposes. In one embodiment, the antibody that specifically binds LASV GPC may be used to detect the production of GPC in cells in cell culture. In another embodiment, the antibody can be used to detect the amount of GPC in a biological sample, such as a sample obtained from a subject having or suspected or having a LASV infection.

In one embodiment, a kit is provided for detecting LASV GPC in a biological sample, such as a blood, serum, urine, semen, CSF, nasopharyngeal, oropharyngeal, sputum, or saliva sample. Kits for detecting a LASV infection can include a monoclonal antibody that specifically binds LASV GPC, such as any of the nanobodies disclosed herein. In a further embodiment, the antibody is labeled (for example, with a fluorescent, radioactive, or an enzymatic label). In some examples, the antibody is present on a solid support, such as a bead or multi-well plate. In some examples, the kit further includes a detectably labeled secondary antibody that permits detection of the antibody that specifically binds LASV GPC.

In one embodiment, a kit includes instructional materials disclosing means of use of an antibody that binds LASV GPC. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. The kits may additionally include materials to obtain a sample, such as a swab, syringe, needle, and the like. Such kits and appropriate contents are well-known.

In one embodiment, the diagnostic kit comprises an immunoassay. Although the details of the immunoassays may vary with the particular format employed, the method of detecting LASV GPC in a biological sample generally includes the steps of contacting the biological sample with an antibody which specifically reacts, under immunologically reactive conditions, to LASV GPC. The antibody is allowed to specifically bind under immunologically reactive conditions to form an immune complex, and the presence of the immune complex (bound antibody) is detected directly or indirectly.

The antibodies disclosed herein can also be utilized in immunoassays, such as, but not limited to radioimmunoassays (RIAs), ELISA, lateral flow assay (LFA), or immunohistochemical assays. The antibodies can also be used for fluorescence activated cell sorting (FACS), such as for identifying/detecting virus-infected cells. FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind GPC, as disclosed herein, can be used in these assays. Thus, the antibodies can be used in a conventional immunoassay, including, without limitation, ELISA, RIA, LFA, FACS, tissue immunohistochemistry, Western blot or immunoprecipitation. The disclosed nanobodies can also be used in nanotechnology methods, such as microfluidic immunoassays, which can be used to capture LASV, or exosomes containing LASV Suitable samples for use with a microfluidic immunoassay or other nanotechnology method, include but are not limited to, saliva, blood, and fecal samples. Microfluidic immunoassays are described in U.S. Patent Application No. 2017/0370921, 2018/0036727, 2018/0149647, 2018/0031549, 2015/0158026 and 2015/0198593; and in Lin et al., *JALA* June 2010, pages 254-274; Lin et al., *Anal Chem* 92: 9454-9458, 2020; and Herr et al., *Proc Natl Acad Sci USA* 104(13): 5268-5273, 2007, all of which are herein incorporated by reference).

The following examples are provided to illustrate certain particular features and/or embodiments. These examples should not be construed to limit the disclosure to the particular features or embodiments described.

EXAMPLES

Figures 2A, 2B:
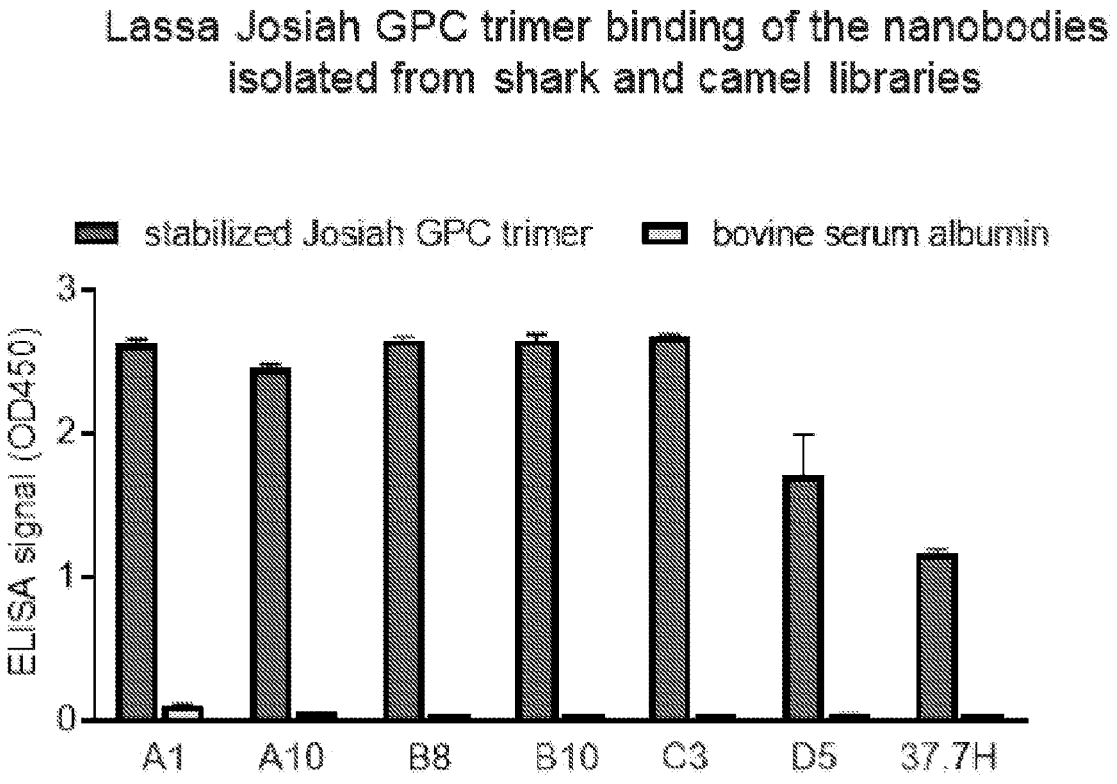
FIGS. 2A-2C: Nanobodies identified from camel and shark library panning bind stabilized LASV GPC trimer.
Figure 2C:
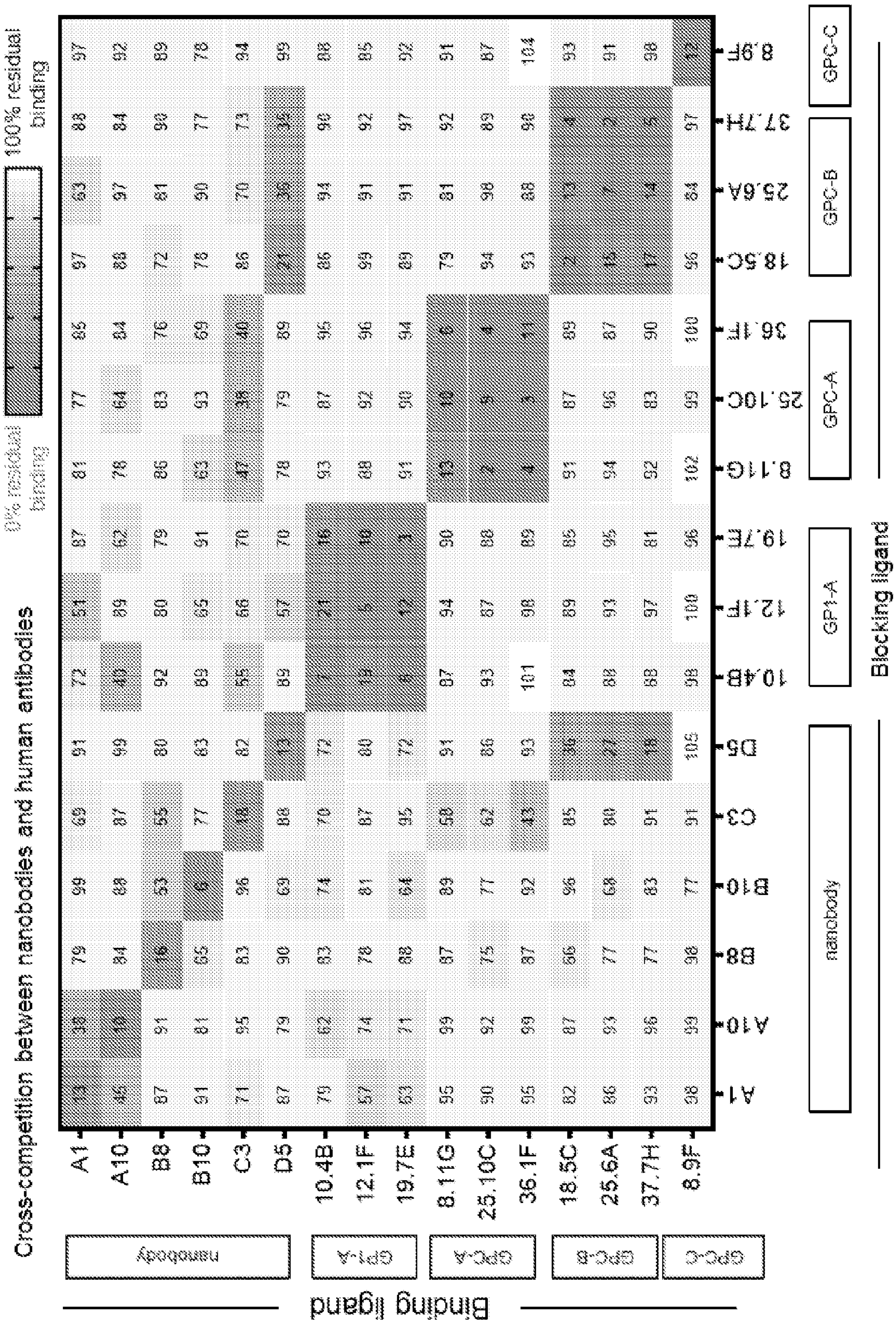

The LASV GPC trimer is metastable, conformationally labile, and heavily glycosylated, rendering the elicitation of neutralizing antibodies difficult (Cross et al., *Curr Opin Virol* 37, 97-104, 2019). Stabilization by a human neutralizing antibody 37.7H has enabled the structural analysis of the LASV GPC trimer (Hastie et al., *Science* 356, 923-928, 2017), yet a stabilized stand-alone GPC trimer has not been generated for use as immunogen. As disclosed in the following Examples, a structure-based design strategy was employed to engineer an inter-protomer disulfide bond and a foldon trimerization domain to stabilize the soluble, ligand-free LASV GPC trimer in its prefusion state, which demonstrated similar antigenicity and trimeric architecture as the previously published antibody-bound LASV GPC structure (FIG. 1A). Panning of this stabilized LASV GPC trimer against phage libraries identified several single domain antibodies that bound the stabilized trimer with high affinity (FIGS. 2A-2C). The studies in the Examples below illustrate that one single domain antibody (D5) bound a distinct site not readily accessible by an antibody Fab. Even without direct competition for the binding surface, D5 induced a substantial change of protomer angle within the GPC trimer to disable 37.7H binding (FIGS. 2A-2C and 4A-4C).

Figure 4A:
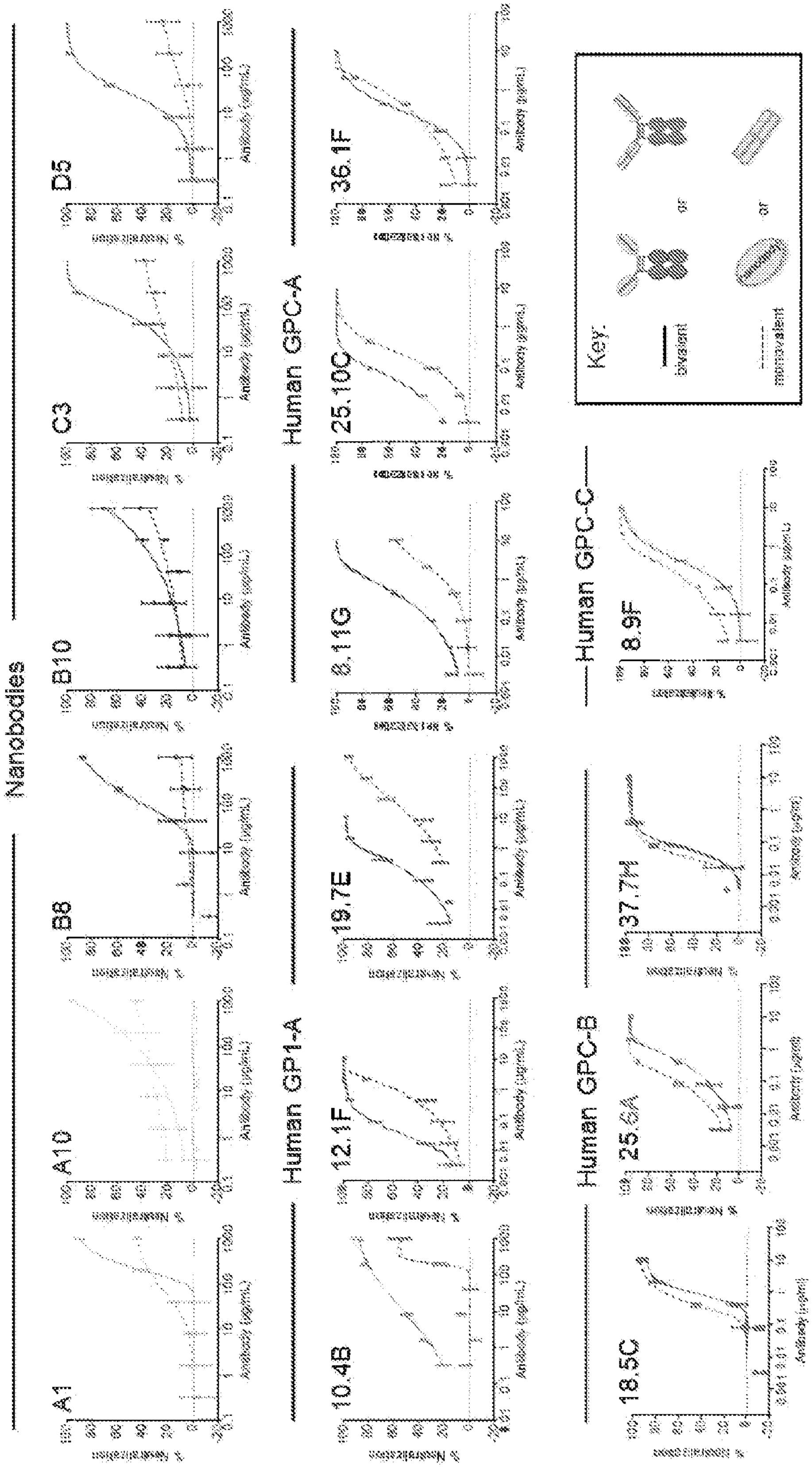

One of the key advantages of single domain antibodies over conventional antibodies is that they can be assembled into multimeric constructs to result in remarkable avidity. It is demonstrated in the Examples that linking two identical single domain antibodies by a Fc domain in a bivalent format exhibited improved neutralization of pseudotyped LASV Josiah strain, compared to the monovalent counterparts (FIGS. 4A-4C). By examining the neutralization profiles of monovalent versus bivalent single domain antibodies and Fab/antibodies, it was determined that avidity is important for efficient neutralization (FIGS. 4A-4C). This is distinct from the largest group of human LASV neutralizing antibodies (GPC-B), where a single Fab quaternarily contacts the interface between two protomers for locking the trimer in prefusion state to achieve neutralization (Hastie et al., *Science* 356, 923-928, 2017; Hastie et al., *Cell* 178, 1004-1015.e1014, 2019).

Although various animal model studies have shown that cellular immunity can occur in the absence of a humoral response to successfully protect treated animals from LASV infection (Fisher-Hoch et al., *J Virol* 74, 6777-6783, 2000; Carrion, Jr. et al., *Vaccine* 25, 4093-4102, 2007; Safronetz et al., *PLOS Negl Trop Dis* 9, e0003736, 2015), there are also concerns that cellular immunity may be associated with the pathogenesis of Lassa fever in some animal models (Oestereich et al., *PLOS Pathog* 12, e1005656, 2016; Ly, *Pathogens* 9(6):437, 2020; Flatz et al., *PLOS Pathog* 6, e1000836, 2010). Meanwhile, passive sera transfer therapy from Lassa fever survivors showing protection against disease and death in animals demonstrates that a humoral response plays an important role for disease prevention (Jahrling, *J Med Virol* 12, 93-102, 1983; Jahrling and Peters, *Infect Immun* 44, 528-533, 1984).

Example 1: Materials and Methods

This example describes the materials and experimental procedures for Examples 2-5.

Stabilized LASV GPC Trimer Sequence

The amino acid sequence of the stabilized LASV GPC trimer is provided below and set forth herein as SEQ ID NO: 8.

```
MGQIVTFFQEVPHVIEEVMNIVLIALSVLAVLKGLYNFATCGLVG

LVTFLLLCGRSCTTSLYKGVYELQTLELNMETLNMTMPLSCTKNN

SHHYIMVGNETGLELTLTNTSIINHKFCNLSDAHKKNLYDHALMS

IISTFHLSIPNFNQYEAMSCDENGGKISVQYNLSHSYAGDAANHC

GTVANGVLQTFMRMAWGGSYIALDSGGCGNWDCIMTSYQYLIIQN

TTWEDHCQFSRPSPIGYLGLLSQRTRDIYISRRRRGTFTWTLSDS

EGKDTPGGYCLTRWMLIEAELKCFGNTAVAKCNEKHDEEFCDMLR

LFDFNKQAIQRCKAPAQMSIQLINKAVNALINDQLIMKNHLRDIM

GIPYCNYSKYWYLNHTTTGRTSLPKCWLVSNGSYLNETHFSDDIE

QQADNMITEMLQKEGGGYIPEAPRDGQAYVRKDGEWVLLSTFLGG

LVPR
```

Structure-Based Design of Stabilized LASV GPC Trimer 152 design variants based on the published LASV GPC-37.7H complex crystal structure (PDB ID 5VK2) (Hastie et al., *Science* 356, 923-928, 2017) were made. In total, 68 disulfide bonds, 43 cavity-filling mutations, 22 helix-breaking mutations, and 19 trimerization domain insertions were designed (FIG. 1A).

Antigenic Screening of LASV GPC Stabilizing Designs

Initial assessment of all constructs was performed using high-throughput 96-well microplate expression format followed by an ELISA-based antigenic evaluation as described previously (McLellan et al., *Science* 342, 592-598, 2013). Briefly, $2.5\times10^5$ cells/ml of HEK 293T cells (Thermo Fisher Scientific, MA) were seeded in a 96-well microplate and cultured in expression medium (high glucose DMEM supplemented with 10% ultra-low IgG fetal bovine serum and 1×-non-essential amino acids) at 37° C., 5% $CO_2$ for 20 hours. Plasmid DNA and Turbo293 transfection reagent (Speed BioSystems) (Kwon et al., *Cell Rep* 22, 1798-1809, 2018) were then mixed and added to the cells. One day post transfection, enriched medium (high glucose DMEM plus 25% ultra-low IgG fetal bovine serum, 2× nonessential amino acids, 1× glutamine) was added to each well. The cells were cultured at 37° C. and 5% $CO_2$ for five additional days. Supernatants with the expressed LASV GPC variants were harvested and tested by ELISA for binding to 37.7H antibody using $Ni^{2+}$-NTA microplates.

Enzyme-Linked Immunosorbent Assay ELISA $Ni^{2+}$-NTA microplates (Pierce) were coated with 100 μl/well of the supernatant of LASV GPC variants at 4° C. overnight. After standard washing procedures with 0.1% Tween 20 in PBS, 100 μl of 10 μl/ml GPC-specific antibody 37.7H was added to the wells and incubated at room temperature for 2 hours. Next, 100 μl of horseradish peroxidase (HRP)-conjugated goat anti-human IgG Fc antibody (1:5000 v/v) (Jackson ImmunoResearch Laboratories Inc) was introduced to the plate for incubation at room temperature for 1 hour. Subsequently, plates were washed and then developed with 3,3',5,5'-tetramethylbenzidine (TMB) substrate (Kirkegaard & Perry Laboratories). Signal was read at 450 nm by a plate reader (Beckman Coulter).

LASV GPC Trimer Protein Expression and Purification

Disulfide and foldon-stabilized LASV GPC sequence was attached to a thrombin cleavage sequence, a hexahistidine tag, and a Strep-tag at its C-terminal end. The stabilized LASV GPC was expressed by transient transfection in 293F cells (Thermo Fisher) with Turbo293 transfection reagent (SPEED BioSystem) using the established protocol (Joyce et al., *Cell* 166, 609-623, 2016). Briefly, one liter of 293F cells at a density of $1.2\times10^6$ cells/ml were co-transfected with 700 μg/liter of the LASV GPC expression plasmid and 300 μg/liter of furin plasmid. Six days post transfection, the culture supernatant was harvested and protein was purified from the supernatants by Nickel-(Roche) and Strep-Tactin-(IBA Lifesciences) affinity columns. The resultant protein was loaded on a Superdex 200 16/600 size exclusion column (GE Healthcare) to be further polished for use in subsequent assays.

Production of Human LASV Antibodies

Immunoglobulin heavy chain or light chain sequences were constructed by gene synthesis and then cloned into human IgG1, lambda, or kappa expression plasmids as previously described (Tiller et al., *J Immunol Methods* 329, 112-124, 2008). Heavy and light chain expression plasmid DNA was transfected into Expi293F cells (Thermo Fisher) in 1:1 (v/v) ratio using Turbo293 transfection reagent (Kwon et al., *Cell Rep* 22, 1798-1809, 2018). Monoclonal antibodies from the culture supernatants were purified using recombinant Protein-A Sepharose (GE Healthcare) as per the manufacturer's instructions.

Antibody Fab Preparation

The purified human IgG proteins were cleaved by LysC enzyme (1:4000 w/w) (Roche) at 37° C. overnight to yield Fabs. On the next day, the enzymatic digestion reaction was terminated by addition of protease inhibitor (Roche). The cleavage mixture was then passed through a Protein-A column to separate the Fc fragments from the Fab. The Fab collected in the flow-through was loaded onto a Superdex 200 16/60 column for further purification.

LASV GPC Antigenic Characterization

An Octet Red384 instrument (fortéBio) was used to measure the binding kinetics between the stabilized LASV GPC trimers and human LASV neutralizing antibodies or nanobodies. Assays were performed at 30° C. in tilted black 384-well plates (Geiger Bio-One). Ni-NTA sensor tips (fortéBio) were used to capture the histidine-tagged stabilized LASV GPC trimer for 300 seconds. Then, the biosensor tips were equilibrated for 60 seconds in PBS before measurement of association with antigen-binding fragments (Fabs) in solution (6.25 nM to 400 nM) for 180 seconds. Subsequently, Fabs were allowed to dissociate for 300 seconds. Parallel correction to subtract systematic baseline drift was carried out by subtraction of the measurements recorded for a loaded sensor dipped in PBS. Data analysis and curve fitting were carried out using the Octet Data Analysis Software 9.0 (fortéBio). Experimental data were fitted with the binding equations describing a 1:1 interaction. Global analysis of the data sets assuming reversible binding (full dissociation) were carried out using nonlinear least-squares fitting allowing a single set of binding parameters to be obtained simultaneously for all of the concentrations used in each experiment.

Negative-Stain Electron Microscopy

The protein was diluted with a buffer containing 10 mM HEPES, pH 7.0, and 150 mM NaCl to a concentration of 0.02 mg/ml and adsorbed to a freshly glow-discharged carbon-coated copper grid. The grid was washed with the same buffer, and the adsorbed protein molecules were negatively stained with 0.7% uranyl formate. Micrographs were collected at a nominal magnification of 100,000 using SerialEM (Mastronarde, *J Struct Biol* 152, 36-51, 2005) on a FEI T20 electron microscope equipped with a 2k×2k Eagle camera and operated at 200 kV. The pixel size was 0.22 nm. Particles were picked automatically using in-house written software and extracted into 100×100-pixel boxes. Reference-free 2D classifications were performed using Relion (Scheres, *J Struct Biol* 180, 519-530, 2012).

Physical Stability of the Designed LASV GPC Trimer

To assess the physical stability of the designed LASV GPC trimer under various stress conditions, the proteins were treated with a variety of pharmaceutically relevant stresses such as extreme pH, high temperature, low and high osmolarity, and repeated freeze/thaw cycles while at a concentration of 50 μg/ml. The physical stability of treated LASV GPC trimer was evaluated by the preservation of binding to the GPC-specific antibody 37.7H. Temperature treatments were carried out by incubating the stabilized LASV GPC protein solutions at 50° C., 70° C. and 90° C. for 60 minutes in a PCR cycler with heated lid.

In pH treatments, the stabilized LASV GPC protein solution was adjusted to pH 3.5 and pH 10.0 with appropriate buffers for incubation at room temperature for 60 minutes and subsequently neutralized to pH 7.5. In osmolarity treatments, the stabilized LASV GPC protein solutions originally containing 150 mM NaCl were either diluted with 2.5 mM Tris buffer (pH 7.5) to an osmolarity of 10 mM NaCl or adjusted with 4.5 M $MgCl_2$ to a final concentration of 3.0 M $MgCl_2$. Protein solutions were incubated for 60 minutes at room temperature and then returned to 150 mM salt by adding 5.0 M NaCl or dilution with 2.5 mM Tris buffer, respectively, and concentrated to 50 μg/ml. The freeze/thaw treatment was carried out by repeatedly freezing the stabilized LASV GPC protein solutions in liquid nitrogen and thawing at 37° C. ten times. The degree of physical stability is reported as the ratio of steady state 37.7H antibody-binding level before and after stress treatment.

Phage Display Panning of Nanobody Libraries

Shark $V_{NAR}$ and camel $V_HH$ nanobody phage display libraries were previously constructed (Feng et al., *Antibody therapeutics* 2, 1-11, 2019). The phage panning protocol has been described previously (Ho et al., *J Biol Chem* 280, 607-617, 2005, Ho and Pastan, *Methods Mol Biol* 525, 293-308, xiv, 2009). Briefly, an immunotube (Nunc/Thermo Fisher Scientific, Rochester, NY) was coated with 0.5 ml of 10 μg/ml LASV GPC trimer in PBS at 4° C. overnight. After decanting the coating buffer, the immunotube was treated with 0.5 ml blocking buffer (10% milk in PBS) at room temperature for 1 hour. Then, a fixed amount of input phage from the shark or camel libraries was added to the immunotube for binding to the LASV GPC trimer at room temperature for 2 hours with gentle shaking. The immunotube was washed with PBS containing 0.05% Tween-20 to remove unbound phages. Subsequently, the bound phages were eluted with 100 mM triethylamine. At each round of panning, output phage enrichments were assessed and monitored by polyclonal phage ELISA. Single colonies were picked at the final round of panning for DNA sequencing. The binding ability of the identified nanobodies from phage display toward the stabilized LASV GPC trimer was further evaluated by ELISA, with bovine serum albumin (BSA) serving a negative control.

Polyclonal Phage ELISA

A 96-well plate (Corning) was coated with 50 μl/well of 5 μg/ml stabilized LASV GPC trimer in PBS buffer at 4° C. overnight. After blocking with 3% milk in 100% superblock buffer (Thermo Scientific) at room temperature for 2 hours, 50 μl phage were added to the plate and incubated at room temperature for another hour. Binding of phage to the stabilized LASV GPC was detected by HRP-conjugated anti-M13 antibody (GE Healthcare). The cut-off value for positive binder was set as 3× higher signal of antigen binding compared to background signal.

Expression of Nanobodies

Nanobody constructs C-terminally fused to a thrombin cleavage sequence, a hexahistidine tag, and a Flag-tag were synthesized (GeneImmune Biotechnology) and cloned into a pVRC8400 expression plasmid. Nanobodies were expressed as described above. Purification of nanobodies was performed using a Complete His-Tag Resin (Roche) by gravity flow. The resin was washed with three column volumes of PBS with 50 mM imidazole (Roche) and the target protein was subsequently eluted in three column volumes of PBS with 300 mM imidazole. The eluted protein was concentrated and loaded on a Superdex 200 16/60 size exclusion column (GE Healthcare).

Protein ELISA

Protein ELISA was used to evaluate the binding ability of the selected nanobody binders toward the stabilized LASV GPC trimer. Briefly, a 96-well plate was coated with either the stabilized LASV GPC trimer or BSA at 5 μg/ml in PBS, 50 μl/well, at 4° C. overnight. After blocking with 100% superblock buffer, the nanobodies were diluted into 1 μg/ml using 10% PBST in 100% superblock and then added to the plate for incubation at room temperature for 1 hour. Binding signal was detected by HRP-conjugated anti-Flag antibody (Sigma).

Cross-Competition Assay

The histidine- and Strep-tagged stabilized LASV GPC trimer protein (30 μg/ml) was captured by a mouse anti-streptavidin antibody, which was immobilized by the anti-mouse Fc sensor tips to a final mean signal level of 1.0-1.5 nm. The trimer-coated tips were then dipped into either PBS or the pre-determined saturating concentrations of Fabs (1000 nM) or nanobodies (500 nM) (first ligand) in PBS for 300 seconds. After loading, the sensor tips were incubated in PBS briefly for 60 seconds to remove unbound ligands for baseline adjustment. Subsequently, the sensor tips were dipped into wells containing a fixed concentration of competing ligands (second ligand, 1000 nM Fabs or 500 nM nanobodies) for another 300 seconds, followed by 300 seconds of dissociation in PBS. Raw data was processed using Octet Data Analysis Software 9.0. Percent of residual binding was calculated as follows: (response signal from the second ligand in presence of first ligand/response signal from the second ligand in absence of first ligand)×100.

Generation of Nanobody-IgG2a Proteins

To express the nanobodies in bivalent IgG format, the gene encoding the nanobody variable region was cloned into the mammalian protein expression vector pVRC8400 in front of DNA sequences encoding an Ala-Ala-Ala linker, the llama IgG2a hinge sequence (EPKIPQPQPKPQPQPQPQPKPQPKPEPECTCPKCP; SEQ ID NO: 7) and the human IgG1 Fc domain. The nanobody IgG2a proteins were expressed by transient transfection in 293F cells (Thermo Fisher) with Turbo293 transfection reagent (SPEED BioSystem) using the protocol described above and purified with protein A affinity column.

Production of Pseudovirus

Recombinant Indiana vesicular stomatitis virus (rVSV) expressing LASV GPC were generated as previously described (Nie et al., *Emerg Microbes Infect* 9, 680-686, 2020; Whitt, *J Virol Methods* 169, 365-374, 2010). HEK293T cells were grown to 80% confluency before transfection with plasmids expressing LASV Josiah GPC using FuGENE 6 (Promega). Cells were cultured at 37° C. with 5% $CO_2$ overnight. The next day, medium was removed and VSV-G pseudotyped ΔG-luciferase (G*AG-luciferase, Kerafast) was used to infect the cells in DMEM at a MOI of 3 for 1 hour before washing the cells with 1×DPBS three times. DMEM supplemented with 2% fetal bovine serum and 100 I.U./mL penicillin and 100 μg/mL streptomycin was added to the infected cells and they were cultured overnight as described above. On the following day, the supernatant was harvested and clarified by centrifugation at 300 g for 10 minutes before aliquoting and storage at −80° C.

Pseudovirus-Based Neutralization Assay

Neutralization assays were performed by incubating pseudoviruses with serial dilutions of antibodies and measured by the reduction in luciferase gene expression. In brief, Vero E6 cells (ATCC) were seeded in a 96-well plate at a concentration of $2\times10^4$ cells/well the day before. Pseudoviruses were incubated with serial dilutions of antibodies (six dilutions in a 5-fold step-wise manner) in triplicate at 37° C. for 30 minutes. Then, the mixture was added to cultured cells for infection and incubated for an additional 24 hours. The luminescence was measured by Britelite plus Reporter Gene Assay System (PerkinElmer). The 50% inhibitory concentration (IC50) was defined as the antibody concentration at which the relative light units (RLUs) were reduced by 50% compared with the virus control wells (virus+cells) after subtraction of the background RLUs in the control groups with cells only. The IC50 values were calculated with non-linear regression using GraphPad Prism 8 (GraphPad Software, Inc.).

Example 2: Structure-Based Design and Characterization of Stabilized LASV GPC Trimer As a type I viral fusion machine, the GPC trimer is metastable and can readily change from the prefusion conformation to the more stable post-fusion conformation (Li et al., *PLoS Pathog* 12, e1005418, 2016; Willard et al., *Pathogens* 8(1):1, 2018). Since the epitopes for most neutralizing antibodies are present only in the prefusion conformation of the trimer, stabilization of this conformation of the trimer was pursued. Using the structure of the prefusion LASV GPC (GPCysR4) in complex with 37.7H Fab (PDB: 5VK2) (Hastie et al., *Science* 356, 923-928, 2017) as a template, over 150 variants were designed and screened for high binding affinity to the GPC-specific antibody 37.7H. From these screening results, an engineered inter-protomer disulfide bond that links GP1 subunit of one protomer to the GP2 subunit of a neighboring protomer to yield improved antigenicity was identified. This inter-protomer disulfide, C207-L326C, replaced the existing intra-protomer disulfide C207-C360 present in GPCysR4 by introducing both a C360G mutation and a L326C mutation. Additionally, a Gly residue was inserted after position 206 (G206a) to allow the two Cys side chains to have optimal geometry for the formation of a $207C_{GP1}$-$L326C_{GP2}$ inter-protomer disulfide bond (FIG. 1A). To further stabilize the trimeric conformation of the LASV GPC, a T4-fibritin (foldon) trimerization domain was appended at the C-terminus to fix the protein base (FIG. 1A).

Figure 1B:
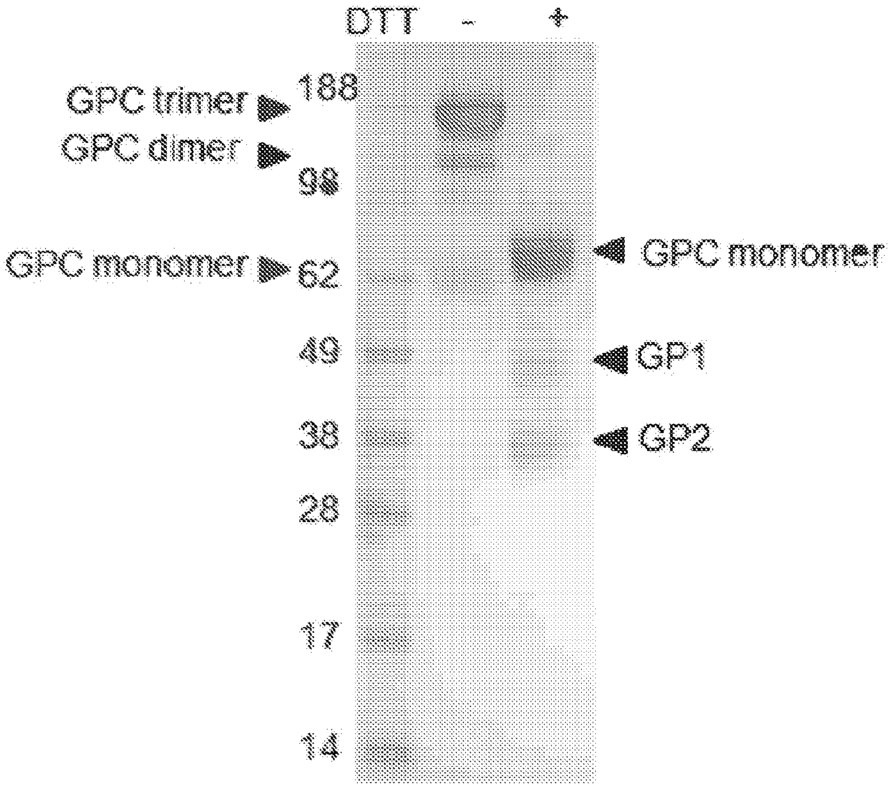
Figure 1C:
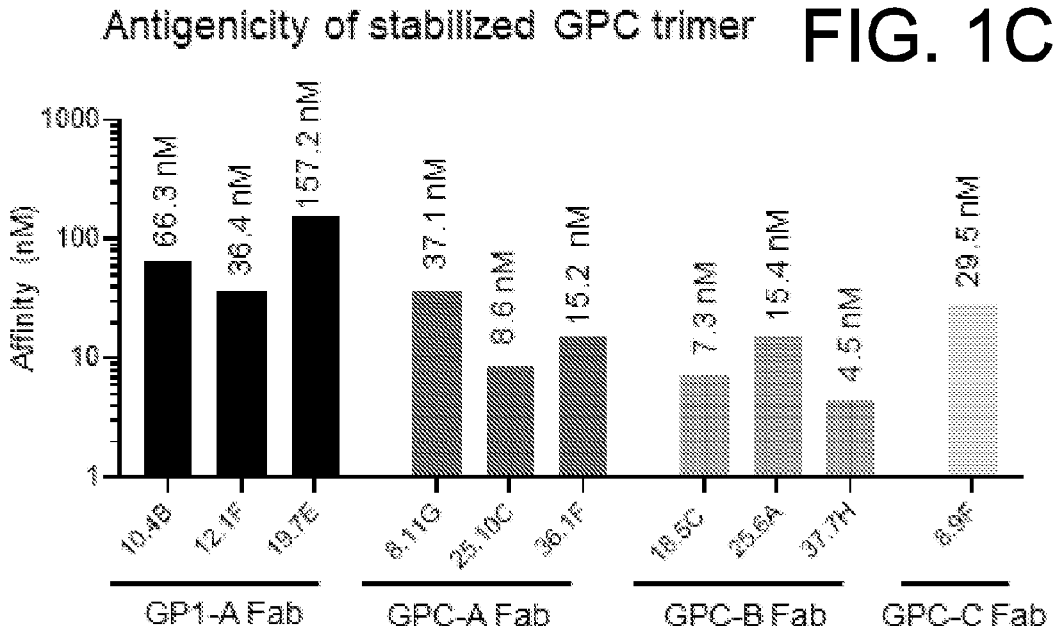
Figure 1D:
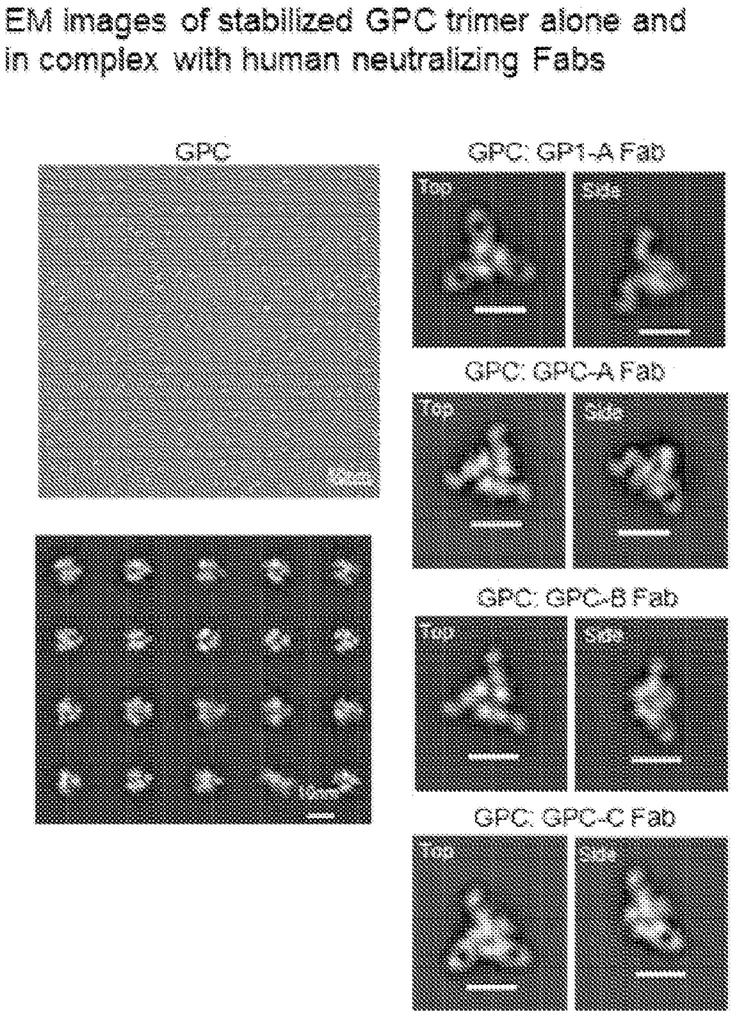
Figure 1E:
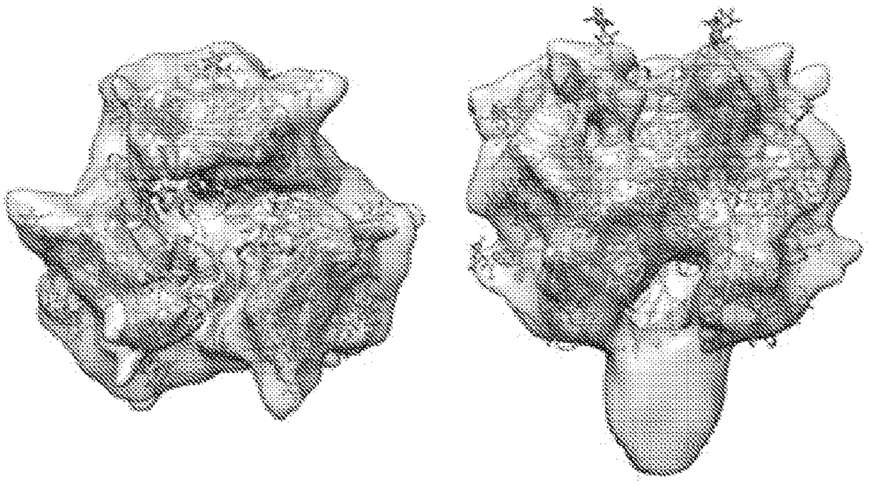
Figure 1F:
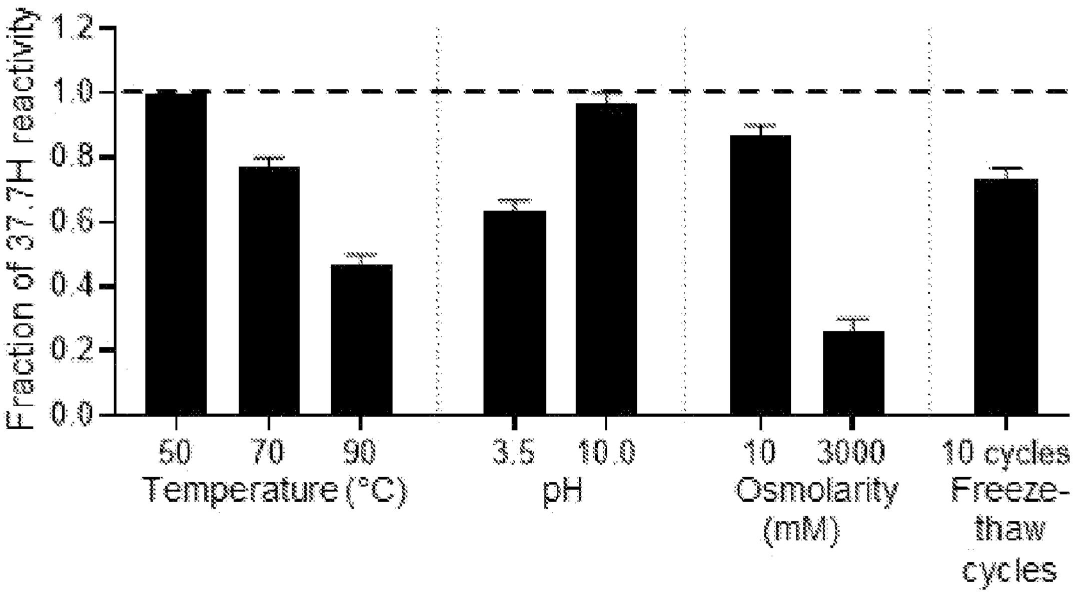

The resultant LASV GPC trimer expressed as a soluble protein with a final yield of approximately 0.5 mg/L by transient transfection of mammalian cells (FIG. 6B). The purified protein gave a major band at an expected size of a trimer (~200 kDa) on SDS-PAGE in the absence of reducing agent, indicative of the formation of an inter-protomer disulfide bond (FIG. 1B). Yet, the stabilized trimer was not efficiently cleaved into GP1 and GP2 subunits (FIG. 1B). Therefore, studies were performed to validate the stabilized LASV GPC trimer in several parameters. First, bio-layer interferometry (BLI) was employed to demonstrate that the stabilized GPC trimer could be recognized by a panel of 10 human LASV neutralizing antibodies from four epitope groups, which would indicate that the resultant trimer possessed similar antigenic properties as the previously published GPCysR4 construct (Hastie et al., *Science* 356, 923-928, 2017) (FIG. 1C). The stabilized trimer disclosed herein differs from the previously published GPCysR4 construct in that the disclosed GPC trimer is trimeric in the absence of 37.7H (or similar) antibody, whereas the GPCysR4 construct is monomeric unless incubated with a 37.7H-class antibody. Second, the homogeneous size and shape expected for a stable trimer in prefusion conformation of this stabilized GPC protein was confirmed by negative-stain electron microscopy (EM) (FIG. 1D). Importantly, in the presence of different human neutralizing Fabs, the stabilized trimer preserved its association without observable conformational distortion (FIG. 1D). To further examine the overall architecture of the inter-protomer disulfide-stabilized LASV GPC trimer, a cryo-EM structure was determined at 4.5 Å resolution from 230,534 particles (FIG. 1E). Although the engineered disulfide was not clearly seen in the map, the reconstruction density fit well in the LASV prefusion 5VK2 coordinate (Hastie et al., *Science* 356, 923-928, 2017) with RMSD <1.3 Å (FIG. 6). Lastly, physical stability tests were carried out to ensure the stabilized GPC trimer could withstand stresses under various temperature (50° C.-90° C.), pH (pH3.5 and pH10), osmolarity (10 mM and 3000 mM salt concentration), and freeze-thaw conditions, as evidenced by the retained 37.7H reactivity (Hastie et al., *Science* 356, 923-928, 2017) after treatment (FIG. 1F). Overall, the prefusion-stabilized LASV GPC trimer was shown to exhibit antigenic and structural characteristics consistent with the previously published antibody-bound LASV GPC trimer (Hastie et al., *Science* 356, 923-928, 2017) and therefore is a suitable probe for phage-display library panning.

Example 3: Identification of LASV GPC-Binding Single Domain Antibodies from Camel and Shark Libraries To identify single domain antibodies capable of binding the stabilized LASV GPC trimer, phage display libraries of the variable domain of new antigen receptor ($V_{NAR}$) antibodies from sharks (Feng et al., *Antib Ther* 2, 1-11, 2019; English et al., *Antib Ther* 3, 1-9, 2020) and single variable domain heavy chain ($V_H$H) antibodies from camels (Muyldermans, *J Biotechnol* 74, 277-302, 2001) were screened. After four consecutive rounds of panning, phage was enriched by 400-1200-fold for binding the stabilized LASV GPC trimer (FIGS. 7A-7D). At the end of the fourth round of panning, six individual clones (A1, A10, B8, B10, C3 from shark $V_{NAR}$, and D5 from camel $V_H$H) were identified that exhibited enhanced binding to stabilized LASV GPC trimer in ELISA, whereas no binding was observed between these single domain antibodies and the control protein bovine serum albumin (FIG. 2A). The binding affinities of these single domain antibodies to the stabilized GPC trimer were in the range of 15-45 nM as measured by BLI (FIG. 2B; FIG. 10A). To map where the single domain antibodies bound, their binding toward GP1 and GP2 subunit proteins were assessed. The results showed that five single domain antibodies (A1, A10, B8, B10 and D5) bound GP1 while C3 bound GP2 (FIG. 2B; FIG. 10B). It was next tested whether these six select single domain antibodies were able to compete for binding to GPC with four known groups of human LASV neutralizing antibodies, including GP1-A, GPC-A, GPC-B, and GPC-C(Hastie et al., *Science* 356, 923-928, 2017). Single domain antibodies A1, A10, B8 and B10 showed mild competition with the human neutralizing antibodies for binding the GPC trimer. In addition, C3 and D5 could compete with GPC-A and GPC-B antibodies, respectively (FIG. 2C).

Figure 3A:
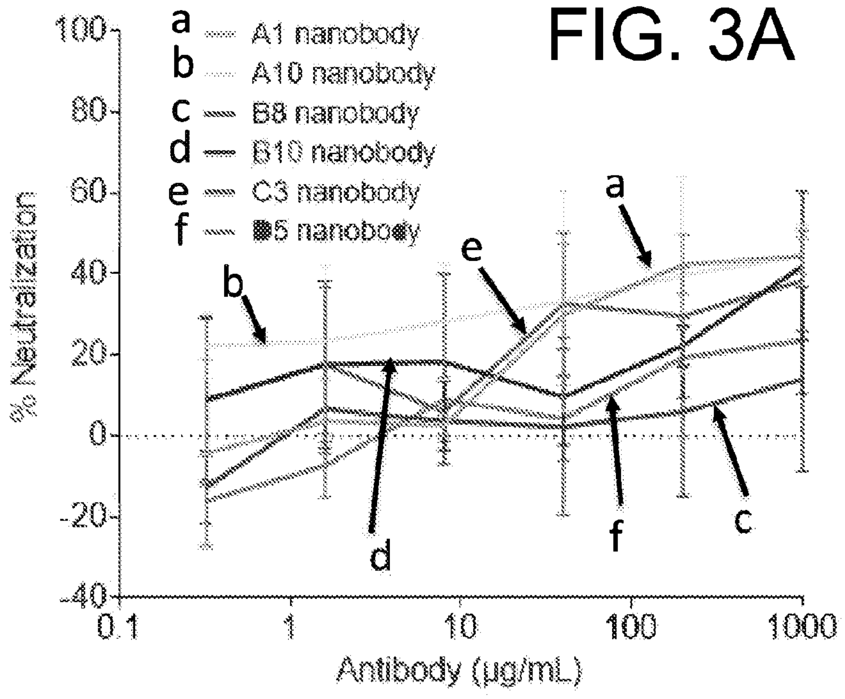
Figure 3B:
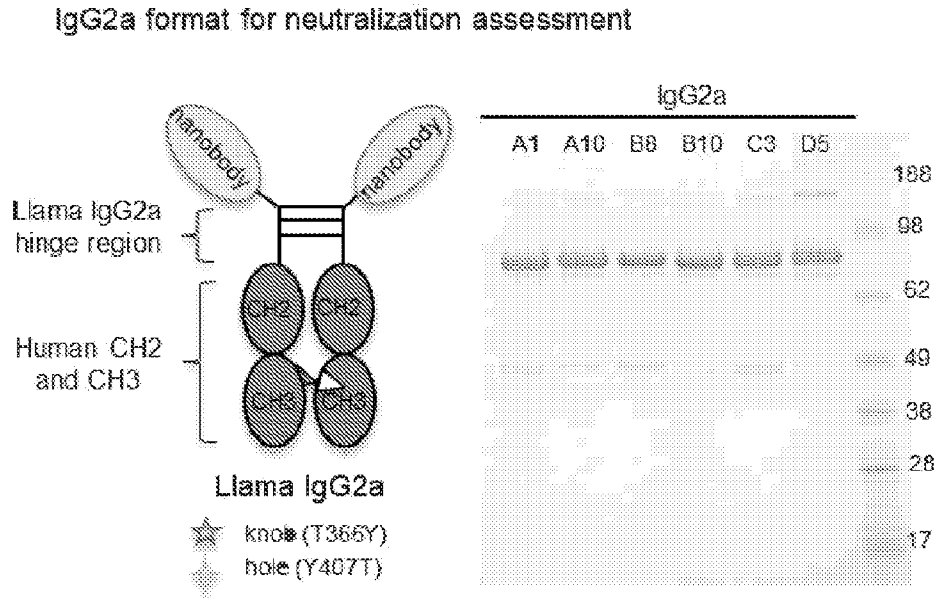

Example 4: Superior LASV Neutralization by Single Domain Antibody-IgG2a and Most Human Neutralizing Antibodies, Except the Quaternary-Specific GPC-B Group, Attributed to Avidity Additional studies were performed to explore whether the leading single domain antibodies could neutralize LASV pseudotyped Josiah virus. At the tested concentration range (1 μg/ml-1 mg/ml), all six single domain antibodies exhibited <50% neutralization (FIG. 3A). Since improved neutralization potency with multimeric single domain antibodies has been reported for different viruses (Wichgers Schreur et al., *Elife* 9:e52716, 2020; Koenig et al., *Science* 371 (6530):eabe6230, 2021; Boruah et al., *PLOS One* 8, e71383, 2013), a tail-to-tail fusion of two single domain antibody molecules connected by a llama IgG2a hinge region to the Fc domain of human IgG1 engineered with knob-into-hole mutation (Ridgway et al., *Protein Eng* 9, 617-621, 1996; Henry et al., *Immunogenetics* 71, 307-320, 2019) was constructed (FIG. 3B). Five out of six of the bivalent IgG2a antibodies exhibited modest neutralization toward the Josiah pseudovirus with $IC_{50}$ ranging from 12 to 260 μg/ml (FIG. 3C). Of these, the bivalent format of the single domain antibody D5 demonstrated the best neutralizing activity with $IC_{50}$ of 12 μg/ml (FIG. 3C). Binding kinetics of bivalent versus monovalent nanobodies toward GPC trimer is shown in FIG. 3D.

To delineate the molecular mechanism for LASV neutralization by single domain antibody-IgG2a, the neutralization potencies of the single domain antibodies and the human neutralizing antibodies were compared in monovalent and bivalent context for the pseudotyped Josiah virus. All six single domain antibodies in the monovalent format failed to neutralize, but when they were placed in a bivalent IgG2a format, five exhibited LASV neutralizing activities (FIG. 4A, top panel). Such a trend was similar to the human GP1-A and GPC-A groups of antibodies, for which higher neutralization potency was observed in bivalent IgGs than in monovalent Fabs (FIG. 4A, middle panel), but was opposite to the human GPC-B and GPC-C groups of antibodies, where better neutralization abilities were observed in monovalent Fabs than bivalent IgGs (FIG. 4A, bottom panel). Although the neutralization potencies of the bivalent single domain antibody-IgG2a were weaker than the human neutralizing antibodies (FIG. 4B), this is the first study reporting the identification of non-human neutralizing antibodies in vitro. It was reasoned that single domain antibody-IgG2a as well as human GP1-A and GPC-A antibodies mediate neutralization via avidity (Klein et al., *Proc Natl Acad Sci USA* 106, 7385-7390, 2009; Einav, *Cell Syst* 9, 466-474.e467, 2019), a different mechanism convergently employed by the most common group of LASV GPC-B group, where a single GPC-B Fab was able to bind and engage two protomers in a quaternary manner (FIG. 4C).

Figure 5A:
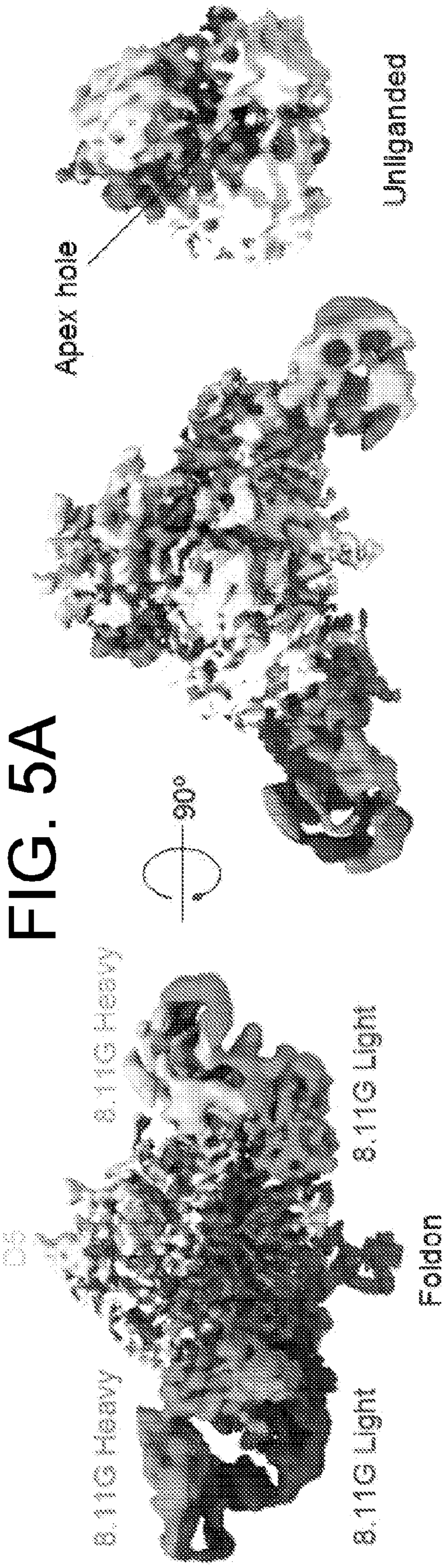
FIGS. 5A-5F: Structure of D5 with Lassa virus trimer reveals apex binding by D5 to alter protomer angle within trimer.
Figure 5B:
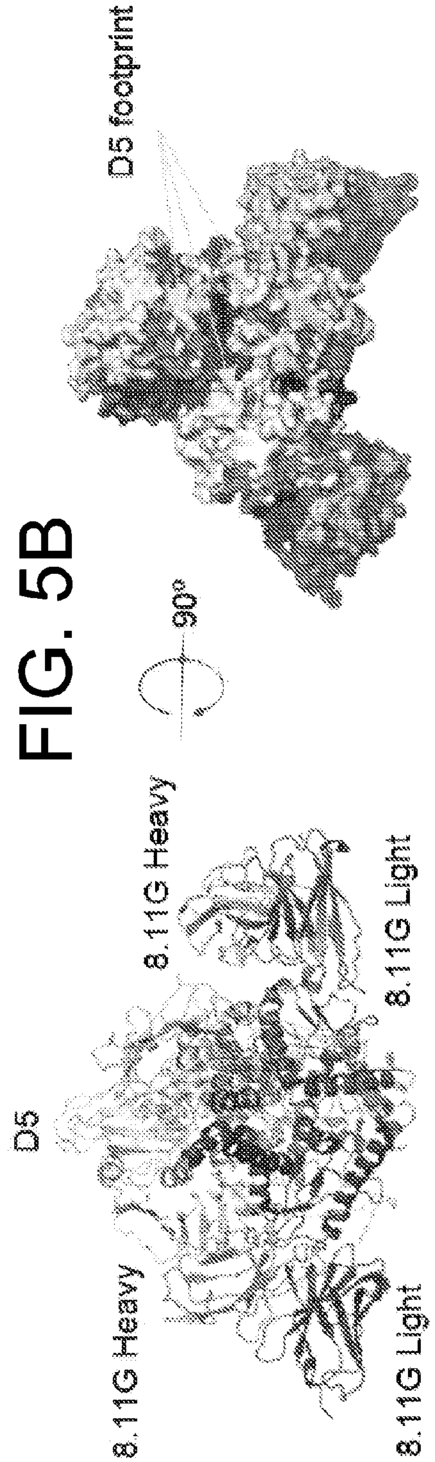
Figure 5C:
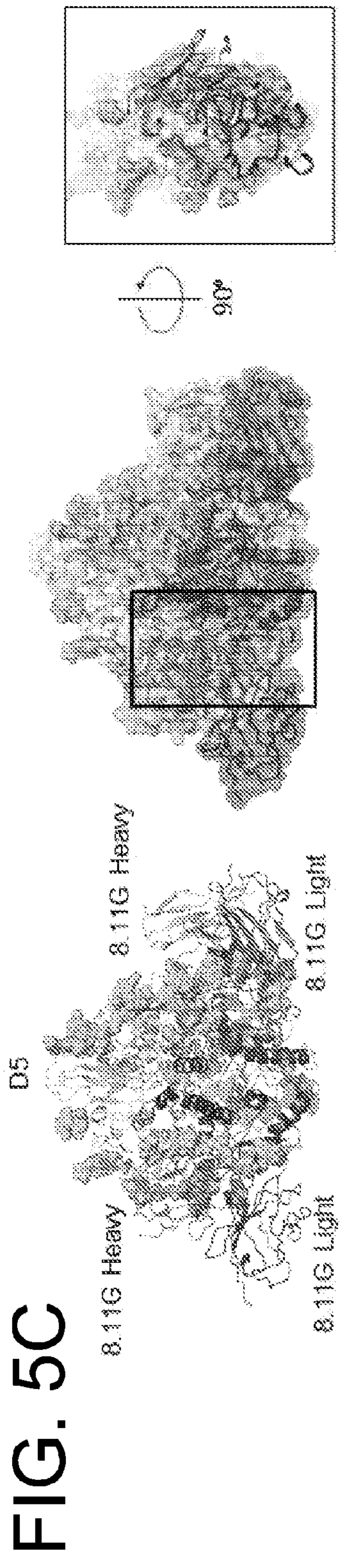

Example 5: Cryo-EM Structure of LASV GPC in Complex with Nanobody D5 and 8.11G Fab A structural study was performed to visualize the binding of D5 to GPC. It was not possible to interpret cryo-EM images of D5 bound to GPC, but the addition of human GPC-B 8.11G led to better resolved reconstructions, and the cryo-EM structure of prefusion-stabilized LASV GPC trimer in complex with a single D5 nanobody and two GPC-A 8.11G Fabs was determined at 4.7 Å. understand the molecular mechanism for the binding competition observed between D5 and GPC-B antibodies, a cryo-EM structure of D5 in complex with the GPC-A 8.11G Fab-bound GPC trimer was determined at 4.3 Å (FIG. 5A, FIGS. 8A-8D and FIG. 9). D5 bound to at the apex of the GPC trimer forming asymmetric interactions with all three GPC protomers (FIG. 5B). 8.11G bound to an interface between GP1 and GP2 subunits of single protomer (FIG. 5C). Despite the heavy glycosylation of GPC 8.11G navigated through the shield, making contact with six glycans.

Figure 5D:
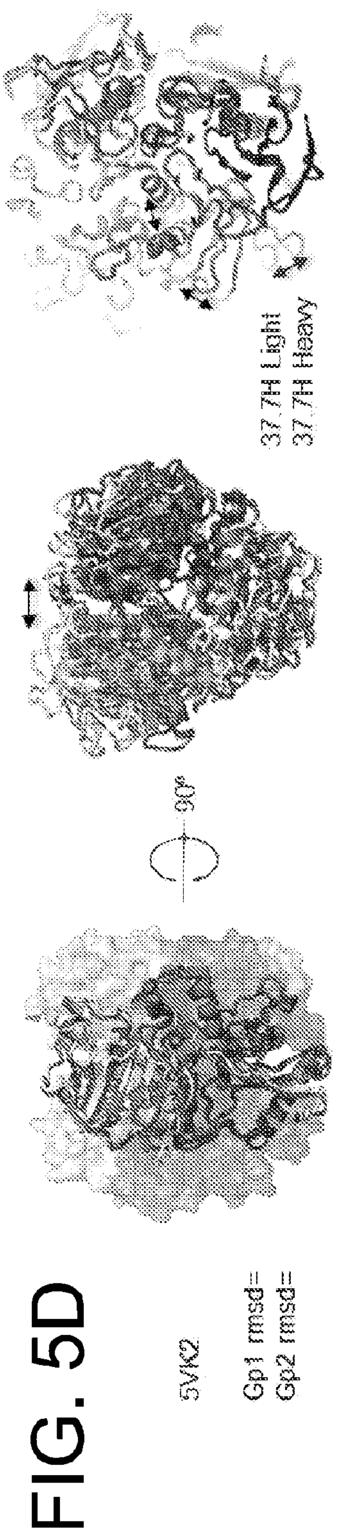
Figures 5E, 5F:
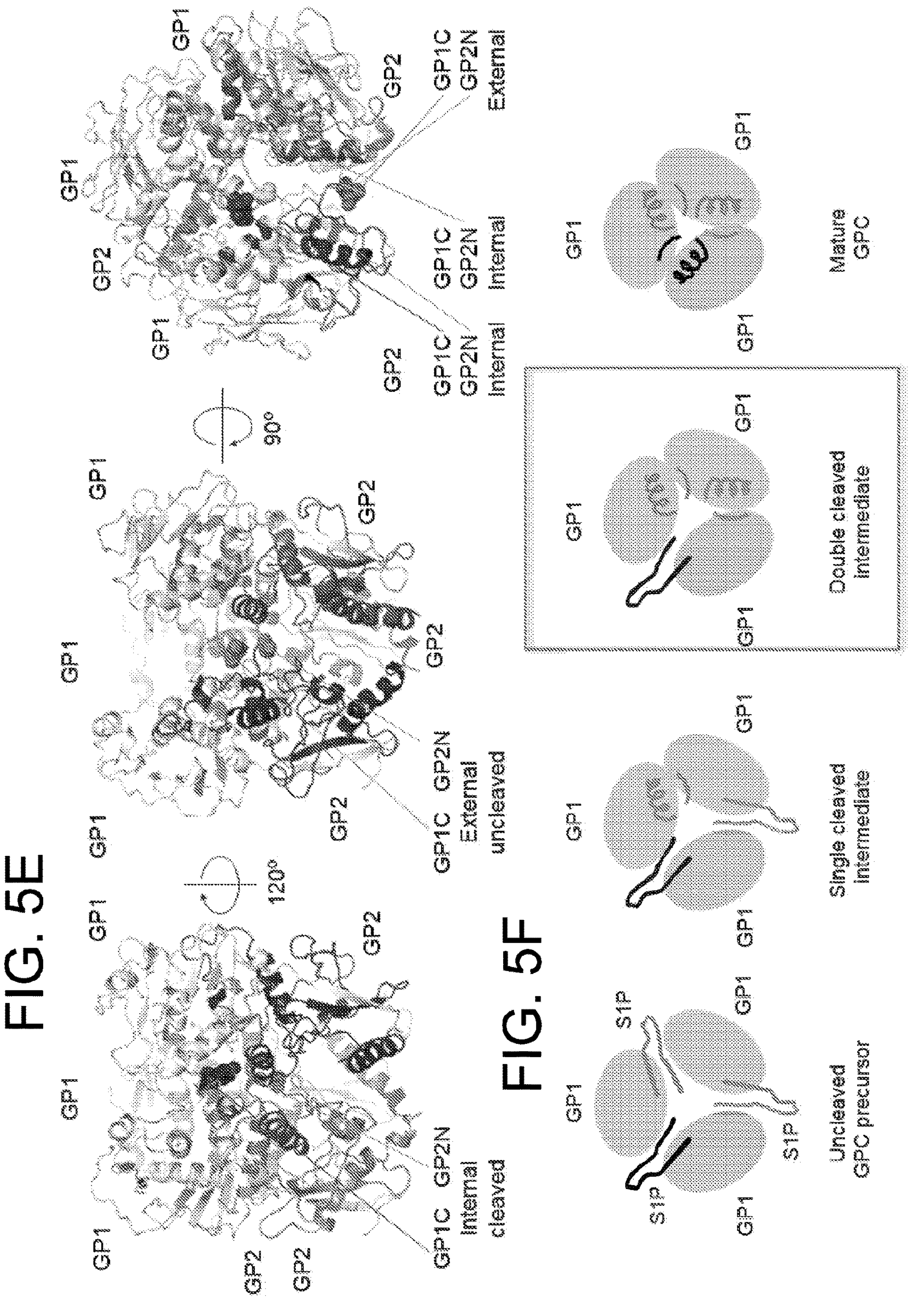
Figure 7A:
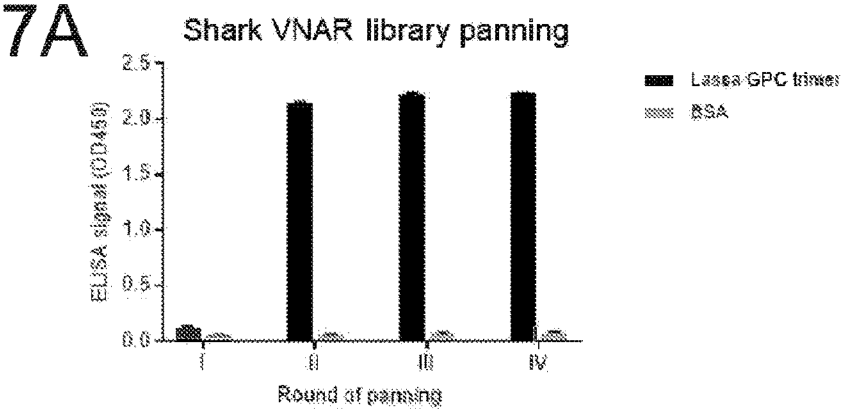
FIGS. 7A-7D: Identification of nanobodies by panning shark $V_{NAR}$ and camel $V_HH$ libraries against stabilized soluble LASV GPC trimer.
Figure 7B:
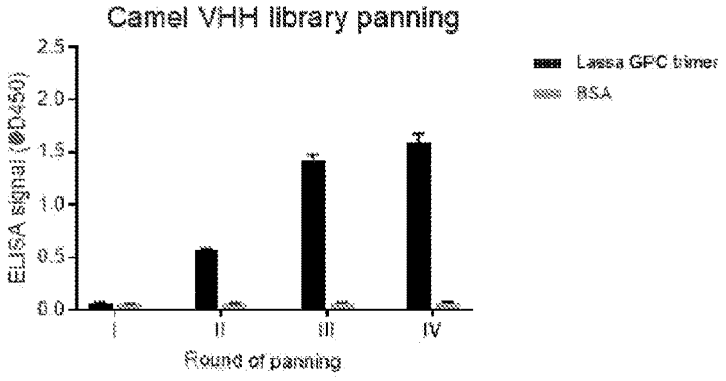
Figure 7C:
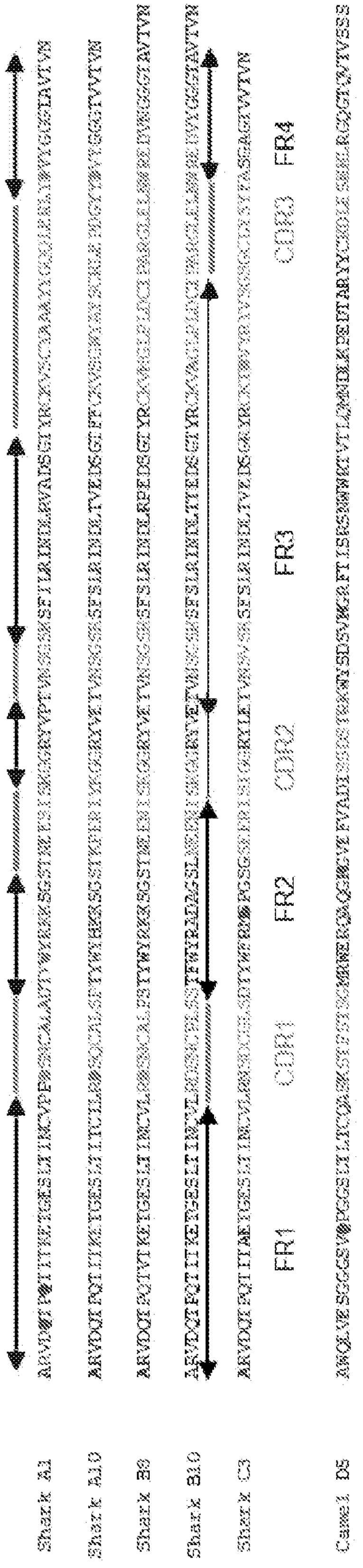
Figure 7D:
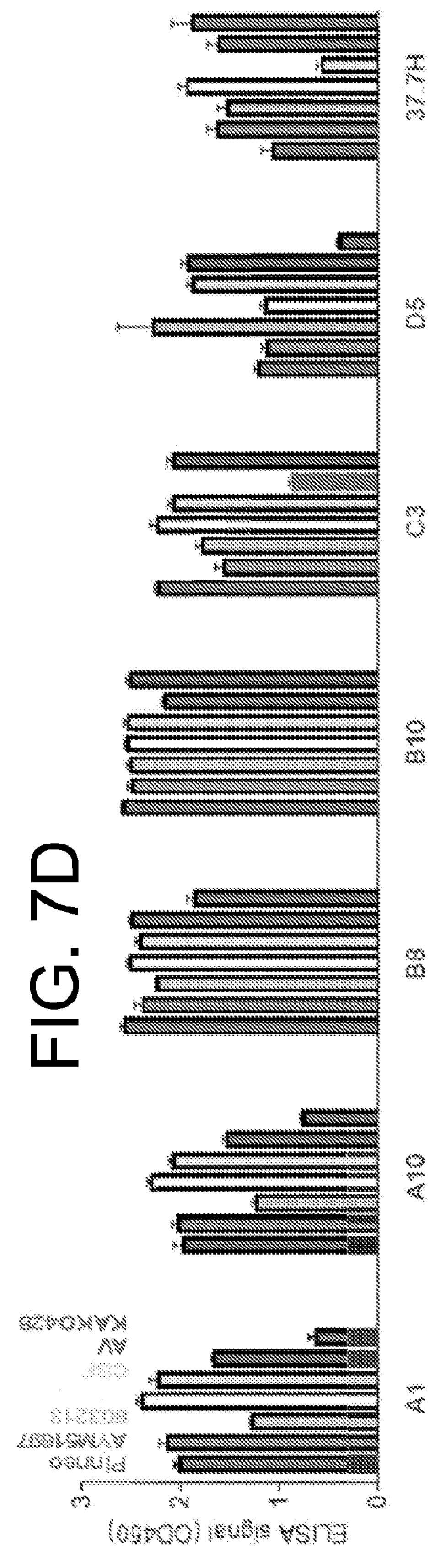
Figure 8A:
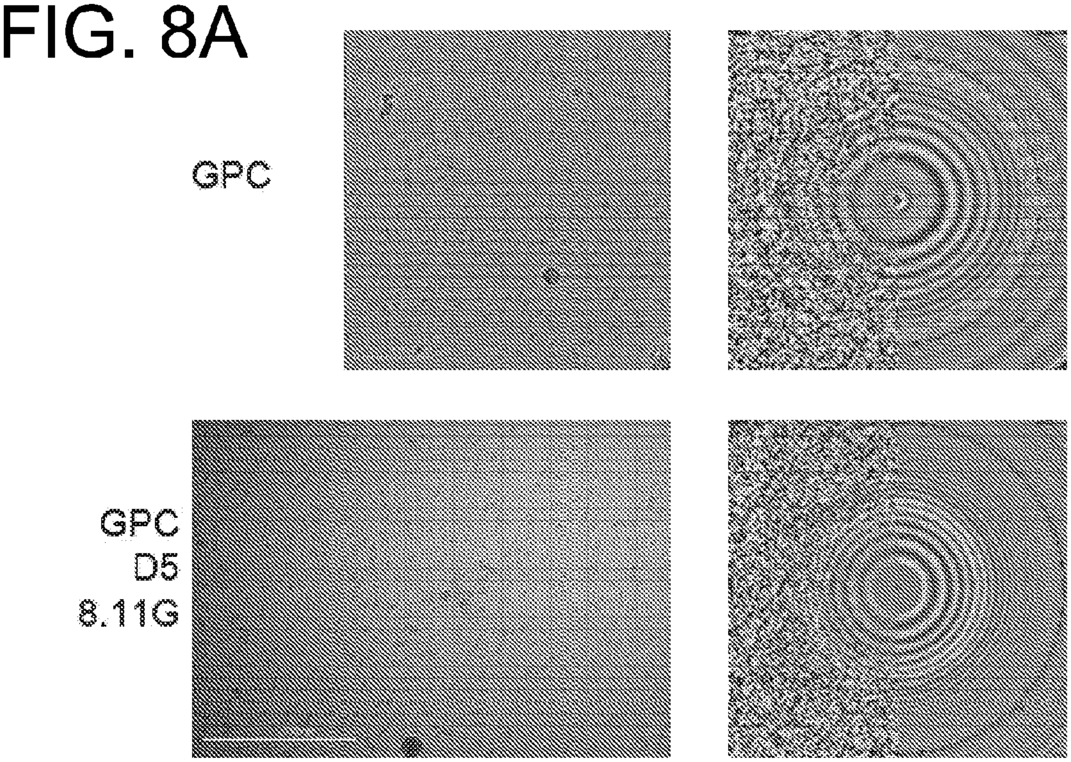
FIGS. 8A-8D: Cryo-EM details of stabilized GPC trimer unliganded and in complex with human Fab 8.11G and nanobody D5.
Figure 8B:
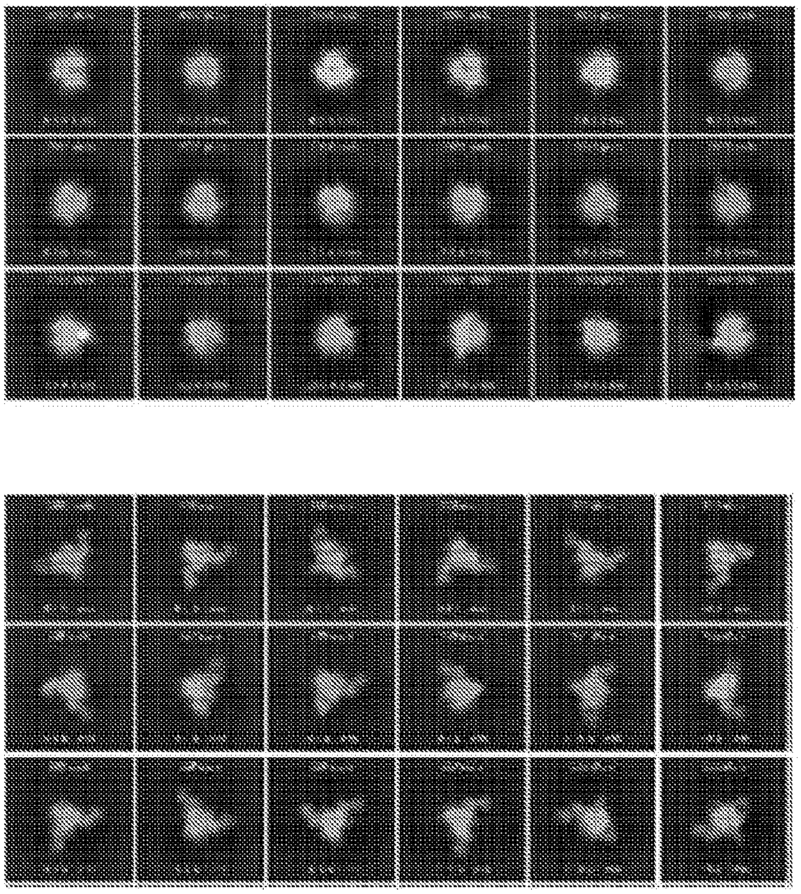
Figure 8D:
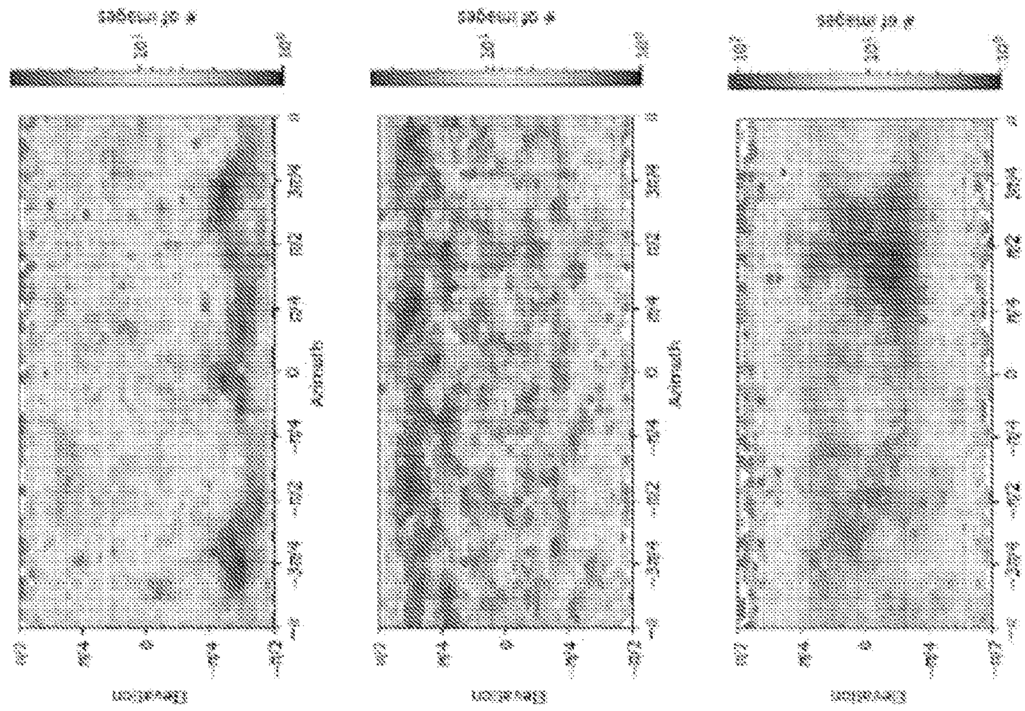
Figure 8C:
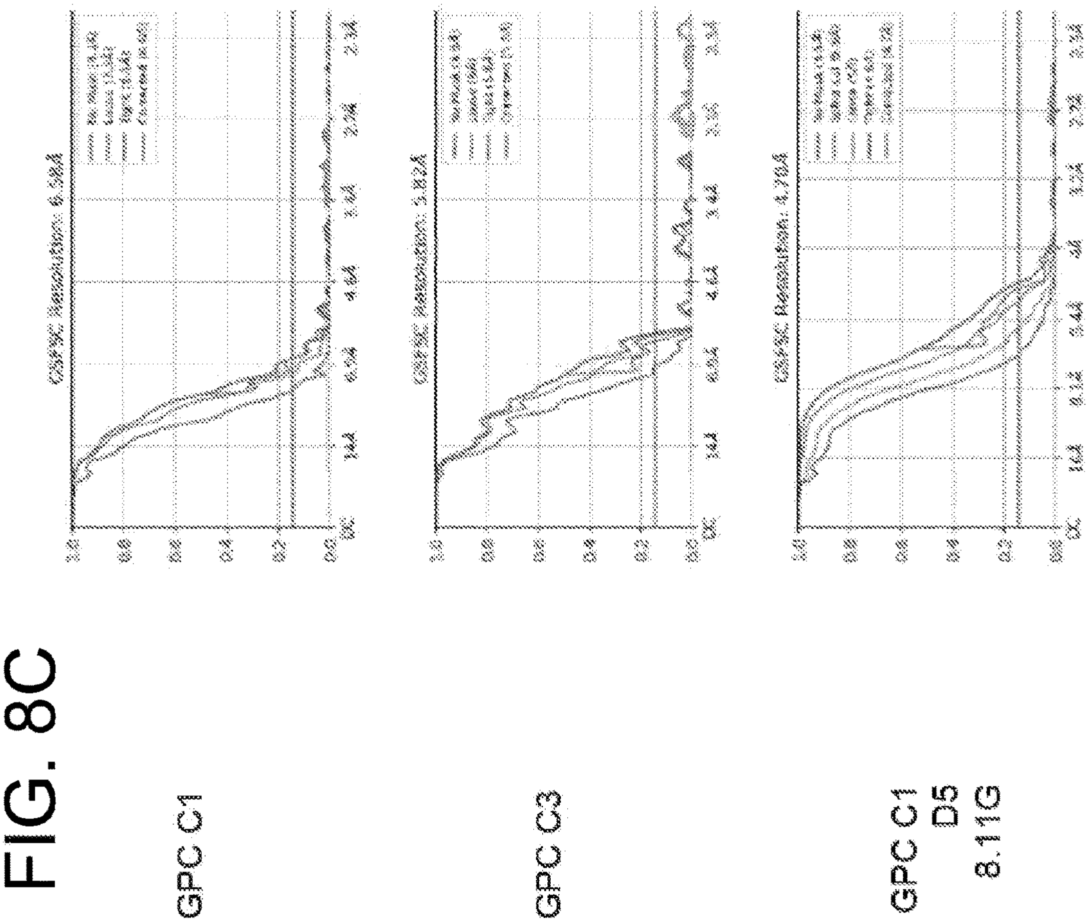

The structure of the trimer bound by D5 displayed an asymmetric assembly and when compared to the crystallized GPC, the neighboring protomer extended over 8 Å farther (FIG. 5D). This extension disrupted the 37.7H binding site and stabilization of this conformation by D5 prevents 37.7H from binding—providing an explanation for the competition observed between D5 and GPC-B antibodies, which bind across adjacent GPC protomers (FIG. 5E). The asymmetry in the protomer interface extensions is matched by the protrusion of an uncleaved furin site, between GP1 and GP2 (FIG. 5F). This results in two internal sites and a single protruding loop, disrupting the trimer symmetry and inflating the radius of the apex chalice targeted by D5.

Based on the cryo-EM structure, the amino acids of D5 that make contact with the GPC trimer (i.e., residues within a 5 Å footprint) were identified as residues 1-3, 5, 20, 23-33, 35, 37, 45, 47, 50, 52, 53, 57-62, 74-78, 93, 95, 97, 99-105 and 107 of SEQ ID NO: 1.

In view of the many possible embodiments to which the principles of the disclosure may be applied, it should be recognized that the illustrated embodiments are only examples and should not be taken as limiting the scope of the disclosure. Rather, the scope of the disclosure is defined by the following claims.

The invention claimed is:

1. A polypeptide that specifically binds Lassa virus (LASV) glycoprotein (GPC), wherein the polypeptide comprises:

(i) the complementarity determining region 1 (CDR1), CDR2 and CDR3 sequences of SEQ ID NO: 1, wherein the CDR1, CDR2 and CDR3 sequences respectively comprise:

residues 26-33, 51-58 and 97-104 of SEQ ID NO: 1;

residues 31-35, 50-66 and 97-104 of SEQ ID NO: 1; or residues 26-35, 47-60 and 97-105 of SEQ ID NO: 1; or (ii) the CDR1, hypervariable (HV) 2, HV4 and CDR3 sequences of SEQ ID NO: 2, SEQ ID NO: 3, SEQ ID NO: 4, SEQ ID NO: 5 or SEQ ID NO: 6, wherein the CDR1, HV2, HV4 and CDR3 sequences respectively comprise:

residues 26-33, 45-52, 60-64 and 84-102 of SEQ ID NO: 2;

residues 26-33, 45-52, 60-64 and 84-103 of SEQ ID NO: 3;

residues 26-33, 45-53, 60-64 and 84-103 of SEQ ID NO: 4;

residues 26-33, 45-52, 60-64 and 84-106 of SEQ ID NO: 5; or residues 26-33, 45-52, 60-64 and 84-106 of SEQ ID NO: 6.

2. The polypeptide of claim 1, wherein the amino acid sequence of the polypeptide is at least 90% identical to SEQ ID NO: 1, or wherein the amino acid sequence of the polypeptide comprises or consists of SEQ ID NO: 1.

3. The polypeptide of claim 1, wherein the amino acid sequence of the polypeptide is at least 90% identical to SEQ ID NO: 2, or wherein the amino acid sequence of the polypeptide comprises or consists of SEQ ID NO: 2.

4. The polypeptide of claim 1, wherein the amino acid sequence of the polypeptide is at least 90% identical to SEQ ID NO: 3, or wherein the amino acid sequence of the polypeptide comprises or consists of SEQ ID NO: 3.

5. The polypeptide of claim 1, wherein the amino acid sequence of the polypeptide is at least 90% identical to SEQ ID NO: 4, or wherein the amino acid sequence of the polypeptide comprises or consists of SEQ ID NO: 4.

6. The polypeptide of claim 1, wherein the amino acid sequence of the polypeptide is at least 90% identical to SEQ ID NO: 5, or wherein the amino acid sequence of the polypeptide comprises or consists of SEQ ID NO: 5.

7. The polypeptide of claim 1, wherein the amino acid sequence of the polypeptide is at least 90% identical to SEQ ID NO: 6, or wherein the amino acid sequence of the polypeptide comprises or consists of SEQ ID NO: 6.

8. The polypeptide of claim 1, wherein the polypeptide is a single-domain monoclonal antibody.

9. A fusion protein comprising the polypeptide of claim 1 and a heterologous protein.

10. A chimeric antigen receptor (CAR) comprising the polypeptide of claim 1.

11. An isolated cell expressing the CAR of claim 10.

12. An immunoconjugate comprising the polypeptide of claim 1 and an effector molecule.

13. An antibody-drug conjugate (ADC) comprising a drug conjugated to the polypeptide of claim 1.

14. A multi-specific antibody comprising the polypeptide of claim 1 and at least one additional monoclonal antibody or antigen-binding fragment thereof.

15. An antibody-nanoparticle conjugate, comprising a nanoparticle conjugated to the polypeptide of claim 1.

16. An isolated nucleic acid molecule encoding the polypeptide of claim 1.

17. A vector comprising the nucleic acid molecule of claim 16.

18. An isolated host cell comprising the nucleic acid molecule of claim 16.

19. A composition comprising a pharmaceutically acceptable carrier and the polypeptide of claim 1.

20. A method of detecting LASV in a sample, comprising:

contacting the sample with the polypeptide of claim 1;

detecting binding of the polypeptide to the sample, thereby detecting LASV in the sample.

21. A method of treating a LASV infection in a subject, comprising administering to the subject a therapeutically effective amount of the polypeptide of claim 1, thereby treating the LASV infection.

22. A solid support comprising one or more polypeptides of claim 1.

23. A method of detecting LASV in a sample, comprising:

contacting the sample with the solid support of claim 22; and detecting binding of LASV to the one or more polypeptides attached to the solid support, thereby detecting LASV in the sample.

* * * * *

```
                         SEQUENCE LISTING


<160> NUMBER OF SEQ ID NOS: 9

<210> SEQ ID NO 1
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 1

Ala Trp Gln Leu Val Glu Ser Gly Gly Gly Ser Val Gln Pro Gly Gly
1               5                   10                  15

Ser Leu Thr Leu Thr Cys Gln Ala Ser Lys Ser Thr Phe Ser Thr Ser
            20                  25                  30

Gly Met Arg Trp Glu Arg Gln Ala Gln Gly Lys Gly Val Glu Phe Val
        35                  40                  45

Ala Asp Ile Ser Ser Asp Ser Thr Arg Lys Trp Tyr Ser Asp Ser Val
    50                  55                  60

Lys Gly Arg Phe Thr Ile Ser Arg Ser Asn Trp Trp Arg Thr Val Thr
65                  70                  75                  80
```

Leu Gln Met Asn Asp Leu Lys Pro Glu Asp Thr Ala Arg Tyr Tyr Cys
85 90 95

Lys Asp Leu Glu Ser His His Leu Arg Gly Gln Gly Thr Gln Val Thr
100 105 110

Val Ser Ser
115

<210> SEQ ID NO 2
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 2

Ala Arg Val Asp Gln Thr Pro Gln Thr Ile Thr Ala Glu Thr Gly Glu
1 5 10 15

Ser Leu Thr Ile Asn Cys Val Leu Arg Asn Ser Asp Cys Gly Leu Ser
20 25 30

Asp Thr Tyr Trp Phe Arg Met Ser Pro Gly Ser Gly Ser Glu Glu Arg
35 40 45

Ile Ser Ile Gly Gly Arg Tyr Leu Glu Thr Val Asn Ser Val Ser Lys
50 55 60

Ser Phe Ser Leu Arg Ile Asn Asp Leu Thr Val Glu Asp Ser Gly Arg
65 70 75 80

Tyr Arg Cys Lys Thr Asp Val Tyr Arg Tyr Val Ser Gly Ser Gly Cys
85 90 95

Leu Tyr Ser Tyr Phe Ala Ser Gly Ala Gly Thr Val Val Thr Val Asn
100 105 110

<210> SEQ ID NO 3
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 3

Ala Arg Val Asp Gln Thr Pro Gln Thr Ile Thr Lys Glu Thr Gly Glu
1 5 10 15

Ser Leu Thr Ile Asn Cys Val Pro Pro Asp Ser Asn Cys Ala Leu Ala
20 25 30

Asp Thr Tyr Trp Tyr Arg Lys Lys Ser Gly Ser Thr Asn Glu Glu Ser
35 40 45

Ile Ser Lys Gly Gly Arg Tyr Val Pro Thr Val Asn Ser Gly Ser Lys
50 55 60

Ser Phe Ile Leu Arg Ile Asn Asp Leu Arg Val Ala Asp Ser Gly Thr
65 70 75 80

Tyr Arg Cys Lys Val Ser Cys Tyr Ala Ala Ala Tyr Tyr Gly Gln Gln
85 90 95

Leu Glu Arg Leu Tyr Asp Val Tyr Gly Gly Gly Thr Ala Val Thr Val
100 105 110

Asn

<210> SEQ ID NO 4
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 4

Ala Arg Val Asp Gln Thr Pro Gln Thr Ile Thr Lys Glu Thr Gly Glu
1 5 10 15

Ser Leu Thr Ile Thr Cys Ile Leu Arg Asp Ser Gln Cys Ala Leu Ser
20 25 30

Pro Thr Tyr Trp Tyr His Lys Lys Ser Gly Ser Thr Lys Pro Glu Arg
35 40 45

Ile Tyr Lys Gly Gly Arg Tyr Val Glu Thr Val Asn Ser Gly Ser Lys
50 55 60

Ser Phe Ser Leu Arg Ile Asn Asp Leu Thr Val Glu Asp Ser Gly Thr
65 70 75 80

Phe Phe Cys Lys Val Ser Gly Trp Tyr Ala Tyr Ser Cys Arg Leu Glu
85 90 95

Pro Asp Gly Tyr Tyr Asp Val Tyr Gly Gly Gly Thr Val Val Thr Val
100 105 110

Asn

<210> SEQ ID NO 5
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 5

Ala Arg Val Asp Gln Thr Pro Gln Thr Val Thr Lys Glu Thr Gly Glu
1 5 10 15

Ser Leu Thr Ile Asn Cys Val Leu Arg Asp Ser Asn Cys Ala Leu Pro
20 25 30

Ser Thr Tyr Trp Tyr Arg Lys Lys Ser Gly Ser Thr Asn Glu Glu Asn
35 40 45

Ile Ser Lys Gly Gly Arg Tyr Val Glu Thr Val Asn Ser Gly Ser Lys
50 55 60

Ser Phe Ser Leu Arg Ile Asn Asp Leu Arg Pro Glu Asp Ser Gly Thr
65 70 75 80

Tyr Arg Cys Lys Val His Gly Leu Pro Leu Asp Cys Ile Pro Ala Arg
85 90 95

Gly Leu Glu Leu Asn Trp Arg Glu Asp Val Asn Gly Gly Gly Thr Ala
100 105 110

Val Thr Val Asn
115

<210> SEQ ID NO 6
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 6

Ala Arg Val Asp Gln Thr Pro Gln Thr Ile Thr Lys Glu Thr Gly Glu
1 5 10 15

Ser Leu Thr Ile Asn Cys Val Leu Arg Asp Ser Asn Cys Pro Leu Ser
20 25 30

Ser Thr Phe Trp Tyr Arg Ala Asp Ala Gly Ser Leu Asn Glu Glu Asn

```
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Thr Glu Asp Ser Gly Thr
65                  70                  75                  80

Tyr Arg Cys Lys Val Ala Gly Leu Pro Leu Asp Cys Ile Pro Ala Arg
                85                  90                  95

Gly Leu Glu Leu Asn Trp Arg Glu Asp Val Tyr Gly Gly Gly Thr Ala
            100                 105                 110

Val Thr Val Asn
        115


<210> SEQ ID NO 7
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 7

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Cys Thr Cys Pro
            20                  25                  30

Lys Cys Pro
        35


<210> SEQ ID NO 8
<211> LENGTH: 454
<212> TYPE: PRT
<213> ORGANISM: Artificial Sequence
<220> FEATURE:
<223> OTHER INFORMATION: Synthetic polypeptide

<400> SEQUENCE: 8

Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
            20                  25                  30

Lys Gly Leu Tyr Asn Phe Ala Thr Cys Gly Leu Val Gly Leu Val Thr
        35                  40                  45

Phe Leu Leu Leu Cys Gly Arg Ser Cys Thr Thr Ser Leu Tyr Lys Gly
    50                  55                  60

Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
            100                 105                 110

Ile Asn His Lys Phe Cys Asn Leu Ser Asp Ala His Lys Lys Asn Leu
        115                 120                 125

Tyr Asp His Ala Leu Met Ser Ile Ile Ser Thr Phe His Leu Ser Ile
    130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175
```

```
Ala Asn His Cys Gly Thr Val Ala Asn Gly Val Leu Gln Thr Phe Met
            180                 185                 190

Arg Met Ala Trp Gly Gly Ser Tyr Ile Ala Leu Asp Ser Gly Gly Cys
        195                 200                 205

Gly Asn Trp Asp Cys Ile Met Thr Ser Tyr Gln Tyr Leu Ile Ile Gln
    210                 215                 220

Asn Thr Thr Trp Glu Asp His Cys Gln Phe Ser Arg Pro Ser Pro Ile
225                 230                 235                 240

Gly Tyr Leu Gly Leu Leu Ser Gln Arg Thr Arg Asp Ile Tyr Ile Ser
                245                 250                 255

Arg Arg Arg Arg Gly Thr Phe Thr Trp Thr Leu Ser Asp Ser Glu Gly
            260                 265                 270

Lys Asp Thr Pro Gly Gly Tyr Cys Leu Thr Arg Trp Met Leu Ile Glu
        275                 280                 285

Ala Glu Leu Lys Cys Phe Gly Asn Thr Ala Val Ala Lys Cys Asn Glu
    290                 295                 300

Lys His Asp Glu Glu Phe Cys Asp Met Leu Arg Leu Phe Asp Phe Asn
305                 310                 315                 320

Lys Gln Ala Ile Gln Arg Cys Lys Ala Pro Ala Gln Met Ser Ile Gln
                325                 330                 335

Leu Ile Asn Lys Ala Val Asn Ala Leu Ile Asn Asp Gln Leu Ile Met
            340                 345                 350

Lys Asn His Leu Arg Asp Ile Met Gly Ile Pro Tyr Cys Asn Tyr Ser
        355                 360                 365

Lys Tyr Trp Tyr Leu Asn His Thr Thr Thr Gly Arg Thr Ser Leu Pro
    370                 375                 380

Lys Cys Trp Leu Val Ser Asn Gly Ser Tyr Leu Asn Glu Thr His Phe
385                 390                 395                 400

Ser Asp Asp Ile Glu Gln Gln Ala Asp Asn Met Ile Thr Glu Met Leu
                405                 410                 415

Gln Lys Glu Gly Gly Gly Tyr Ile Pro Glu Ala Pro Arg Asp Gly Gln
            420                 425                 430

Ala Tyr Val Arg Lys Asp Gly Glu Trp Val Leu Leu Ser Thr Phe Leu
        435                 440                 445

Gly Gly Leu Val Pro Arg
    450


<210> SEQ ID NO 9
<211> LENGTH: 345
<212> TYPE: DNA
<213> ORGANISM: Artificial Sequence
<220> FEATURE:
<223> OTHER INFORMATION: Synthetic nucleic acid

<400> SEQUENCE: 9

gcgtggcagc tggtggagtc tgggggaggc tcggtgcagc cgggggggctc tctgacactc      60

acctgtcaag cttccaaatc tacgttcagt acgtccggca tgcggtggga gcgccaggct     120

caagggaagg gagtggaatt tgtcgcagat attagtagtg atagtacgag gaaatggtat     180

tcagactccg tgaagggccg attcacgatc tccagaagca actggtggag gacggtgact     240

ctacagatga acgatctgaa acctgaggac acggcccgtt attattgtaa agatcttgag     300

tcccaccatc tacggggcca ggggacccag gtcaccgtct cctca                    345
```